(12) United States Patent
Egawa et al.

(10) Patent No.: US 8,283,052 B2
(45) Date of Patent: Oct. 9, 2012

(54) QUINOXALINE DERIVATIVE, LIGHT-EMITTING ELEMENT, LIGHT-EMITTING DEVICE, AND ELECTRONIC APPLIANCE

(75) Inventors: Masakazu Egawa, Oyama (JP); Atsushi Tokuda, Kanagawa (JP); Satoko Shitagaki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1058 days.

(21) Appl. No.: 11/860,190

(22) Filed: Sep. 24, 2007

(65) Prior Publication Data

US 2008/0193794 A1    Aug. 14, 2008

(30) Foreign Application Priority Data

Sep. 29, 2006    (JP) ................................ 2006-268356

(51) Int. Cl.
   *H01L 51/54*    (2006.01)
   *C09K 11/06*    (2006.01)

(52) U.S. Cl. ........ 428/690; 428/917; 313/504; 313/506; 252/301.16; 257/40; 257/103; 257/E51.05; 544/349

(58) Field of Classification Search ........................ None
See application file for complete search history.

(56) References Cited

U.S. PATENT DOCUMENTS

| 3,765,898 | A | 10/1973 | Bauer et al. | |
|---|---|---|---|---|
| 5,077,142 | A * | 12/1991 | Sakon et al. | 428/690 |
| 6,482,949 | B1 | 11/2002 | Sessler et al. | |
| 6,717,358 | B1 * | 4/2004 | Liao et al. | 313/504 |
| 6,723,445 | B2 | 4/2004 | Li et al. | |
| 2005/0003232 | A1 | 1/2005 | Shitagaki et al. | |

FOREIGN PATENT DOCUMENTS

| CH | 599 569 | 5/1978 |
|---|---|---|
| JP | 9-13025 | 1/1997 |
| JP | 2003-40873 | 2/2000 |
| JP | 2002-100479 | 4/2002 |
| WO | WO 2006/022193 A1 | 3/2006 |

OTHER PUBLICATIONS

Chen et al. "Doubly ortho-linked quinoxaline/diphenylflourene hybrids as bipolar fluorescent chameleons for optoelectronic applications." J. Am. CHem. Soc. 2006, vol. 128, pp. 10992-10993.*
Aldakov et al. "Benzothiazoles and dipyrrolyl quinoxalines with extended conjugated chromophores—fluorophores and anion sensors."Chem. Mater. 2005, vol. 17, pp. 5238-5241.*
English machine translation of JP 2003/040873 A, 2003.*
Black, C. B. et al., "Dipyrrolylquinoxalines: Efficient Sensors for Fluoride Anion in Organic Solution," J. Am. Chem. Soc, vol. 121, 1999, pp. 10438-10439.
Anzenbacher, Jr., P. et al., "Fluorinated Calix[4]pyrrole and Dipyrrolylquinoxaline: Neutral Anion Receptors with Augmented Affinities and Enhanced Selectivities," J. Am. Chem. Soc, vol. 122, 2000, pp. 10268-10272.
Aldakov, D. et al., "Dipyrrolyl Quinoxalines With Extended Chromophores are Efficient Fluorimetric Sensors for Pyrophosphate," CHEM. COMMUN., 2003, pp. 1394-1395.
Pohl, R. et al., "Strategies Toward Improving the Performance of Fluorescence-Based Sensors for Inorganic Anions," CHEM. COMMUN., 2004, pp. 1282-1283.
Black, C. B. et al., "Dipyrrolylquinoxalines: Efficient Sensors for Fluoride Anion in Organic Solution," J. Am. Chem. Soc, vol. 121, No. 44, 1999, pp. 10438-10439.
Anzenbacher, Jr., P. et al., "Fluorinated Calix[4]pyrrole and Dipyrrolylquinoxaline: Neutral Anion Receptors with Augmented Affinities and Enhanced Selectivities," J. Am. Chem. Soc, vol. 122, No. 42, 2000, pp. 10268-10272.

* cited by examiner

*Primary Examiner* — Jennifer Chriss
*Assistant Examiner* — Michael H Wilson
(74) *Attorney, Agent, or Firm* — Husch Blackwell LLP

(57) ABSTRACT

It is an object to provide a new substance excellent in electron-transporting property, and a light-emitting element and a light-emitting device using the substance. A quinoxaline derivative represented by the general formula (G1) is provided. In the general formula (G1), each of $R^1$ to $R^4$ represents hydrogen, an alkyl group having 1 to 4 carbon atoms, or an aryl group having 6 to 25 carbon atoms; and each of $Ar^1$ and $Ar^2$ represents an aryl group having 6 to 25 carbon atoms. Such a quinoxaline derivative is excellent in electron-transporting property and very effective as an electron-transporting material in a light-emitting element and the like.

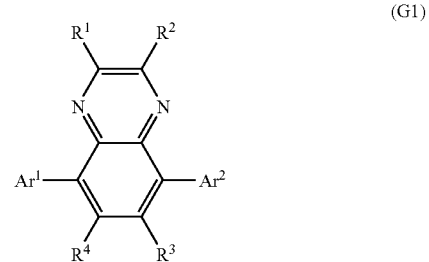

(G1)

5 Claims, 17 Drawing Sheets

QUINOXALINE DERIVATIVE, LIGHT-EMITTING ELEMENT, LIGHT-EMITTING DEVICE, AND ELECTRONIC APPLIANCE

BACKGROUND OF THE INVENTION

1. Field of the Invention

The present invention relates to a quinoxaline derivative, a light-emitting element using the quinoxaline derivative, and a light-emitting device and an electronic appliance including the light-emitting element. More specifically, the present invention relates to a quinoxaline derivative having an excellent electron-transporting property, a light-emitting element using the quinoxaline derivative, and a light-emitting device and an electronic appliance including the light-emitting element.

2. Description of the Related Art

An organic compound has various material systems compared to an inorganic compound, and has possibility to synthesize materials having various functions depending on the molecular design. Owing to these advantages, electronics (particularly, photo electronics) which uses a functional organic material has been attracting attention in recent years. For example, a solar battery, a light-emitting element, an organic transistor, and the like can be mentioned as examples of an electronic device using an organic compound as a functional organic material. These are devices taking advantage of electric properties and optical properties of the organic compound. Among them, in particular, a light-emitting element has been developing remarkably.

Such a light-emitting element which is thin, lightweight, and capable of fast response is expected to be applied to a next-generation flat panel display. In addition, it is said that a light-emitting device in which light-emitting elements are arranged in matrix has advantages over the conventional liquid crystal display devices in that the viewing angle is wide and visibility is high.

A light-emitting element has a structure in which a layer including a light-emitting substance is interposed between a pair of electrodes (anode and cathode). It is said that, in such a light-emitting element, when a voltage is applied between a pair of electrodes, electrons injected from a cathode and holes injected from an anode are recombined in the layer including a light-emitting substance so as to form an exciton of the light-emitting substance, and light is emitted when the exciton returns to a ground state.

Such a light-emitting element has a lot of problems in materials in the case where an element property thereof is intended to be improved. In order to solve the problems, improvement of an element structure, development of materials, and the like have been carried out. In particular, an organic semiconductor material is inherently a hole-transporting material in many cases. Thus, currently, hole mobility of a hole-transporting material is higher than electron mobility of an electron-transporting material by several digits. Therefore, an electron-transporting material having an excellent electron-transporting property is desired to be obtained.

A light-emitting element has been reported, which uses a quinoxaline derivative as such a material excellent in electron-transporting property (Patent Document 1: Japanese Published Patent Application No. H9-13025). However, the light-emitting element has high drive voltage and is not yet perfect. Accordingly, various researches have been made in order to improve an electron-transporting property in a light-emitting element (Patent Document 2: Japanese Published Patent Application No. 2002-100479).

SUMMARY OF THE INVENTION

In view of the above, it is an object of the present invention to provide a quinoxaline derivative having an excellent electron-transporting property. In addition, it is another object to provide a light-emitting element with low drive voltage by using the quinoxaline derivative.

One aspect of the present invention is a quinoxaline derivative represented by the general formula (G1).

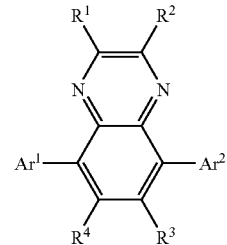

(G1)

In the general formula (G1), each of $R^1$ to $R^4$ represents hydrogen, an alkyl group having 1 to 4 carbon atoms, or an aryl group having 6 to 25 carbon atoms; and each of $Ar^1$ and $Ar^2$ represents an aryl group having 6 to 25 carbon atoms.

Another aspect of the present invention is a quinoxaline derivative represented by the general formula (G2).

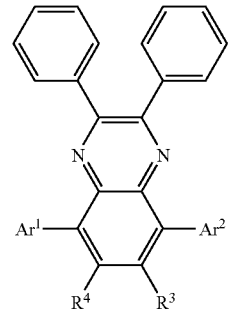

(G2)

In the general formula (G2), each of $R^3$ and $R^4$ represents hydrogen, an alkyl group having 1 to 4 carbon atoms, or an aryl group having 6 to 25 carbon atoms; and each of $Ar^1$ and $Ar^2$ represents an aryl group having 6 to 25 carbon atoms.

Another aspect of the present invention is a quinoxaline derivative represented by the general formula (G3).

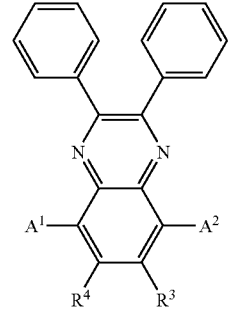

(G3)

In the general formula (G3), each of $R^3$ and $R^4$ represents hydrogen, an alkyl group having 1 to 4 carbon atoms, or an aryl group having 6 to 25 carbon atoms; and each of $Ar^1$ and $Ar^2$ has any one of structures represented by the following structural formulas (G3-1) to (G3-3).

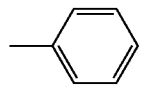
(G3-1)

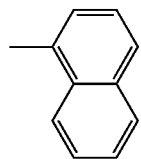
(G3-2)

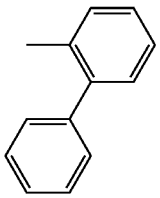
(G3-3)

Another aspect of the present invention is the quinoxaline derivative represented by the general formula (G3), wherein $A^1$ and $A^2$ have the same structure. In the above structure, a substituent representing either hydrogen or an alkyl group having 1 to 4 carbon atoms can be represented by, for example, any of the structural formulas (1'-1) to (1'-9).

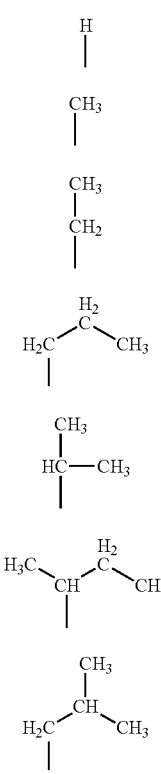

(1'-1)
(1'-2)
(1'-3)
(1'-4)
(1'-5)
(1'-6)
(1'-7)
(1'-8)
(1'-9)

In the above structure, a substituent representing an aryl group having 6 to 25 carbon atoms can be represented by, for example, any of the structural formulas (2'-1) to (2'-7).

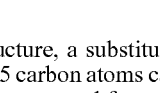
(2'-1)

(2'-2)

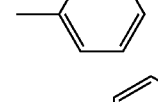
(2'-3)

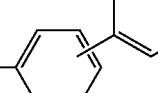
(2'-4)

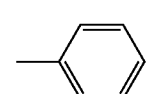
(2'-5)

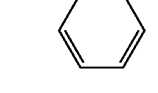
(2'-6)

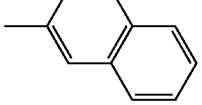
(2'-7)

Another aspect of the present invention is a light-emitting element including the quinoxaline derivative between a pair of electrodes. Further, another aspect of the present invention is that the quinoxaline derivative between a pair of electrodes is used as an electron-transporting material.

Another aspect of the present invention is a light-emitting element including a light-emitting layer between a pair of electrodes, and the light-emitting layer includes the quinoxaline derivative. Further, another aspect of the present invention is a light-emitting element including a light-emitting layer between a pair of electrodes, and the light-emitting layer includes the quinoxaline derivative and a substance which emits fluorescence. Note that the light-emitting layer may also include the quinoxaline derivative and a substance which emits phosphorescence.

Another aspect of the present invention is a light-emitting device and an electronic appliance including the light-emitting element as described above.

According to the present invention, a quinoxaline derivative excellent in electron-transporting property can be obtained. In addition, by applying the quinoxaline derivative of the present invention to a light-emitting element, an element with low drive voltage can be provided. Further, by using the light-emitting element including the quinoxaline derivative of the present invention, a light-emitting device with low power consumption and an electronic appliance provided with the light-emitting device can be provided.

DESCRIPTION OF THE INVENTION

Figure 1:
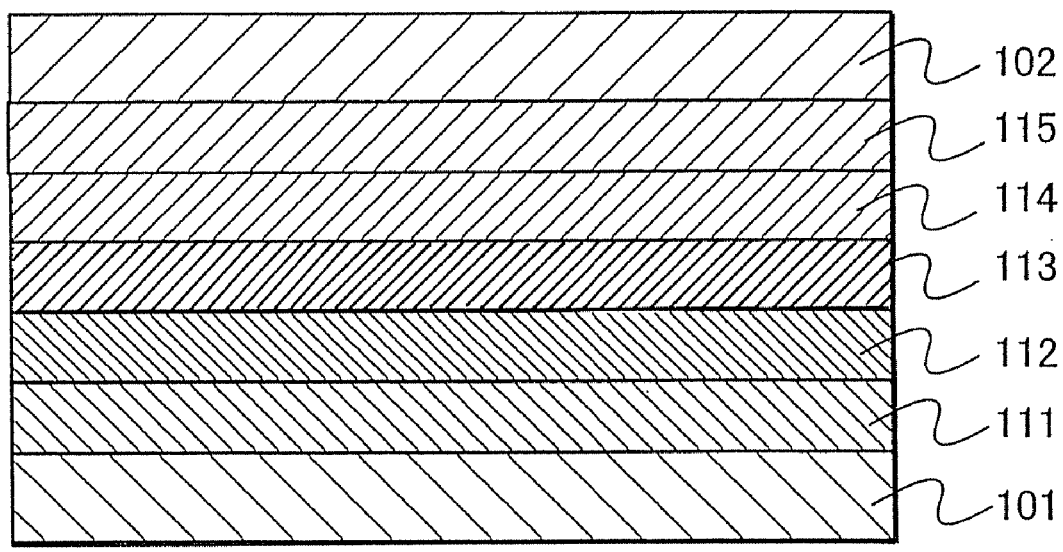
FIG. 1 is an explanatory view of an element structure of a light-emitting element according to the present invention.

Hereinafter, embodiment modes of the present invention will be described in detail with reference to the accompanying drawings. Note that the present invention is not limited to the following description, and it is easily understood by those skilled in the art that modes and details thereof can be modified in various ways without departing from the spirit and scope of the present invention. Therefore, the present invention should not be interpreted as being limited to the following description of the embodiment modes.

(Embodiment Mode 1)

One mode of the present invention is a quinoxaline derivative represented by the following structural formulas (1) to (83). Note that the quinoxaline derivative of the present invention is not limited to the ones represented by the following structural formulas.

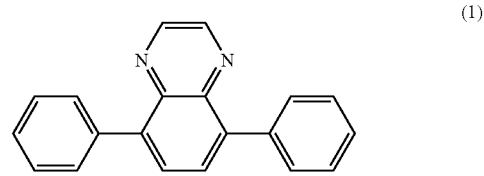

(1)

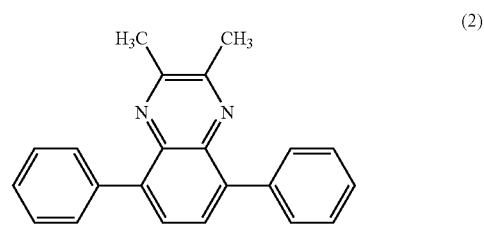

(2)

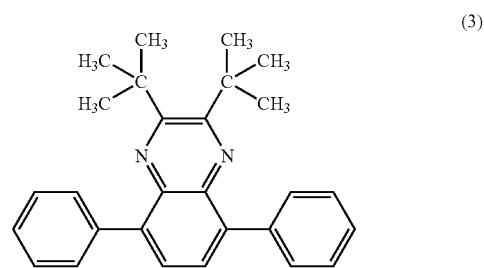

(3)

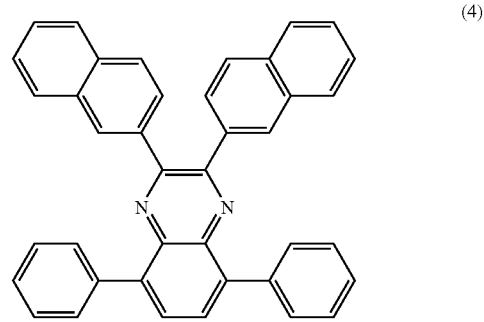

(4)

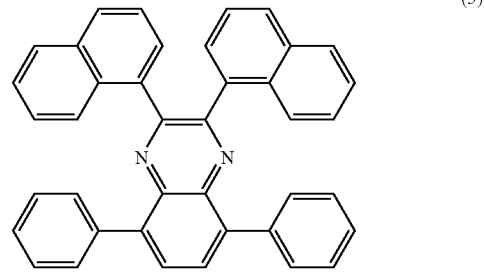

(5)

(6)
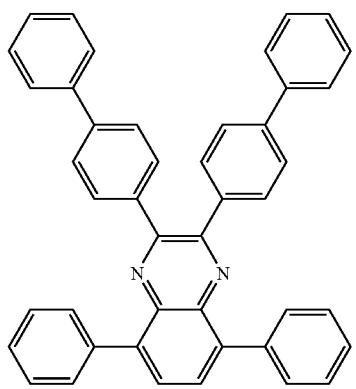
(7)
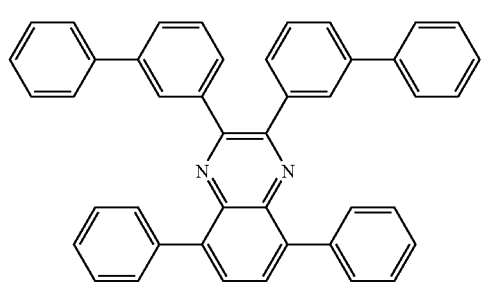
(8)
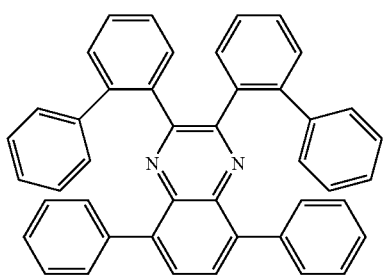
(9)
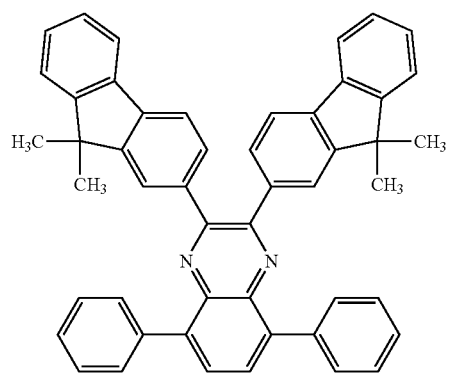
(10)
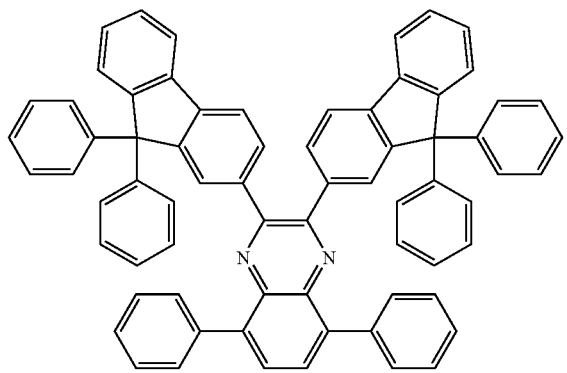
(11)
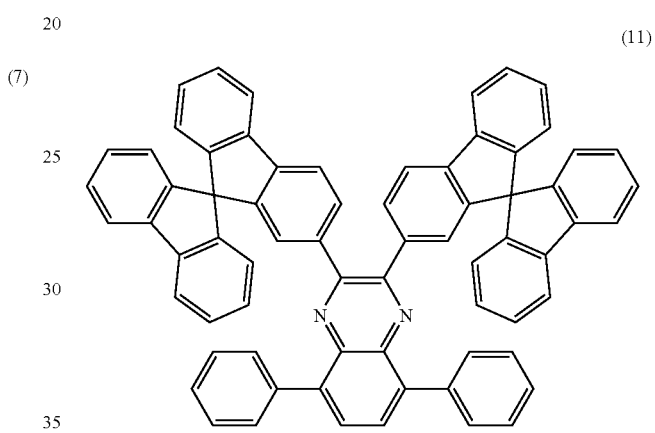
(12)
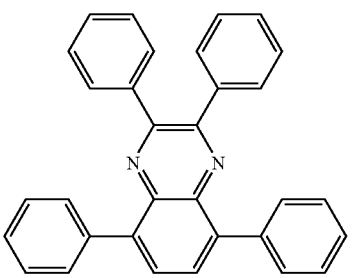
(13)
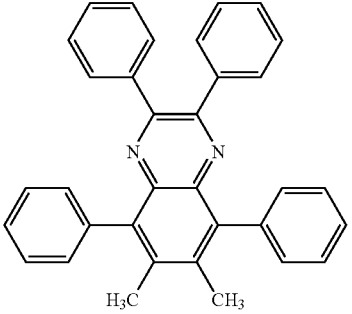

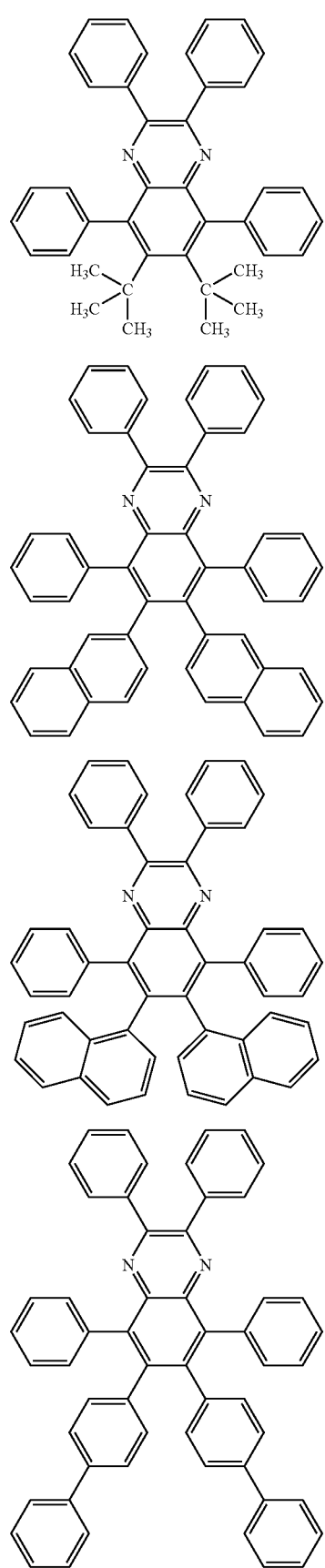
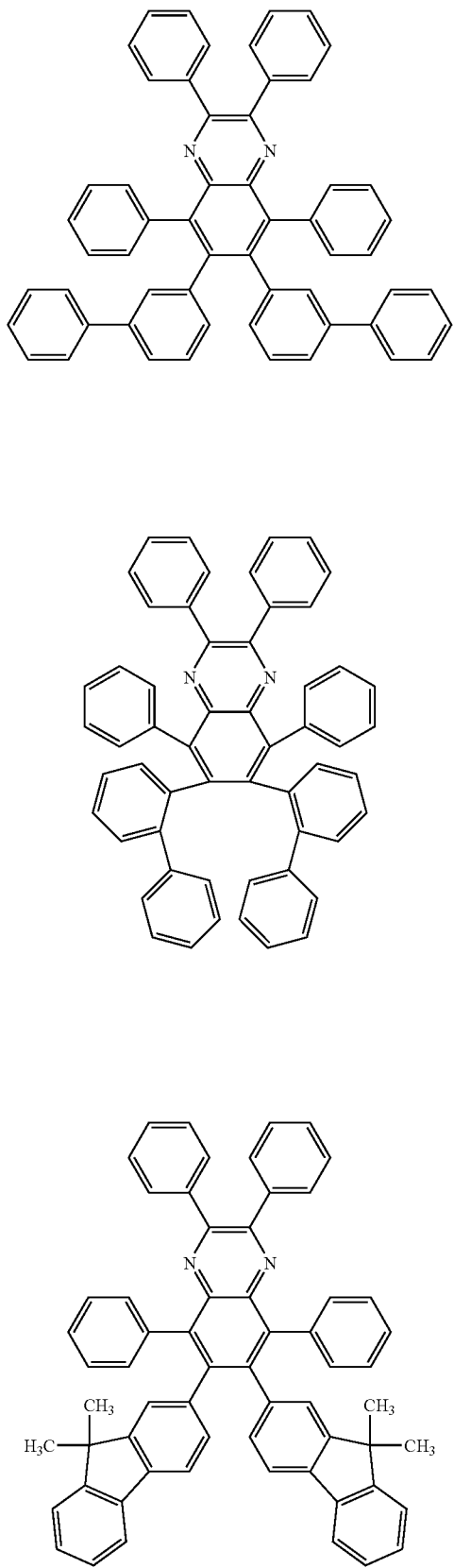

(21)
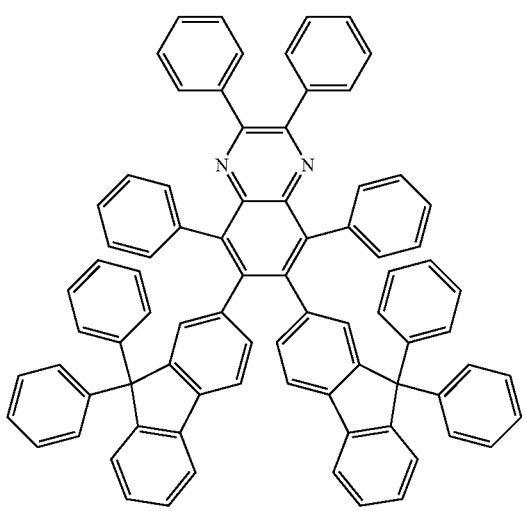
(22)
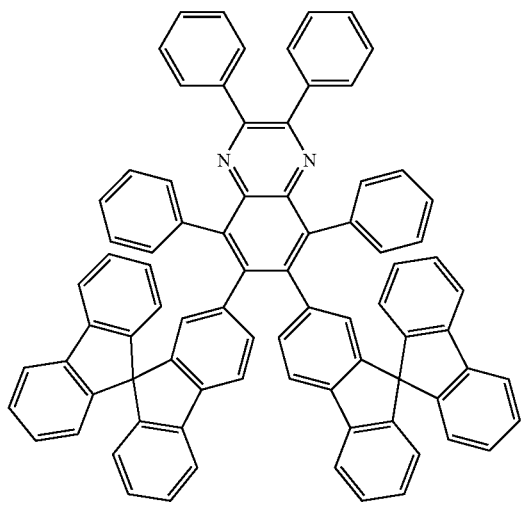
(23)
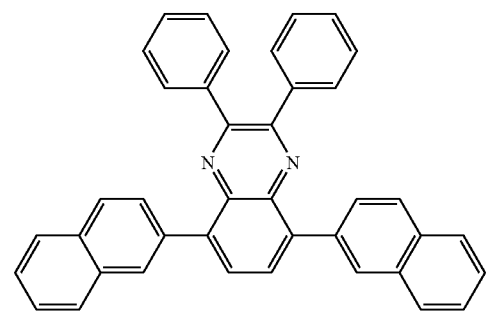
(24)
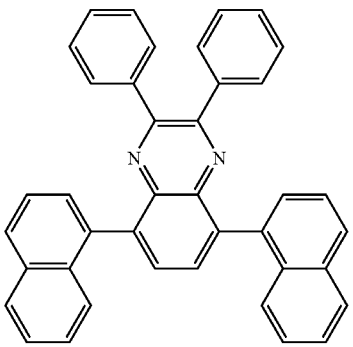
(25)
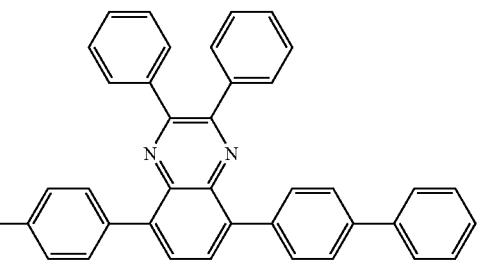
(26)
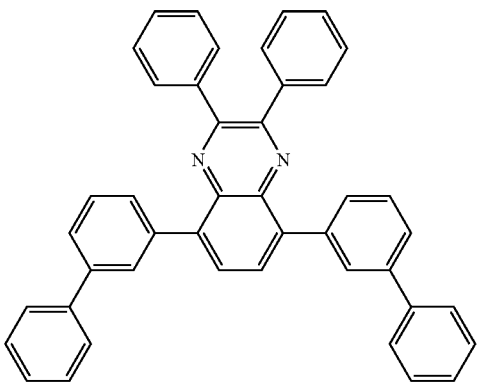
(27)
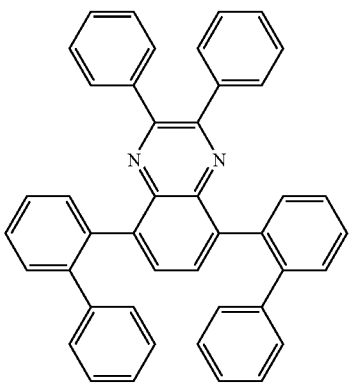

(28)
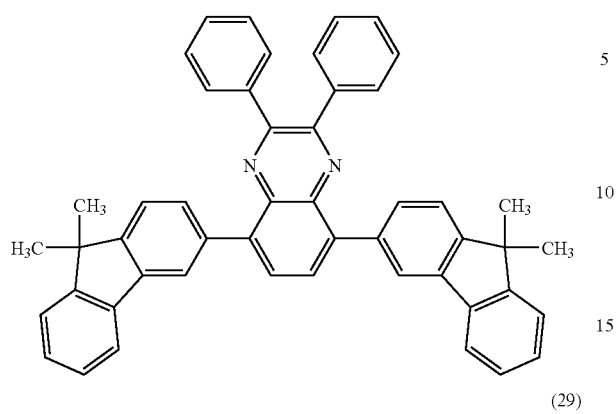
(29)
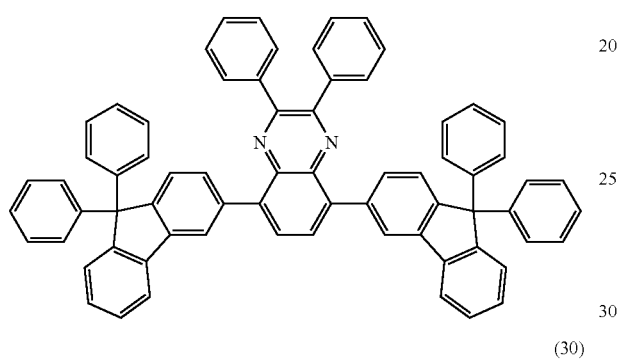
(30)
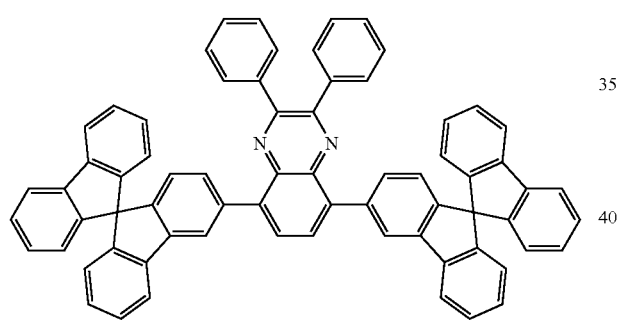
(31)
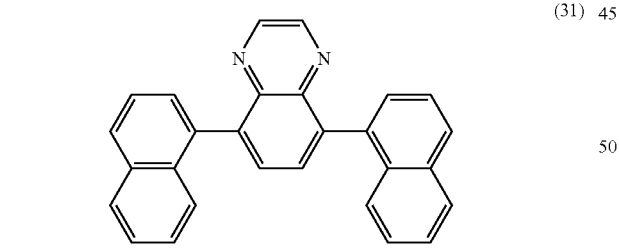
(32)
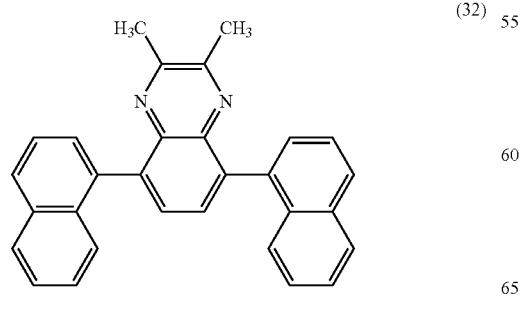
(33)
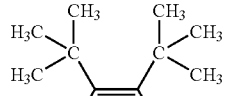
(34)
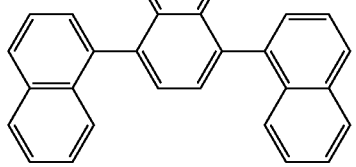
(35)
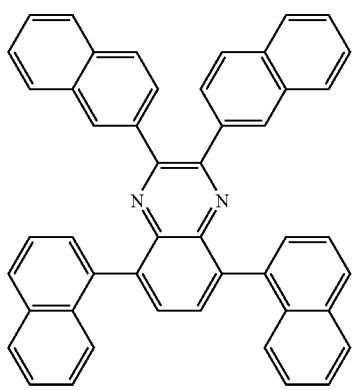
(36)
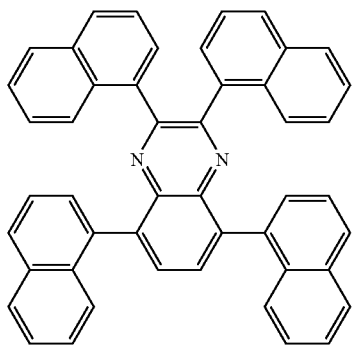
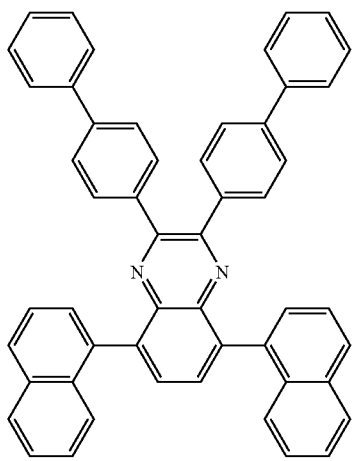

(37)
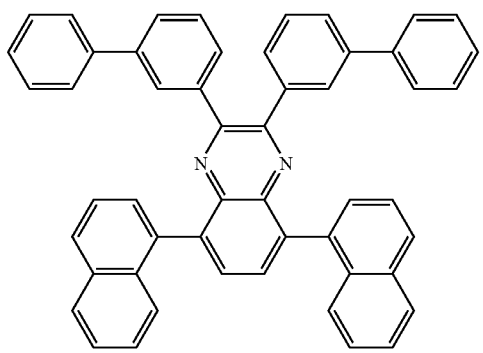
(38)
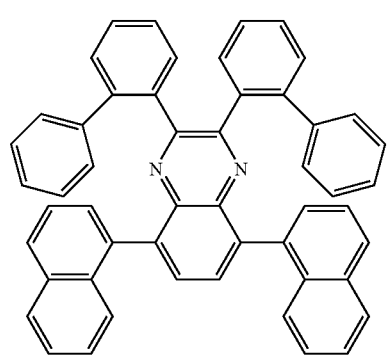
(39)
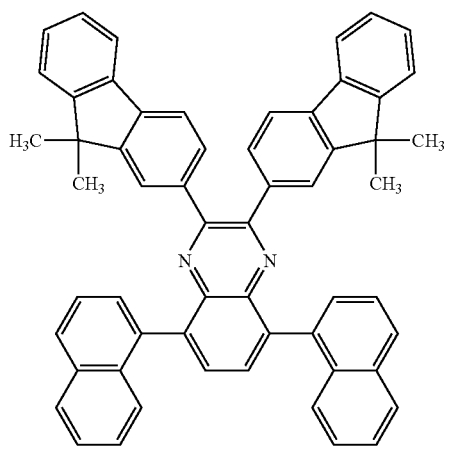
(40)
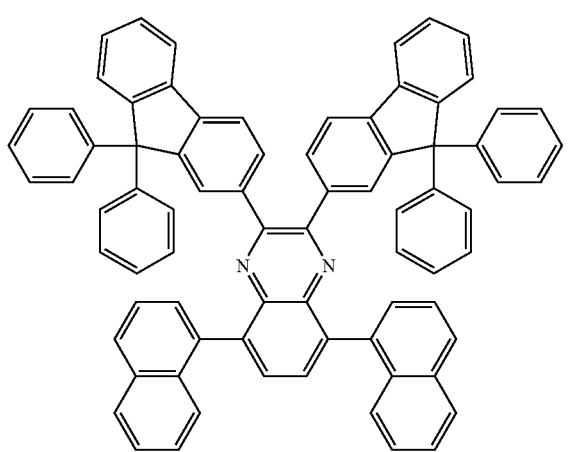
(41)
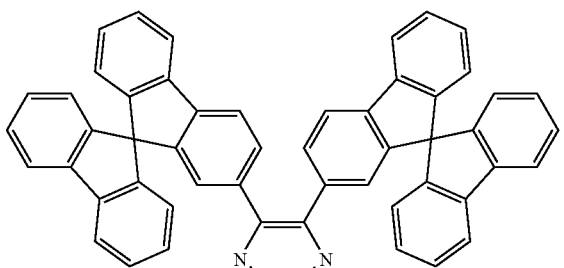
(42)
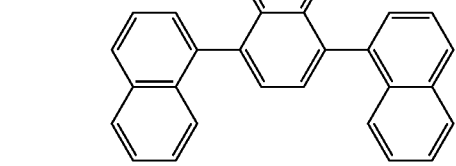
(43)
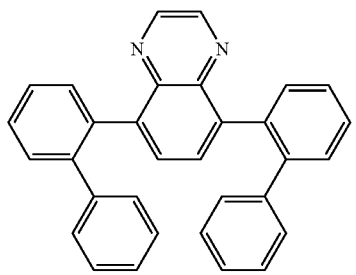
(44)
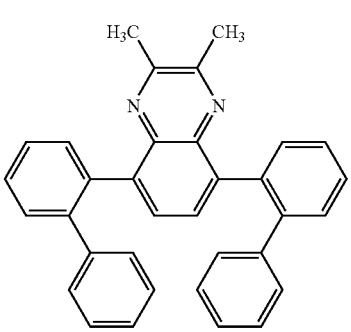

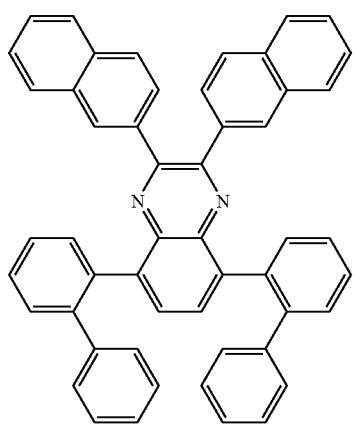
(45)
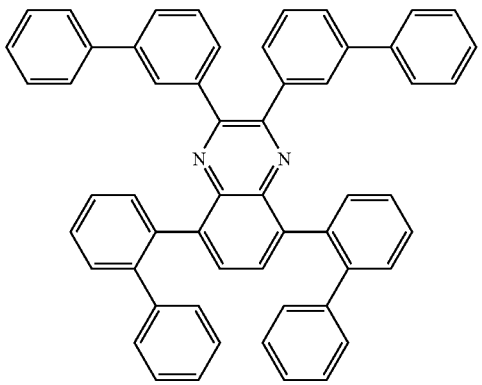
(48)
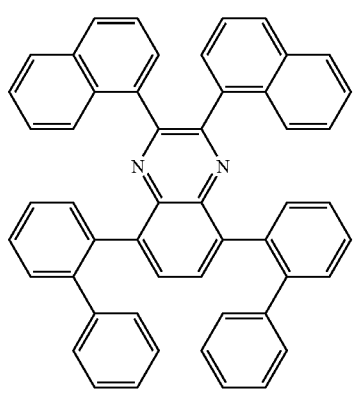
(46)
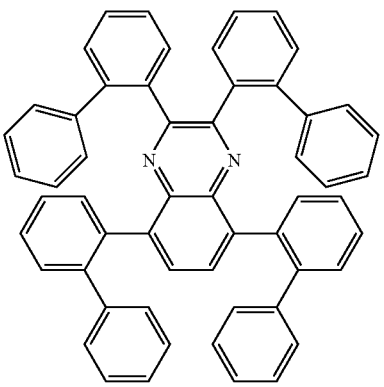
(49)
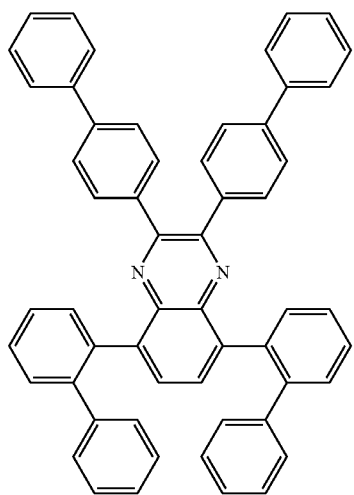
(47)
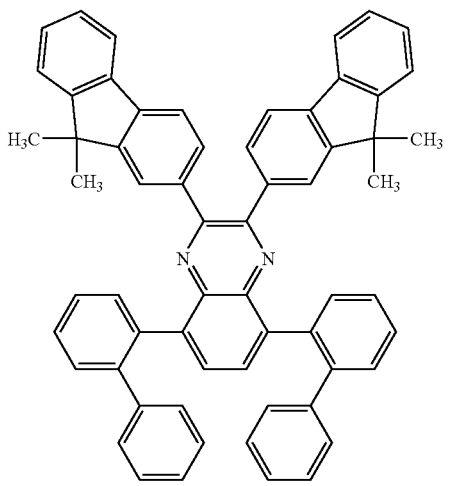
(50)

(51)
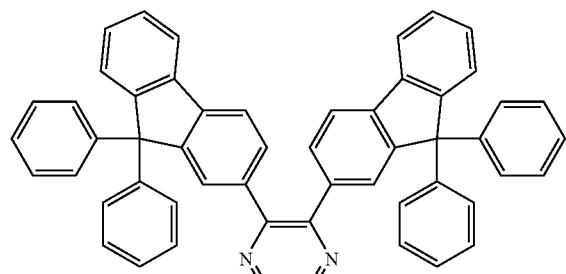
(52)
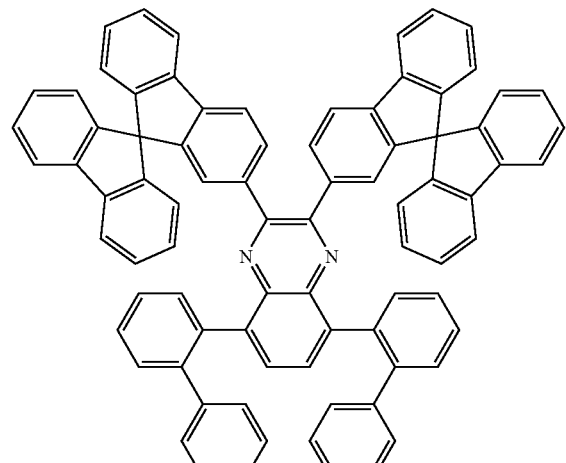
(53)
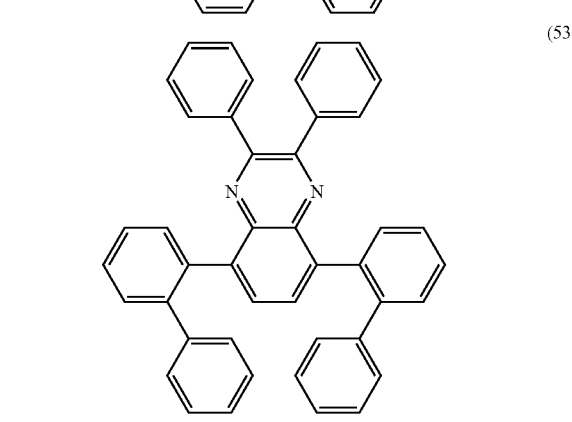
(54)
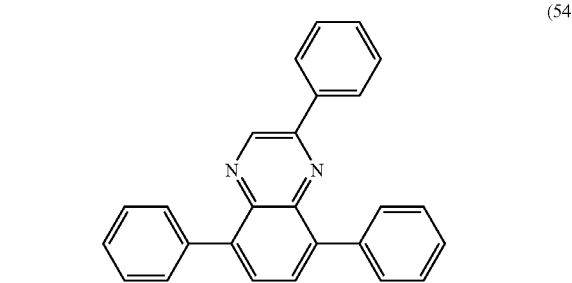
(55)
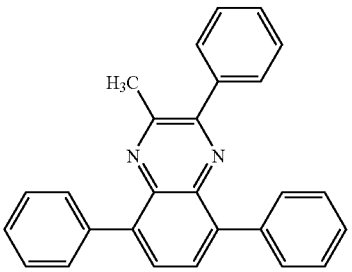
(56)
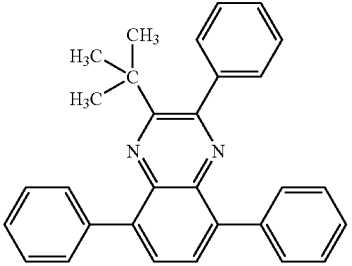
(57)
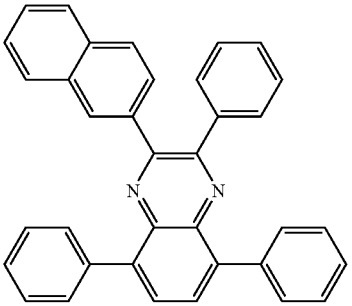
(58)
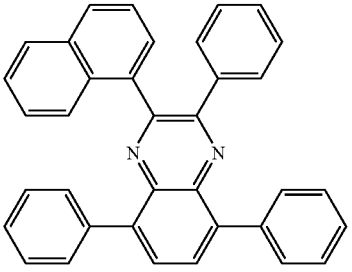
(59)
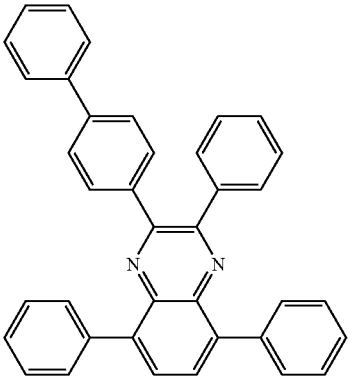

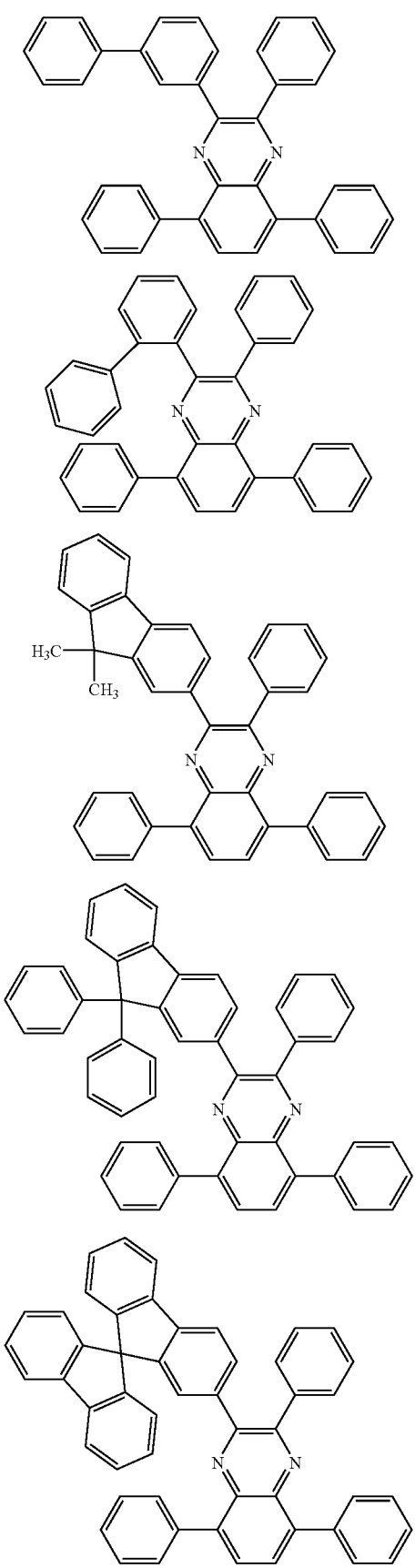
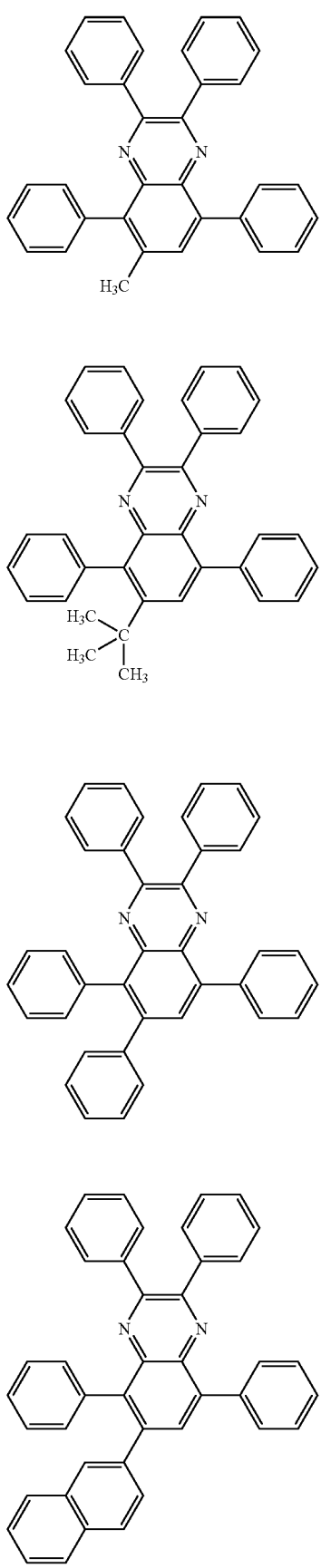

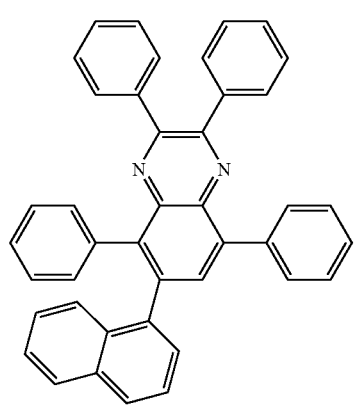 (69)
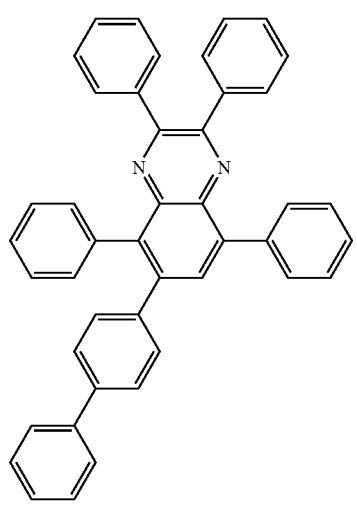 (70)
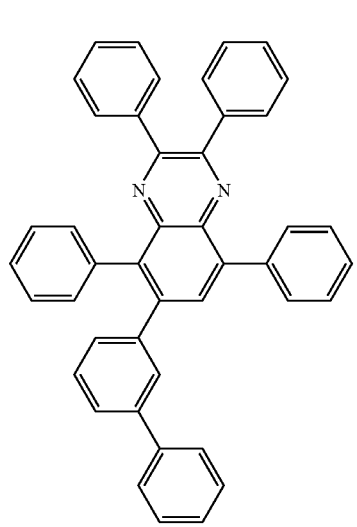 (71)
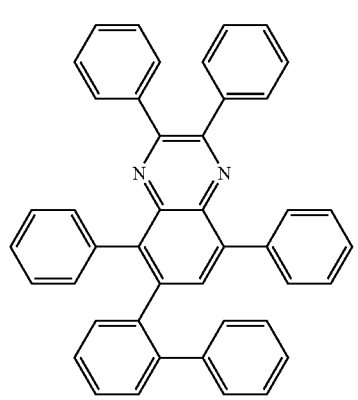 (72)
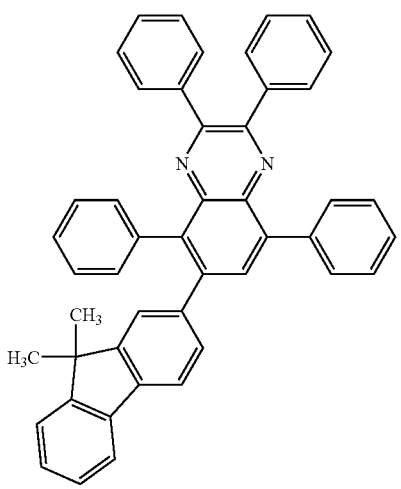 (73)
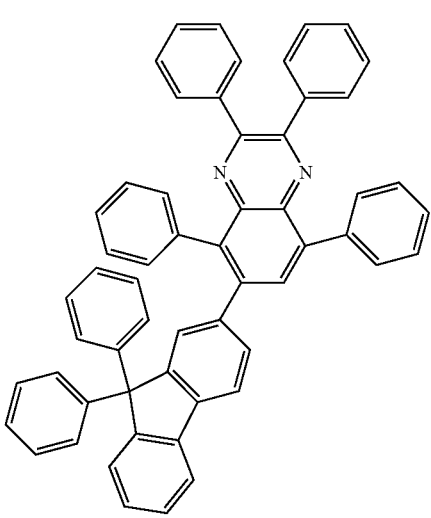 (74)

-continued
(75)
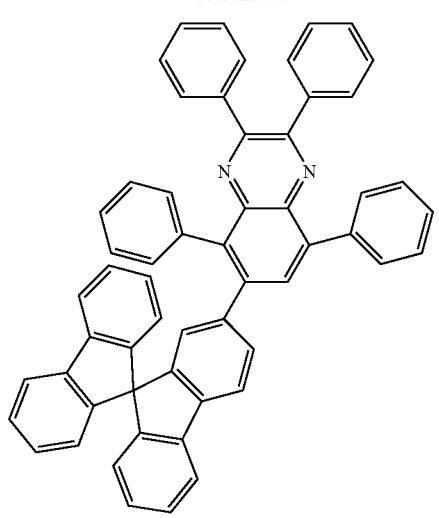
(76)
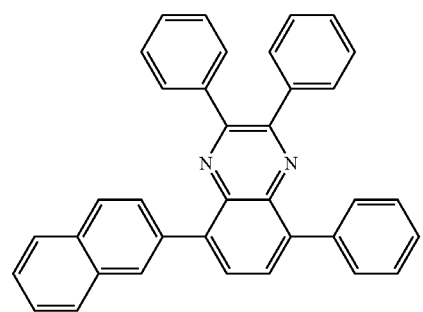
(77)
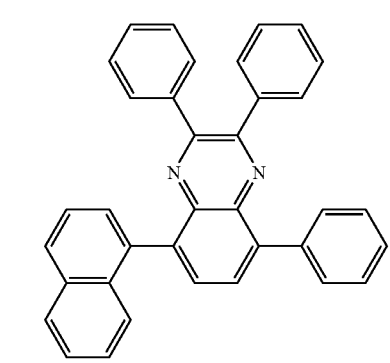
(78)
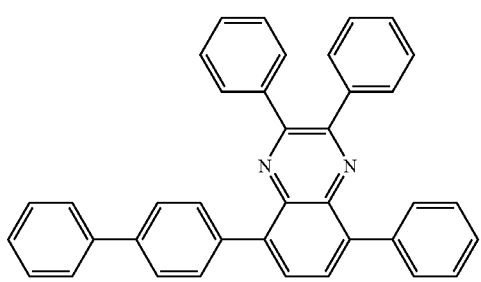
(79)
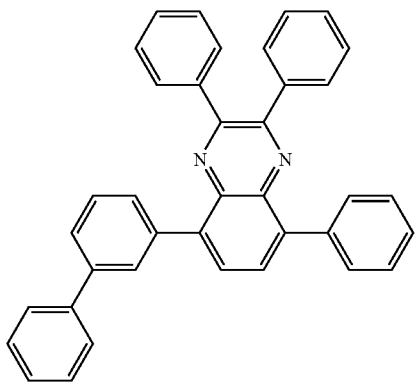
(80)
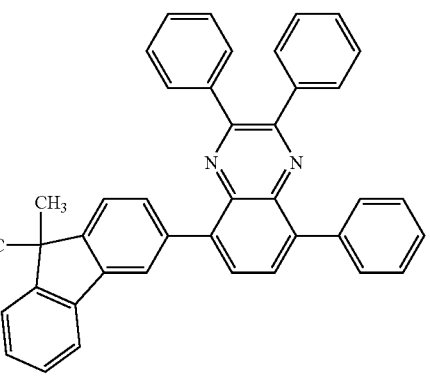
(81)
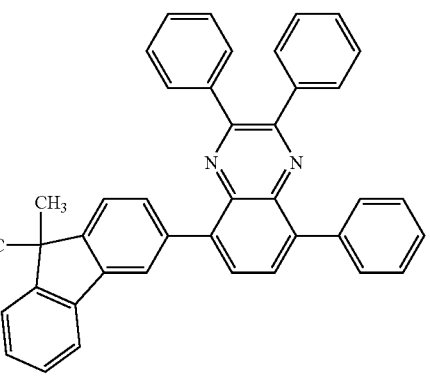
(82)
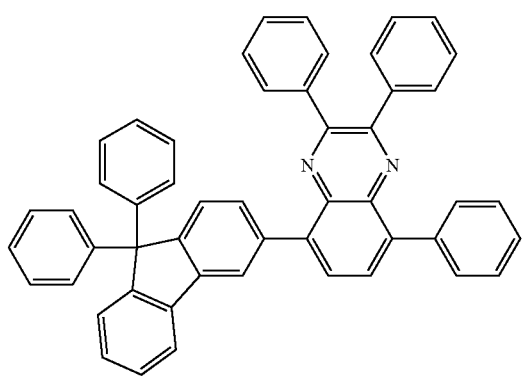

-continued (83)

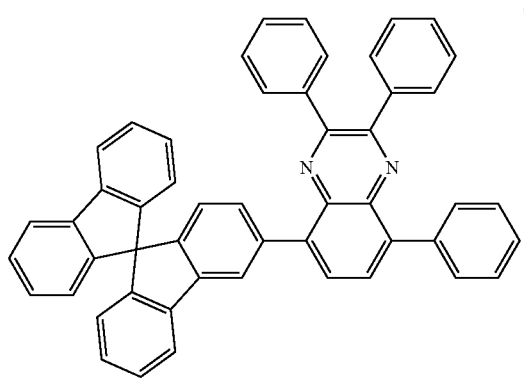

The quinoxaline derivative of the present invention as described above is excellent in electron-transporting property and thus very effective as an electron-transporting material in a light-emitting element and the like. In addition, the quinoxaline derivative of the present invention can also be used as a light-emitting material, and further, as a host material for a substance which emits phosphorescence without limitation to a substance which emits fluorescence.

(Embodiment Mode 2)

A synthesis method of the quinoxaline derivative of the present invention will be described hereinafter. Note that the quinoxaline derivative of the present invention is not limited to the one synthesized by the synthesis method described in this embodiment mode and may also be synthesized by other synthesis methods.

This embodiment mode will describe a quinoxaline derivative of the present invention represented by use of the following general formula (G1) as an example.

(G1)

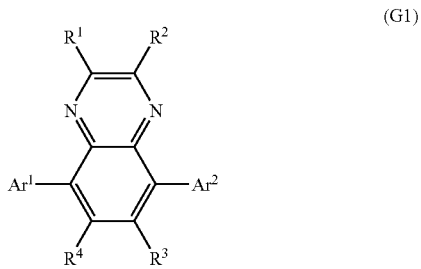

Note that in the general formula (G1), each of $R^1$ to $R^4$ represents hydrogen, an alkyl group having 1 to 4 carbon atoms, or an aryl group having 6 to 25 carbon atoms; and each of $Ar^1$ and $Ar^2$ represents an aryl group having 6 to 25 carbon atoms.

As shown in the following synthesis scheme (a-1), a halide of [2,1,3]-benzothiadiazole (compound A) in which 4 position and 7 position of [2,1,3]-benzothiadiazole are halogenated and an aryl boronic acid derivative or an aryl organic boron compound are coupled using a metal catalyst in the presence of a base, so that a 4,7-diaryl-[2,1,3]-benzothiadiazole derivative (compound B) can be obtained. Further, this 4,7-diaryl-[2,1,3]-benzothiadiazole derivative (compound B) is reduced using zinc or the like, so that a diamine compound (compound C) can be obtained.

Note that as a metal catalyst in coupling, a palladium catalyst such as palladium (II) acetate, tetrakis (triphenylphosphine) palladium (0), or bis (tricyclohexylphosphine) palladium (II) dichloride is preferable. Further, as a base, an inorganic base such as potassium carbonate or sodium carbonate, or an organic base such as metal alkoxide, e.g. sodium-tert-butoxide or potassium-tert-butoxide, or the like can be used.

(a-1)

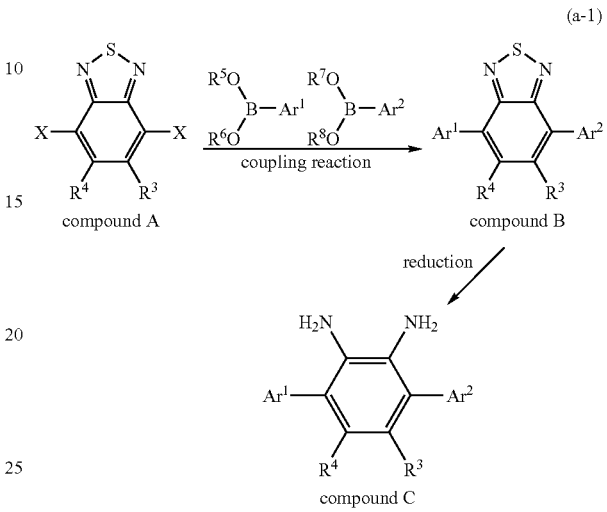

In the synthesis scheme (a-1), each of $R^3$ and $R^4$ represents hydrogen, an alkyl group having 1 to 4 carbon atoms, or an aryl group having 6 to 25 carbon atoms; and X represents a halogen group. In particular, bromine or iodine, which is highly reactive, is preferably used for X. In addition, each of $Ar^1$ and $Ar^2$ represents an aryl group having 6 to 25 carbon atoms; and each of $R^5$ to $R^8$ represents hydrogen or an alkyl group having 1 to 10 carbon atoms. Note that $R^5$ and $R^6$, and $R^7$ and $R^8$ may be coupled to form a ring.

In the above, when $Ar^1$ and $Ar^2$ are represented by different structural formulas, it is preferable that the 4,7-diaryl-[2,1,3]-benzothiadiazole derivative (compound B) be obtained by two-step-coupling. Further, it is preferable to use different halogen groups for X, that is, substituents of 4 position and 7 position in the halide of [2,1,3]-benzothiadiazole (compound A). Of course, when $Ar^1$ and $Ar^2$ are represented by the same structural formula, the 4,7-diaryl-[2,1,3]-benzothiadiazole derivative (compound B) can be obtained by one-step-coupling.

Next, as shown in the following synthesis scheme (a-2), the diamine compound (compound C) obtained according to the synthesis scheme (a-1) and an α-diketone derivative are condensed, so that a quinoxaline derivative of the present invention can be obtained. Note that in the synthesis scheme (a-2), each of $R^1$ to $R^4$ represents hydrogen, an alkyl group having 1 to 4 carbon atoms, or an aryl group having 6 to 25 carbon atoms; and each of $Ar^1$ and $Ar^2$ represents an aryl group having 6 to 25 carbon atoms.

(a-2)

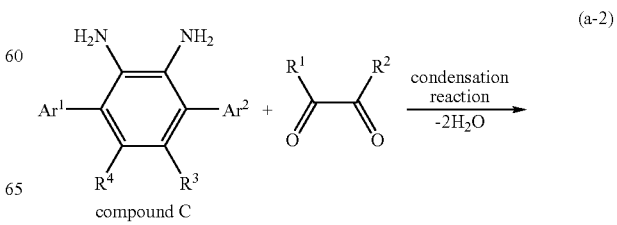

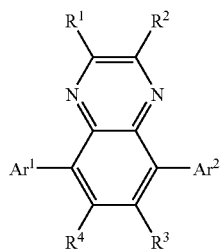

Note that the halide of benzothiadiazole (compound A) used in the synthesis scheme (a-1) can be obtained by, for example, a method shown in the following synthesis scheme (a-3). In the synthesis scheme (a-3), each of $R^3$ and $R^4$ represents hydrogen, an alkyl group having 1 to 4 carbon atoms, or an aryl group having 6 to 25 carbon atoms. Further, X represents a halogen group, preferably, bromine, which is easily halogenated. As shown in the synthesis scheme (a-3), benzothiadiazole is halogenated, so that the halide of benzothiadiazole (compound A) in which 4 position and 7 position of benzothiadiazole are halogenated can be obtained.

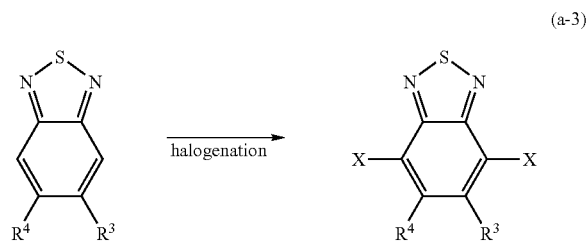

(a-3)

In this manner, the quinoxaline derivative of the present invention can be obtained. Note that the quinoxaline derivative of the present invention is excellent in electron-transporting property and thus very effective as an electron-transporting material in a light-emitting element and the like. In addition, the quinoxaline derivative can also be used as a light-emitting material. Further, the quinoxaline derivative can also be used as a host material for a substance which emits phosphorescence without limitation to a substance which emits fluorescence.

(Embodiment Mode 3)

A mode of a light-emitting element using the quinoxaline derivative of the present invention will be described with reference to FIG. 1. FIG. 1 shows a light-emitting element including a light-emitting layer 113 between a first electrode 101 and a second electrode 102. In addition to the light-emitting layer 113, a hole-injecting layer 111, a hole-transporting layer 112, an electron-transporting layer 114, and an electron-injecting layer 115 are provided between the first electrode 101 and the second electrode 102. These layers are stacked so that holes are injected from the first electrode 101 side and electrons are injected form the second electrode 102 side, when a voltage is applied so that potential of the first electrode 101 is higher than that of the second electrode 102.

In such a light-emitting element, holes injected from the first electrode 101 side and electrons injected from the second electrode 102 side are recombined in the light-emitting layer 113 to make a light-emitting substance be in an excited state. Then, when the light-emitting substance in the excited state returns to a ground state, light is emitted. As the light-emitting substance, any substance is acceptable as long as luminescence (electroluminescence) is obtained.

A substance for forming the light-emitting layer 113 is not particularly limited. The light-emitting layer 113 may be a layer formed only of a light-emitting substance; however, it is preferably a layer in which a light-emitting substance is mixed to be dispersed in a layer made of a substance (a host) having a larger energy gap than that of the light-emitting substance in the case where concentration quenching is caused. Thus, concentration quenching of a light-emitting substance can be prevented. Note that concentration quenching means a phenomenon in which light intensity is decreased as the concentration of light-emitting molecules gets higher. Further, an energy gap indicates an energy level difference between a lowest unoccupied molecular orbital (LUMO) level and a highest occupied molecular orbital (HOMO) level.

Further, the light-emitting substance is not particularly limited as described above. A substance capable of emitting light having a desired emission wavelength may be used. For example, when reddish light-emission is desired to be obtained, a substance that exhibits light-emission with a peak from 600 nm to 680 nm in the emission spectrum such as 4-dicyanomethylene-2-isopropyl-6-[2-(1,1,7,7-tetramethyl-julolidin-9-yl)ethenyl]-4H-pyran (abbreviation: DCJTI), 4-dicyanomethylene-2-methyl-6-[2-(1,1,7,7-tetramethylju-lolidin-9-yl)ethenyl]-4H-pyran (abbreviation: DCJT), 4-di-cyanomethylene-2-tert-butyl-6-[2-(1,1,7,7-tetramethyljulo-lidin-9-yl)ethenyl]-4H-pyran (abbreviation: DCJTB), periflanthene, or 2,5-dicyano-1,4-bis[2-(10-methoxy-1,1,7,7-tetramethyljulolidin-9-yl)ethenyl]benzene can be used.

When greenish light-emission is desired to be obtained, a substance that exhibits light-emission with a peak from 500 nm to 550 nm in the emission spectrum such as N,N'-dimethylquinacridone (abbreviation: DMQd), coumarin 6, coumarin 545T, tris(8-quinolinolato)aluminum (abbreviation: $Alq_3$), or N,N'-diphenylquinacridone (abbreviation: DPQd) can be used.

In addition, when bluish light-emission is desired to be obtained, a substance that exhibits light-emission with a peak from 420 nm to 500 nm in the emission spectrum such as 9,10-bis(2-naphthyl)-tert-butylanthracene (abbreviation: t-BuDNA), 9,9'-bianthryl, 9,10-diphenylanthracene (abbreviation: DPA), 9,10-bis(2-naphthyl)anthracene (abbreviation: DNA), bis(2-methyl-8-quinolinolato)-4-phenylpheno-lato-gallium (abbreviation: BGaq), bis(2-methyl-8-quinolinolato)-4-phenylphenolato-aluminum (abbreviation: BAlq), or 9-(4-{N-[4-(9-carbarizolyl)phenyl]-N-phenylamino}phenyl)-10-phenylanthracene (abbreviation: YGAPA) can be used.

A substance for putting the light-emitting substance into a dispersion state (hereinafter referred to as a host material) is not particularly limited. For example, a metal complex such as bis[2-(2-hydroxyphenyl)pyridinato]zinc (abbreviation: $Znpp_2$) or bis[2-(2-hydroxyphenyl)benzoxazolato]zinc (abbreviation: ZnBOX), or the like as well as an anthracene derivative such as 9,10-di(2-naphthyl)-2-tert-butylan-thracene (abbreviation: t-BuDNA) or 9-[4-(N-carbazolyl)] phenyl-10-phenylanthracene (abbreviation: CzPA) or a carbazole derivative such as 4,4'-bis(N-carbazolyl)biphenyl (abbreviation: CBP) can be used.

An anode material for forming the first electrode 101 is not particularly limited, and a metal, an alloy, an electric conductive compound, a mixture thereof, and the like, each of which has a high work function (work function of greater than or equal to 4.0 eV) are preferably used. As a specific example of such an anode material, indium tin oxide (abbreviation: ITO), indium tin oxide containing silicon oxide (abbreviation:

ITSO), and indium zinc oxide (abbreviation: IZO) formed by using a target in which 2 to 20 [wt %] zinc oxide (ZnO) is mixed into indium oxide can be given as an oxide of a metal material, and moreover, gold (Au), platinum (Pt), nickel (Ni), tungsten (W), chromium (Cr), molybdenum (Mo), iron (Fe), cobalt (Co), copper (Cu), palladium (Pd), a nitride of a metal material (for example, titanium nitride), or the like can also be used.

On the other hand, as a substance for forming the second electrode 102, a metal, an alloy, an electric conductive compound, a mixture thereof, and the like, each of which has a low work function (work function of less than or equal to 3.8 eV) can be used. As a specific example of such a cathode material, an element belonging to Group 1 or Group 2 of the periodic table, that is, an alkali metal such as lithium (Li) or cesium (Cs), an alkaline earth metal such as magnesium (Mg), calcium (Ca), or strontium (Sr), or an alloy containing them (Mg:Ag, Al:Li) can be used.

Further, a layer excellent in electron-injecting property is provided between the second electrode 102 and the light-emitting layer 113 so as to be stacked with the second electrode. Therefore, various conductive materials, which include a material such as Al, Ag, ITO, or ITSO mentioned as a material for the first electrode 101, can be used as the second electrode 102 regardless of a level of work function. Furthermore, a material particularly excellent in electron-injecting function is used for the electron-injecting layer 115, which will be described below, whereby a similar effect can be obtained.

Note that, in order to extract emitted light to the outside, one or both of the first electrode 101 and the second electrode 102 are preferably a transparent electrode such as ITO or an electrode formed to have a thickness of several nm to several tens of nm so that visible light can be transmitted. Further, the first electrode 101 and the second electrode 102 are formed by an evaporation method, a sputtering method, or the like using the anode material and the cathode material. The thickness is preferably 10 nm to 500 nm.

As shown in FIG. 1, the electron-transporting layer 114 is provided between the second electrode 102 and the light-emitting layer 113. Here, the electron-transporting layer 114 has a function of transporting electrons injected from the second electrode 102 to the light-emitting layer 113. In such a manner, the electron-transporting layer 114 is provided to separate the second electrode 102 from the light-emitting layer 113, whereby quenching of light-emission due to a metal can be prevented. Note that the electron-transporting layer 114 is a layer formed of the quinoxaline derivative of the present invention represented by any one of the general formulas (G1) to (G3). The quinoxaline derivative of the present invention is excellent in electron-transporting property and thus preferable as a material for forming the electron-transporting layer, whereby drive voltage of the light-emitting element can be reduced.

In the light-emitting element of the present invention, the electron-transporting layer 114 may be a layer including at least one of the quinoxaline derivatives of the present invention represented by the general formulas (G1) to (G3). This layer may be a layer in which the quinoxaline derivative of the present invention is mixed with another substance. The substance mixed with the quinoxaline derivative of the present invention (hereinafter referred to as a substance to be mixed) in the case of using such a mixed layer is preferably a substance excellent in electron-transporting property, particularly, a substance having electron mobility of greater than or equal to $1\times10^{-6}$ cm$^2$/Vs. Note that a substance having a high electron-transporting property means a substance having higher mobility of electrons than that of holes. In addition, the electron transporting layer 114 is not necessarily a single layer and may be a multilayer including two or more layers as long as a layer having the quinoxaline derivative of the present invention is included.

As a specific example of a substance to be mixed in the electron transporting layer 114, for example, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]-quinolinato)beryllium (abbreviation: BeBq$_2$), bis(2-methyl-8-quinolinolato)-4-phenylphenolato-aluminum (abbreviation: BAlq), bis[2-(2-hydroxyphenyl)-benzoxazolato]zinc (abbreviation: Zn(BOX)$_2$), or bis[2-(2-hydroxyphenyl)-benzothiazolato]zinc (abbreviation: Zn(BTZ)$_2$) can be used.

Further, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), 4,4-bis(5-methylbenzoxazol-2-yl)stilbene (abbreviation: BzOs), or the like can be used.

As shown in FIG. 1, the hole-transporting layer 112 may be provided between the first electrode 101 and the light-emitting layer 113. The hole-transporting layer 112 has a function of transporting holes injected from the first electrode 101 side to the light-emitting layer 113. In such a manner, the hole-transporting layer 112 is provided to separate the first electrode 101 from the light-emitting layer 113, whereby quenching of light-emission due to a metal included in the first electrode 101 can be prevented. The hole-transporting layer 112 is preferably formed of a substance having a high hole-transporting property, particularly, a substance having hole mobility of greater than or equal to $1\times10^{-6}$ cm$^2$/Vs. Note that a substance having a high hole-transporting property means a substance having higher mobility of holes than that of electrons.

As a specific example of a substance that can be used for forming the hole-transporting layer 112, 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), or the like can be used.

Further, 1,3,5-tris[N,N-di(m-tolyl)amino]benzene (abbreviation: m-MTDAB), 4,4',4"-tris(N-carbazolyl)triphenylamine (abbreviation: TCTA), phthalocyanine (abbreviation: H$_2$Pc), copper phthalocyanine (abbreviation: CuPc), vanadyl phthalocyanine (abbreviation: VOPc), or the like can be used. Further, the hole-transporting layer 112 may be a multilayer formed by combining at least two layers formed of the above substance or a mixed layer formed by mixing at least two of the above substances.

Note that the hole-transporting layer 112 may also be formed using a bipolar substance, in addition to the above substances. The bipolar substance refers to the following substance: when mobility of either carrier of an electron or a hole is compared with mobility of the other carrier, a value of a ratio of one carrier mobility to the other carrier mobility is 100 or less, preferably 10 or less. As for the bipolar substance, for example, 2,3-bis(4-diphenylaminophenyl)quinoxaline (abbreviation: TPAQn); 2,3-bis{4-[N-(1-naphthyl)-N-phenylamino]phenyl}-dibenzo[f,h]quinoxaline (abbreviation: NPADiBzQn); and the like can be given. In particular, it is preferable to use a substance of which hole mobility is greater than or equal to $1\times10^{-6}$ cm$^2$/Vs among the bipolar substances for the hole-transporting layer 112.

In addition, when the electron-transporting layer 114 is a mixed layer of the quinoxaline derivative of the present invention and another substance, the electron-transporting layer 114 may also be formed using a bipolar substance, in addition to the above substances which are mixed with the quinoxaline of the present invention, that is, a substance to be mixed. In particular, among the bipolar substances, a substance having electron mobility of greater than or equal to $1\times10^{-6}$ cm$^2$/Vs is preferably used.

As shown in FIG. 1, the hole-injecting layer 111 may be provided between the first electrode 101 and the hole-transporting layer 112. Here, the hole-injecting layer 111 has a function of assisting injection of holes from the first electrode 101 to the hole-transporting layer 112. By providing the hole-injecting layer 111, an ionization potential difference between the first electrode 101 and the hole-transporting layer 112 is relieved; thus, holes are easily injected. The hole-injecting layer 111 is preferably formed using a substance of which ionization potential is lower than that of a substance forming the hole-transporting layer 112 and higher than that of a substance forming the first electrode 101 or using a substance of which energy band curves by being provided as a thin film having a thickness of 1 nm to 2 nm between the hole-transporting layer 112 and the first electrode 101.

As for a specific example of a substance that can be used to form the hole-injecting layer 111, a phthalocyanine-based compound such as phthalocyanine (abbreviation: H$_2$Pc) or copper phthalocyanine (CuPc), a high molecular material such as poly(ethylenedioxythiophene)/poly(styrenesulfonic acid) solution (PEDOT/PSS), and the like can be given. In other words, such a substance is selected that ionization potential of the hole-injecting layer 111 is relatively lower than that of the hole-transporting layer 112, to form the hole-injecting layer 111.

In addition, the electron-injecting layer 115 is preferably provided between the second electrode 102 and the electron-transporting layer 114 as shown in FIG. 1. Here, the electron-injecting layer 115 has a function of assisting injection of electrons from the second electrode 102 to the electron-transporting layer 114. By providing the electron-injecting layer 115, an electron affinity difference between the second electrode 102 and the electron-transporting layer 114 is relieved; thus, electrons are easily injected. The electron-injecting layer 115 is preferably formed using a substance of which electron affinity is higher than that of a substance forming the electron-transporting layer 114 and lower than that of a substance forming the second electrode 102 or using a substance of which energy band curves by being provided as a thin film having a thickness of 1 nm to 2 nm between the electron-transporting layer 114 and the second electrode 102.

The following can be given as a specific example of a substance that can be used to form the electron-injecting layer 115: an inorganic material such as an alkali metal, an alkaline earth metal, a fluoride of an alkali metal, a fluoride of an alkaline earth metal, an oxide of an alkali metal, or an oxide of an alkaline earth metal. In addition to the inorganic material, a substance that can be used to form the electron-transporting layer 114 such as BPhen, BCP, p-EtTAZ, TAZ, or BzOs can also be used as a substance forming the electron-injecting layer 115 by appropriately selecting a substance of which electron affinity is relatively higher than that of a substance forming the electron-transporting layer 114 from these substances.

In the light-emitting element according to the present invention described above, each of the hole-injecting layer 111, the hole-transporting layer 112, the light-emitting layer 113, the electron-transporting layer 114, and the electron-injecting layer 115 may be formed by any of an evaporation method, an ink-jet method, a coating method, and the like. Further, a hole-generating layer may be provided instead of the hole-injecting layer 111. Alternatively, an electron-generating layer may be provided instead of the electron-injecting layer 115. Note that the hole-generating layer is a layer which generates holes. The hole-generating layer can be formed by mixing at least one substance selected from substances having higher mobility of holes than that of electrons and bipolar substances, and a substance exhibiting an electron-accepting property with respect to these substances.

Here, as for the substance having higher mobility of holes than that of electrons, the similar substance to the substance that can be used to form the hole-transporting layer 112 can be used. Moreover, as for the bipolar substance, the above bipolar substance such as TPAQn can be used. In particular, it is preferable to use a substance having a triphenylamine structure in a skeleton among the substances having higher mobility of holes than that of electrons and the bipolar substances. Holes can be generated more easily by using the substance having a triphenylamine structure in a skeleton. Further, as for the substance that exhibits an electron-accepting property, it is preferable to use a compound such as molybdenum oxide, vanadium oxide, ruthenium oxide, or rhenium oxide, or an organic compound such as 2,3,5,6-tetrafluoro-7,7,8,8,8-tetracyanoquinodimethane (abbreviation: F$_4$-TCNQ).

In such a hole-generating layer, increase in film thickness does not cause increase in drive voltage; therefore, an optical design which utilizes a microcavity effect and a light interference effect is possible by adjusting the thickness of the hole-generating layer. Therefore, a light-emitting element with high quality which has favorable color purity and fewer color changes due to a viewing angle can be formed. In addition, a film thickness can be set so as to prevent short circuit of the first electrode 101 and the second electrode 102 due to affection of minute residue remaining on the surface of the electrode or the uneven surface of the first electrode 101 generated in deposition.

The electron-generating layer is a layer which generates electrons. The electron-generating layer can be formed by mixing at least one substance selected from substances having higher mobility of electrons than that of holes and bipolar substances, and a substance which exhibits an electron-donating property with respect to the these substances. As a substance selected from the substances having higher mobility of electrons than that of holes, a substance similar to the substance which can be used to form the electron-transporting layer 114 can be used. As a bipolar substance, the foregoing bipolar substance such as TPAQn can be used.

As the substance having an electron-donating property, a substance selected from an alkali metal and an alkaline earth metal, such as lithium (Li), calcium (Ca), sodium (Na), potassium (K), or magnesium (Mg) can be used. At least one substance selected from alkali metal oxide, alkaline earth metal oxide, alkali metal nitride, and alkaline earth metal nitride, such as lithium oxide (Li$_2$O), calcium oxide (CaO), sodium oxide (Na$_2$O), potassium oxide (K$_2$O), or magnesium oxide (MgO) can be used as a substance having an electron-donating property. In addition, a fluoride such as alkali metal fluoride or alkaline earth metal fluoride, such as lithium fluoride (LiF), cesium fluoride (CsF), or calcium fluoride (CaF$_2$) can be used.

The quinoxaline derivative of the present invention can also be used as a substance for putting the light-emitting substance into a dispersion state (that is, a host material). In such a case, the quinoxaline derivative of the present invention is not necessarily required to be used for the electron-transporting layer 114, and a substance excellent in electron-transporting property may be used for the electron-transporting layer 114. Note that even if the light-emitting substance is a substance exhibiting blue light-emission, the quinoxaline derivative of the present invention can be preferably used as a host material. In this manner, by using the quinoxaline derivative of the present invention, a light-emitting element with low drive voltage can be obtained.

In addition, the quinoxaline derivative of the present invention can be used as a host material for various light-emitting substances which emit phosphorescence. In such a case, it is preferable to use the quinoxaline derivative of the present invention as a host material particularly for a substance which emits red phosphorescence, such as bis[2-(2'-benzo[4,5-α]thienyl)pyridinato-N,C$^{3'}$]iridium(III) acetylacetonate (abbreviation: Ir(btp)$_2$(acac)), bis(1-phenylisoquinolinato-N, C$^{2'}$)iridium(III)acetylacetonate (abbreviation: Ir(piq)$_2$ (acac)), or (2,3,7,8,12,13,17,18-octaetyl-21H,23H-porphyrinato)platinum (abbreviation: PtOEP).

Further, the quinoxaline derivative of the present invention can also be used as a light-emitting substance. In such a case, the quinoxaline derivative of the present invention is not necessarily required to be used for other layers. Even when the quinoxaline derivative of the present invention is used for a light-emitting substance, the light-emitting layer 113 may be a layer formed of only the light-emitting substance, or a layer in which the light-emitting substance is mixed to be dispersed in a layer made of a substance (a host) having a larger energy gap than that of the light-emitting substance in the case where concentration quenching is caused.

(Embodiment Mode 4)

Figure 2A:
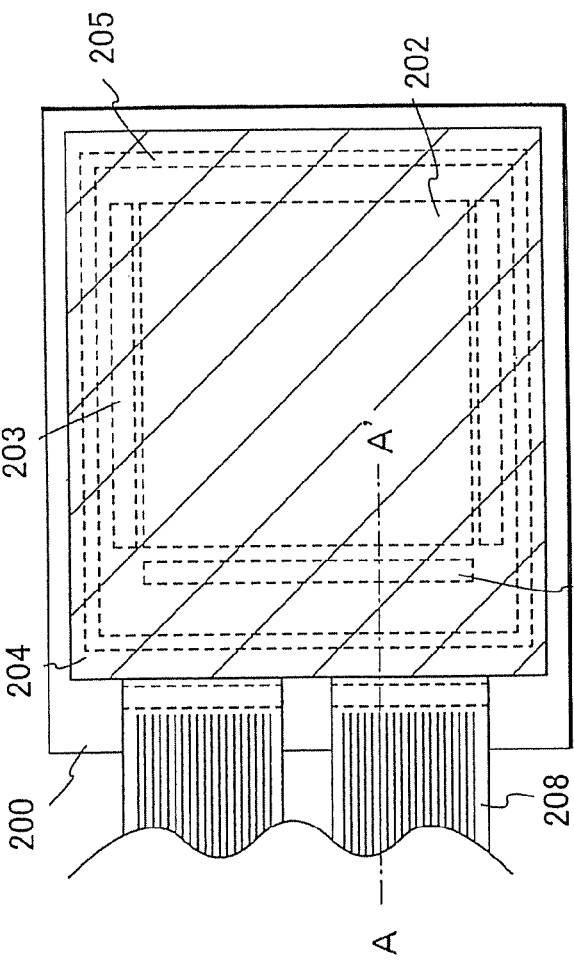
FIGS. 2A and 2B are views of a light-emitting device using a light-emitting element according to the present invention.
Figure 2B:
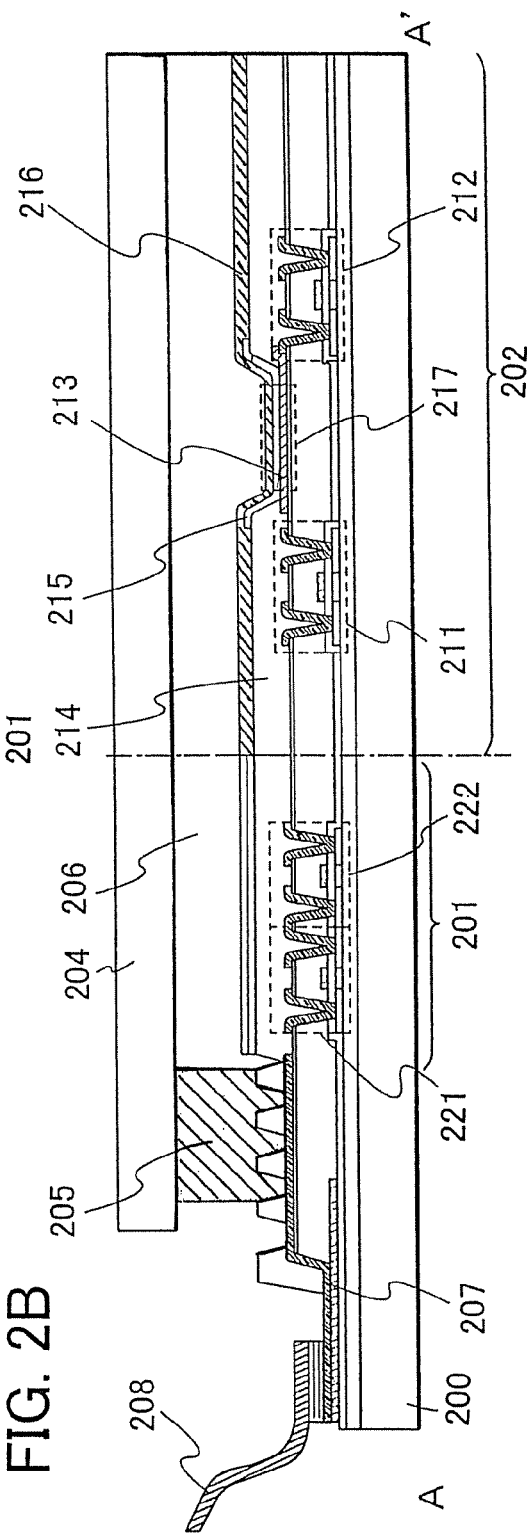

In this embodiment mode, a light-emitting device to which the present invention is applied will be described with reference to FIGS. 2A and 2B. FIG. 2A is a top view showing a light-emitting device, and FIG. 2B is a cross-sectional view taken along a line A-A' of FIG. 2A. In FIGS. 2A and 2B, the same portions are denoted by the same reference numerals. In FIG. 2A, reference numeral 200 denotes a substrate; 201 enclosed by a dot line, a driver circuit portion (a source driver circuit); 202, a pixel portion; 203 enclosed by a dot line similarly to 201, a driver circuit portion (a gate driver circuit); 204, a sealing substrate; and 205, a sealing material.

Reference numeral 207 denotes a wiring for transmitting a signal input to the source driver circuit 201 or the gate driver circuit 203, and receives signals such as a video signal, a clock signal, a start signal, and a reset signal from an FPC (flexible printed circuit) 208 that is to be an external input terminal. Although only the FPC 208 is shown here, a printed wiring board (PWB) may be attached to this FPC. The light-emitting device of the present invention includes not only a light-emitting device itself but also a light-emitting device provided with an FPC or a PWB.

Next, a cross-sectional structure will be described with reference to FIG. 2B. The driver circuit portion and the pixel portion are formed over the substrate 200, and the source driver circuit 201 that is the driver circuit portion and the pixel portion 202 are shown here. The source driver circuit 201 is formed of a CMOS circuit in which an n-channel thin film transistor 221 and a p-channel thin transistor 222 are combined. Further, the driver circuit formed using a thin film transistor may be a known CMOS circuit as described above, a PMOS circuit, or an NMOS circuit. In this embodiment mode, an example in which the driver circuit is formed over the same substrate as the pixel portion is shown; however, this is not always needed, and the driver circuit can also be formed outside the substrate.

The pixel portion 202 is formed of a plurality of pixels each including a switching thin film transistor 211, a current control thin film transistor 212, and a first electrode 213 electrically connected to a drain of the current control thin film transistor 212. Note that an insulator 214 is formed to cover edge portions of the first electrode 213. Further, in order to favorably form a layer 215 including a light-emitting substance, which will be formed later, the insulator 214 is preferably formed to have a curved surface having curvature in an upper edge portion or a lower edge portion, or both of upper and lower edge portions.

For example, in the case where positive type photosensitive acrylic is used as a material of the insulator 214, it is preferable that only an upper edge portion of the insulator 214 have a curved surface with a curvature radius (0.2 μm to 3 μm). In addition, as the insulator 214, any of a negative type photosensitive insulator that is to be insoluble in an etchant by light or a positive type photosensitive insulator that is to be soluble in an etchant by light can be used. Furthermore, as a material of the insulator 214, an inorganic material such as silicon oxide or silicon oxynitride can be used in addition to an organic material.

Over the first electrode 213, the layer 215 including a light-emitting substance and a second electrode 216 are formed. A light-emitting element 217 including the first electrode 213, the layer 215 including a light-emitting substance, and the second electrode 216 is a light-emitting element including the quinoxaline derivative of the present invention. As long as at least one of the quinoxaline derivatives of the present invention represented by the general formulas (G1) to (G3) is used for the layer 215 including a light-emitting substance, a stacked layer structure is not particularly limited. Note that the materials described in Embodiment Mode 3 can be selectively and appropriately used for the first electrode 213, the layer 215 including a light-emitting substance, and the second electrode 216.

The sealing substrate 204 is attached to the substrate 200 with the use of the sealing material 205, whereby a structure in which the light-emitting element 217 is provided in a space 206 surrounded by the substrate 200, the sealing substrate 204, and the sealing material 205 is obtained. The space 206 includes a structure that is filled with the sealing material 205, in addition to a structure that is filled with an inert gas (such as nitrogen or argon).

As for the sealing material 205, an epoxy based resin is preferably used. Further, preferably, materials used for the sealing material 205 do not transmit moisture and oxygen as much as possible. As for a material used for the sealing substrate 204, in addition to a glass substrate and a quartz substrate, a plastic substrate made from FRP (Fiberglass-Reinforced Plastics), PVF (polyvinyl fluoride), polyester, acrylic, or the like can be used. As described above, a light-emitting device can be manufactured.

In the case where both the first electrode 213 and the second electrode 216 are made of a substance having a light-transmitting property, light-emission can be extracted from both the first electrode 213 side and the second electrode 216 side. In the case where only the second electrode 216 is made of a substance having a light-transmitting property, light-emission can be extracted only from the second electrode 216 side. In this case, the first electrode 213 is preferably made of a material having high reflectivity. Alternatively, a film made of a material having high reflectivity (a reflective film) is preferably provided in a lower part of the first electrode 213. In the case where only the first electrode 213 is made of a substance having a light-transmitting property, light-emission can be extracted only from the first electrode 213 side. In this case, the second electrode 216 is preferably made of a material having high reflectivity. Alternatively, a reflective film is preferably provided in an upper part of the second electrode 216.

In the light-emitting element 217, the layer 215 including a light-emitting substance may be stacked so as to make the light-emitting element work when applying a voltage so that potential of the second electrode 216 is higher than that of the first electrode 213. Alternatively, the layer 215 including a light-emitting substance may be stacked so as to make the light-emitting element work when applying a voltage so that potential of the second electrode 216 is lower than that of the first electrode 213.

By using the light-emitting element with low drive voltage including the quinoxaline derivative of the present invention, power consumption of the light-emitting device of the present invention can be reduced. This embodiment mode can be appropriately combined with any of Embodiment Modes 1 to 3 and the following embodiment modes.

(Embodiment Mode 5)

Figure 3A:
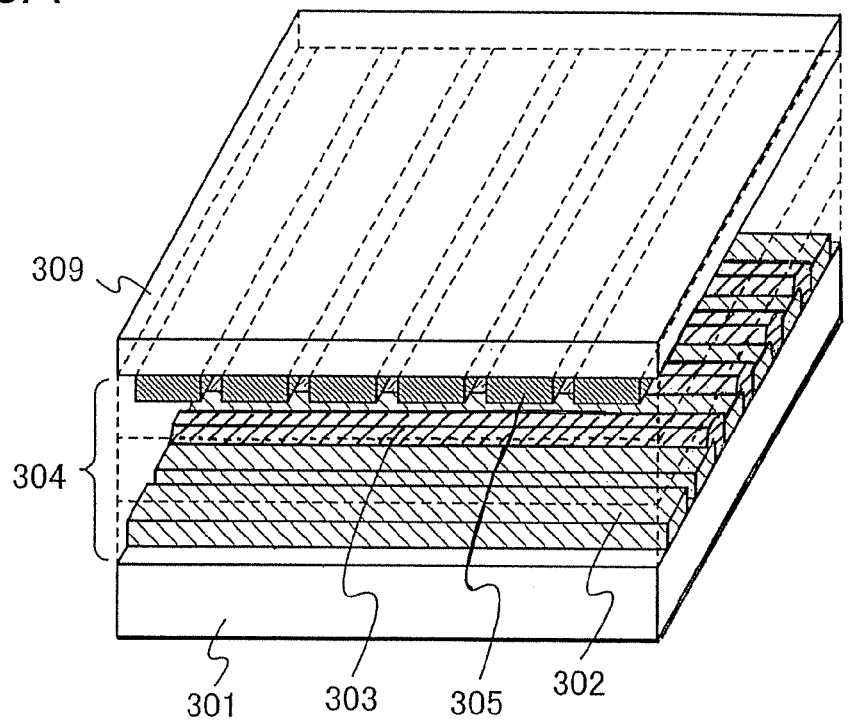
FIGS. 3A and 3B are views of a light-emitting device using a light-emitting element according to the present invention.
Figure 3B:
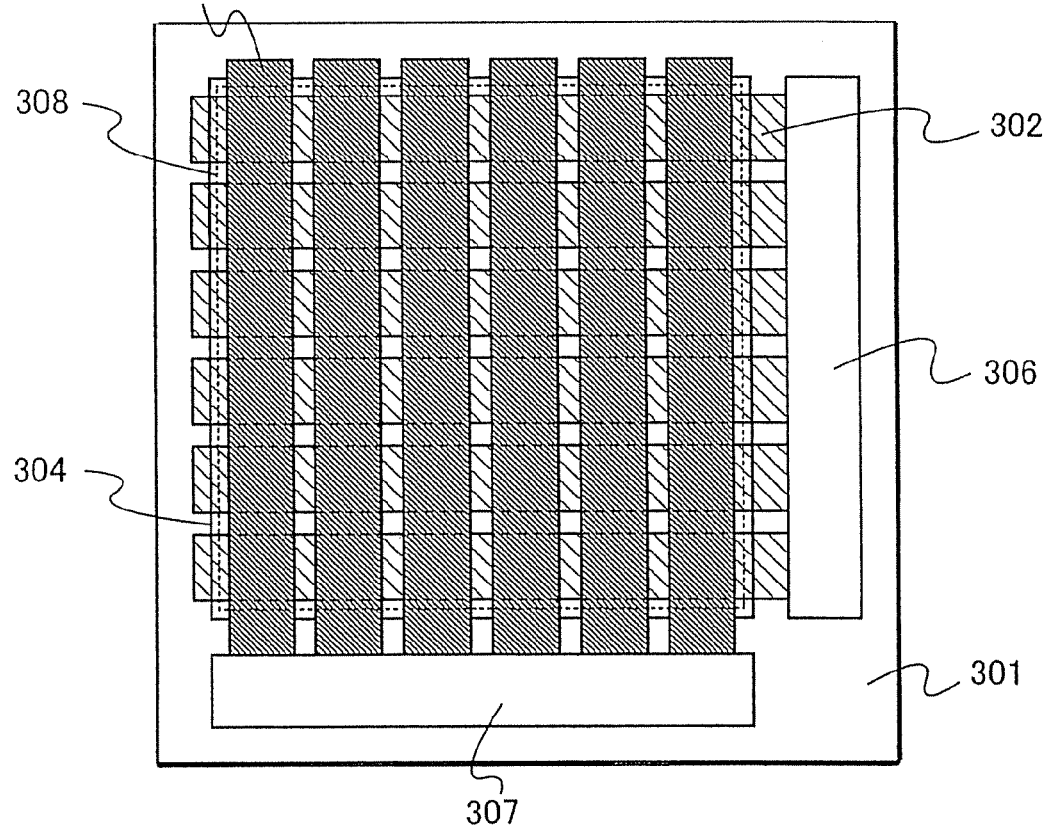

In Embodiment Mode 4, the active-matrix type light-emitting device to which the present invention is applied is shown. In this embodiment mode, a passive-matrix type light-emitting device to which the present invention is applied will be described with reference to FIGS. 3A and 3B. FIGS. 3A and 3B are respectively a perspective view and a top view of a passive-matrix type light-emitting device to which the preset invention is applied. Note that FIG. 3A is a perspective view corresponding to a portion enclosed by a dot line 308 of FIG. 3B. In FIGS. 3A and 3B, the same portions are denoted by using the same reference numerals. In FIG. 3A, a plurality of first electrodes 302 are provided in parallel over a first substrate 301.

An edge portion of each of the first electrodes 302 is covered with a partition layer 303. An edge portion of the first electrode 302 that is positioned in the front is also covered with the partition layer 303; however, the partition layer 303 in that position is not shown in FIG. 3A in order to clearly show the arrangement of the first electrodes 302 and the partition layers 303 provided over the first substrate 301. A plurality of second electrodes 305 are provided in parallel over the first electrodes 302 so as to intersect with the first electrodes 302. A layer 304 including a light-emitting substance is provided between the first electrodes 302 and the second electrodes 305.

In portions where the first electrodes 302 and the second electrodes 305 are intersected with each other, the layer 304 including a light-emitting substance is interposed therebetween, whereby a light-emitting element of the present invention is constituted. As long as at least one of the quinoxaline derivatives of the present invention represented by the general formulas (G1) to (G3) is used for the layer 304 including a light-emitting substance, a stacked layer structure is not particularly limited. The materials described in Embodiment Mode 3 can be selectively and appropriately used for the first electrodes 302, the layer 304 including a light-emitting substance, and the second electrodes 305. Further, a second substrate 309 is provided over the second electrodes 305.

As shown in FIG. 3B, the first electrodes 302 are connected to a first driver circuit 306, and the second electrodes 305 are connected to a second driver circuit 307. Then, a light-emitting element of the present invention, which is selected by a signal from the first driver circuit 306 and the second driver circuit 307, emits light. Light-emission is extracted to outside through the first electrodes 302 and/or the second electrodes 305. After that, an image is projected by combining light-emission from a plurality of light-emitting elements. In FIG. 3B, the partition layer 303 and the second substrate 309 are not shown in order to clearly show the arrangement of the first electrodes 302 and the second electrodes 305.

In the case where both the first electrodes 302 and the second electrodes 305 are made of a substance having a light-transmitting property, light-emission can be extracted from both the first electrode 302 side and the second electrode 305 side. In the case where only the second electrodes 305 are made of a substance having a light-transmitting property, light-emission can be extracted only from the second electrode 305 side. In this case, the first electrodes 302 are preferably made of a substance having high reflectivity. Alternatively, a film made of a material having high reflectivity (a reflective film) is preferably provided in a lower part of the first electrodes 302. In the case where only the first electrodes 302 are made of a substance having a light-transmitting property, light-emission can be extracted only from the first electrode 302 side. In this case, the second electrodes 305 are preferably made of a material having high reflectivity. Alternatively, a reflective film is preferably provided in an upper part of the second electrodes 305. The partition layer 303 can be formed using the same material as that of the insulator 214 described in Embodiment Mode 4.

By using a light-emitting element with low drive voltage including the quinoxaline derivative of the present invention, power consumption of the light-emitting device of the present invention can be reduced. This embodiment mode can be appropriately combined with any of Embodiment Modes 1 to 3 and the following embodiment modes.

(Embodiment Mode 6)

In this embodiment mode, various electronic appliances will be described, each of which is completed by using a light-emitting device having the light-emitting element of the present invention. When the light-emitting element with low drive voltage including the quinoxaline derivative of the present invention is used for a light-emitting device of the present invention, electronic appliances with low power consumption can be provided.

As electronic appliances manufactured by using the light-emitting device of the present invention, the following can be given: televisions, cameras such as video cameras or digital cameras, goggle type displays (head mounted display), navigation systems, audio reproducing devices (car audio, audio component, or the like), laptop personal computers, game machines, portable information terminals (mobile computer, cellular phone, portable game machine, electronic book, or the like), image reproducing devices including a recording medium (specifically, a device reproducing a recording medium such as a digital versatile disc (DVD) and including a display device which can display the image), and the like. Specific examples of some electronic appliances will be described with reference to FIGS. 4A to 4E. An electronic appliance using the light-emitting device of the present invention is not limited to these illustrated specific examples.

Figure 4A:
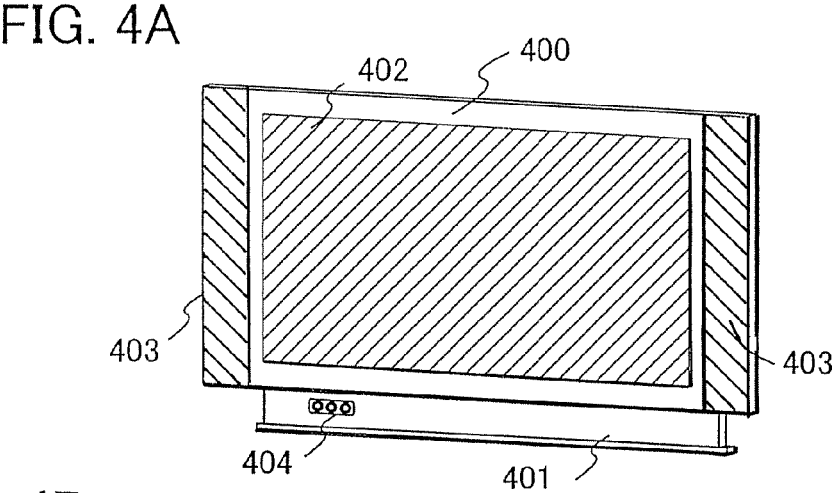
FIGS. 4A to 4E are views of electronic appliances using a light-emitting element according to the present invention.

FIG. 4A shows a display device, which includes a chassis 400, a supporting base 401, a display portion 402, speaker portions 403, a video input terminal 404, and the like. The display device is manufactured by using a light-emitting device that is formed by the present invention for the display portion 402. Note that the display device includes all devices for information display, such as for personal computers, for receiving TV broadcastings, for displaying advertisements, and the like. The light-emitting element of the present invention is provided in the display portion 402. A layer including a light-emitting substance of the light-emitting element includes at least one of the quinoxaline derivatives of the present invention represented by the general formulas (G1) to (G3). Therefore, by using the light-emitting element of the present invention, a display device with low power consumption can be obtained.

Figure 4B:
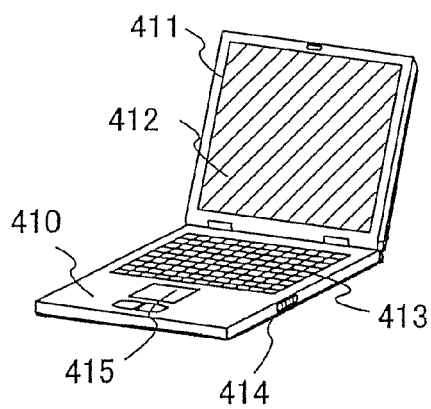

FIG. 4B shows a laptop personal computer, which includes a main body 410, a chassis 411, a display portion 412, a keyboard 413, an external connecting port 414, a pointing device 415, and the like. The light-emitting element of the present invention is provided in the display portion 412. A layer including a light-emitting substance of the light-emitting element includes at least one of the quinoxaline derivatives of the present invention represented by the general formulas (G1) to (G3). Therefore, by using the light-emitting element of the present invention, a laptop personal computer with low power consumption can be obtained.

Figure 4C:
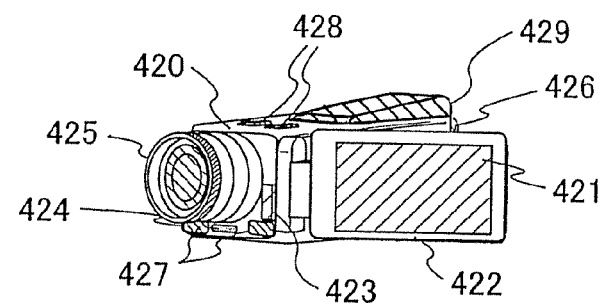

FIG. 4C shows a video camera, which includes a main body 420, a display portion 421, a chassis 422, an external connecting port 423, a remote control receiving portion 424, an image receiving portion 425, a battery 426, an audio input portion 427, operation keys 428, an eye piece portion 429, and the like. The light-emitting element of the present invention is provided in the display portion 421. A layer including a light-emitting substance of the light-emitting element includes at least one of the quinoxaline derivatives of the present invention represented by the general formulas (G1) to (G3). Therefore, by using the light-emitting element of the present invention, a video camera with low power consumption can be obtained.

Figure 4D:
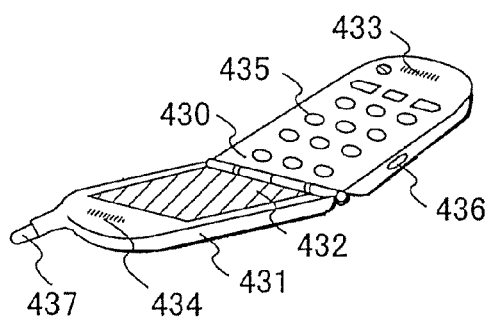

FIG. 4D shows a cellular phone, which includes a main body 430, a chassis 431, a display portion 432, an audio input portion 433, an audio output portion 434, operation keys 435, an external connecting port 436, an antenna 437, and the like. The light-emitting element of the present invention is provided in the display portion 432. A layer including a light-emitting substance of the light-emitting element includes at least one of the quinoxaline derivatives of the present invention represented by the general formulas (G1) to (G3). Therefore, by using the light-emitting element of the present invention, a cellular phone with low power consumption can be obtained.

Figure 4E:
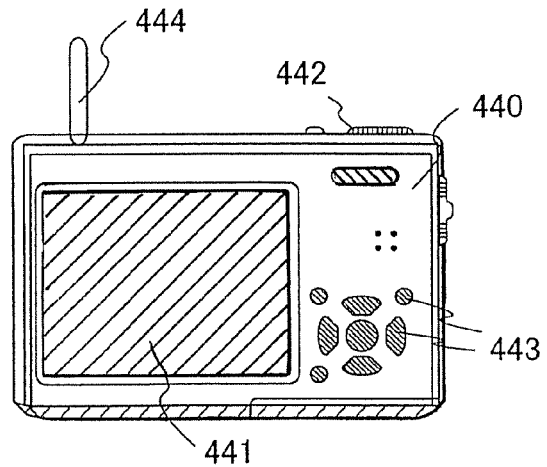

FIG. 4E shows a digital camera, which includes a main body 440, a display portion 441, a shutter button 442, operation keys 443, an antenna 444, an imaging portion, and the like. Note that FIG. 4E is a view from the display portion 441 side, and the imaging portion is not illustrated. In the digital camera of the present invention, the display portion 441 may function as a display medium such as a television receiver by receiving signals such as a video signal and an audio signal from the antenna 444. Note that a speaker, an operation switch, and the like may be appropriately provided when the display portion 441 serves as a display medium. The light-emitting element of the present invention is provided in the display portion 441. A layer including a light-emitting substance of the light-emitting element includes at least one of the quinoxaline derivatives of the present invention represented by the general formulas (G1) to (G3). Therefore, by using the light-emitting element of the present invention, a digital camera with low power consumption can be obtained.

As described above, the application range of the present invention is extremely wide, and the present invention can be used in display devices of various fields. Further, the electronic appliance of this embodiment mode can be appropriately combined with any structure of Embodiment Modes 1 to 5.

(Embodiment 1)

A synthesis example of the quinoxaline derivative of the present invention will be described below. Note that the present invention is not limited by this synthesis example.

SYNTHESIS EXAMPLE 1

A synthesis method of 2,3,5,8-tetraphenylquinoxaline (abbreviation: TPQ) that is the quinoxaline derivative of the present invention represented by the structural formula (12) will be described.

First, 20.0 g (146 mmol) of benzo[2,1,3]thiadiazole and 160 mL of hydrobromic acid (48% aqueous solution) were put in a 500-mL three-neck flask. This reaction solution was refluxed at 110° C., and 23 mL (446 mmol) of bromine was dripped thereto. After the dripping, the reaction solution was further refluxed at 110° C. for 1 hour. After the reaction, the reaction mixture was washed with water, and the precipitate was collected by suction filtration. The obtained solid was recrystallized with methanol, so that 31.0 g of 4,7-dibromobenzo[2,1,3]thiadiazole that is a light brown powdered solid was obtained (the yield: 72%).

The following shows a synthesis scheme (b-1) of 4,7-dibromobenzo[2,1,3]thiadiazole.

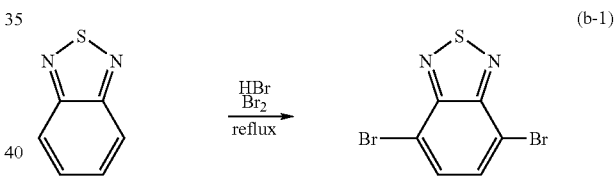

(b-1)

Next, 8.8 g (30 mmol) of 4,7-dibromobenzo[2,1,3]thiadiazole obtained above, 8.3 g (69 mmol) of phenylboronic acid, and 0.69 g (6.0 mmol) of tetrakis(triphenylphosphine)palladium (0) were put in a 500-mL three-neck flask, and nitrogen was substituted for air in the flask. 100 mL of toluene, 40 mL of ethanol, and 45 mL (90 mmol) of a sodium carbonate aqueous solution (2.0 mol/L) were added to this mixture. This mixture was stirred at 90° C. for 6 hours in a nitrogen gas stream.

After the reaction, an organic layer of the reaction mixture was washed with water, and the product was extracted from water used for the washing with ethyl acetate. This extracted solution and the organic layer after the washing with water were mixed and dried with magnesium sulfate. After the drying, suction filtration was performed, and the filtrate was concentrated. The obtained residue was dissolved in toluene, and this solution was subjected to suction filtration through Florisil, Celite, and alumina. The filtrate was concentrated, and the obtained solid was recrystallized with a mixed solvent of chloroform and hexane, so that 8.4 g of 4,7-diphenylbenzo[2,1,3]thiadiazole that is a white powdered solid was obtained (the yield: 97%).

The following shows a synthesis scheme (b-2) of 4,7-diphenylbenzo[2,1,3]thiadiazole.

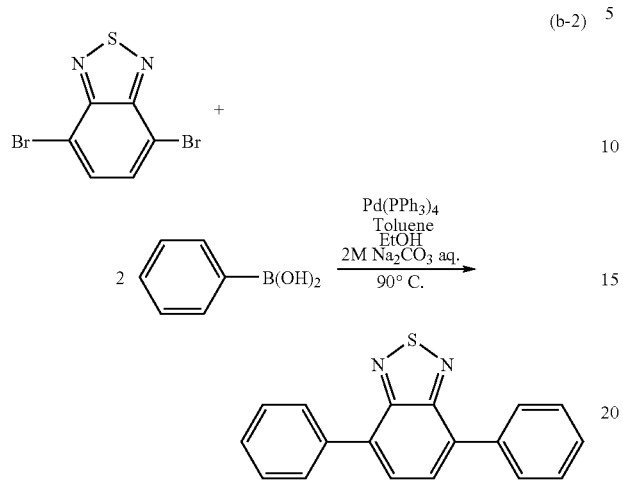

8.65 g (30.0 mmol) of 4,7-diphenylbenzo[2,1,3]thiadiazole obtained above, 19.6 g (300 mmol) of zinc, 105 mL of glacial acetic acid, and 45 mL of water were put in a 500-mL three-neck flask. This mixture was stirred at 80° C. for 7 hours. After the reaction, the reaction solution was added to about 150 mL of a sodium hydroxide aqueous solution (about 2.0 mol/L), and this mixture was stirred at room temperature for 2 hours. The precipitate in the mixture was collected by suction filtration, and the collected solid was washed with water. The solid after the washing was dissolved in ethyl acetate, insoluble matter was collected by suction filtration, and zinc was removed. The obtained filtrate was concentrated, so that 7.6 g of [1,1';4',1"]terphenyl-2',3'-diamine that is a white powdered solid was obtained (the yield: 96%).

The following shows a synthesis scheme (b-3) of [1,1';4',1"]terphenyl-2',3'-diamine.

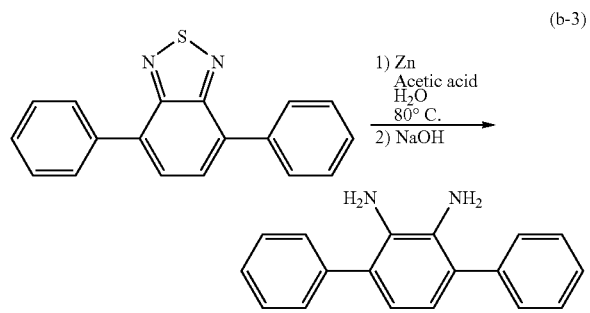

3.9 g (15 mmol) of [1,1';4',1"]terphenyl-2',3'-diamine obtained above, 3.1 g (15 mmol) of benzil, and 50 mL of chloroform were put in a 200-mL three-neck flask. This solution was refluxed at 80° C. for 6 hours in a nitrogen gas stream. After the reaction, the precipitate in the reaction mixture was collected by suction filtration, so that 3.5 g of a yellow powdered solid was obtained (the yield: 53%). It was confirmed by a nuclear magnetic resonance (NMR) method that the obtained yellow powdered solid was 2,3,5,8-tetraphenylquinoxaline (abbreviation: TPQ).

The following shows a synthesis scheme (b-4) of 2,3,5,8-tetraphenylquinoxaline.

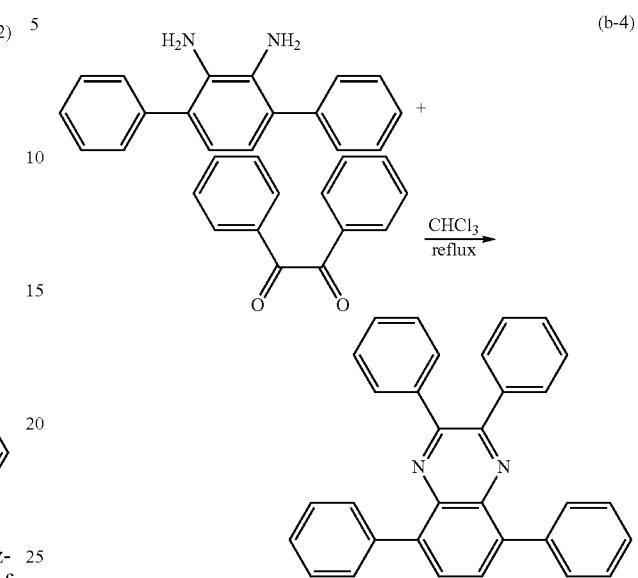

$^1$H-NMR of this compound is shown below.

$^1$H-NMR (CDCl$_3$, 300 MHz): δ=7.25-7.32 (m, 4H), 7.42-7.46 (m, 3H), 7.51-7.61 (m, 8H), 7.86-7.90 (m, 7H).

Figure 5A:
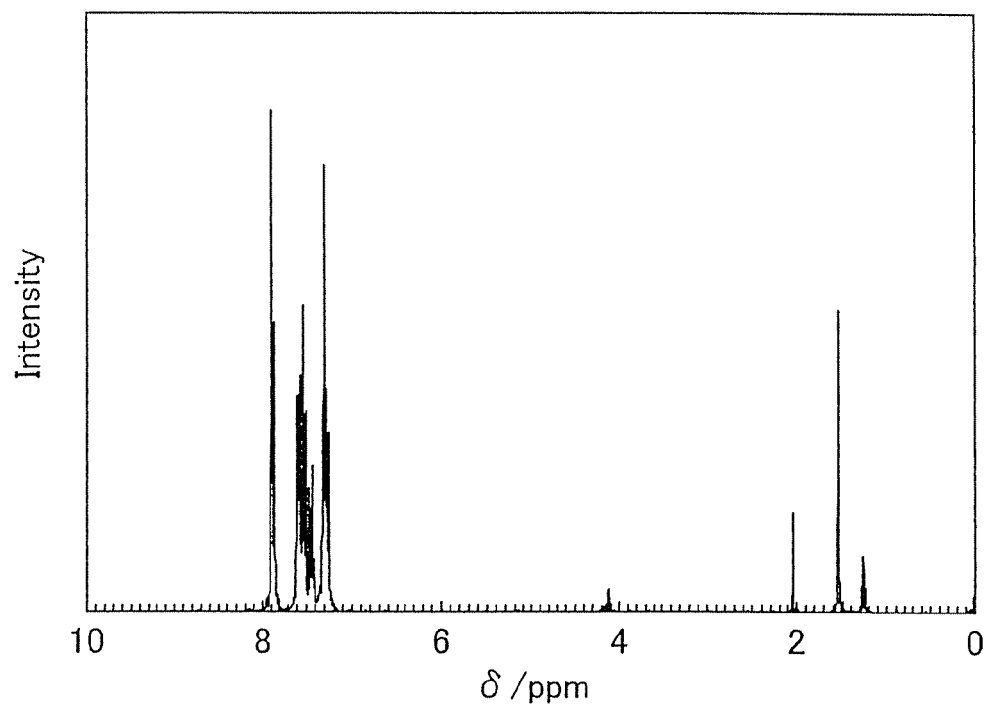
FIGS. 5A and 5B are a $^1$H-NMR chart of a quinoxaline derivative (TPQ) obtained in Synthesis Example 1.
Figure 5B:
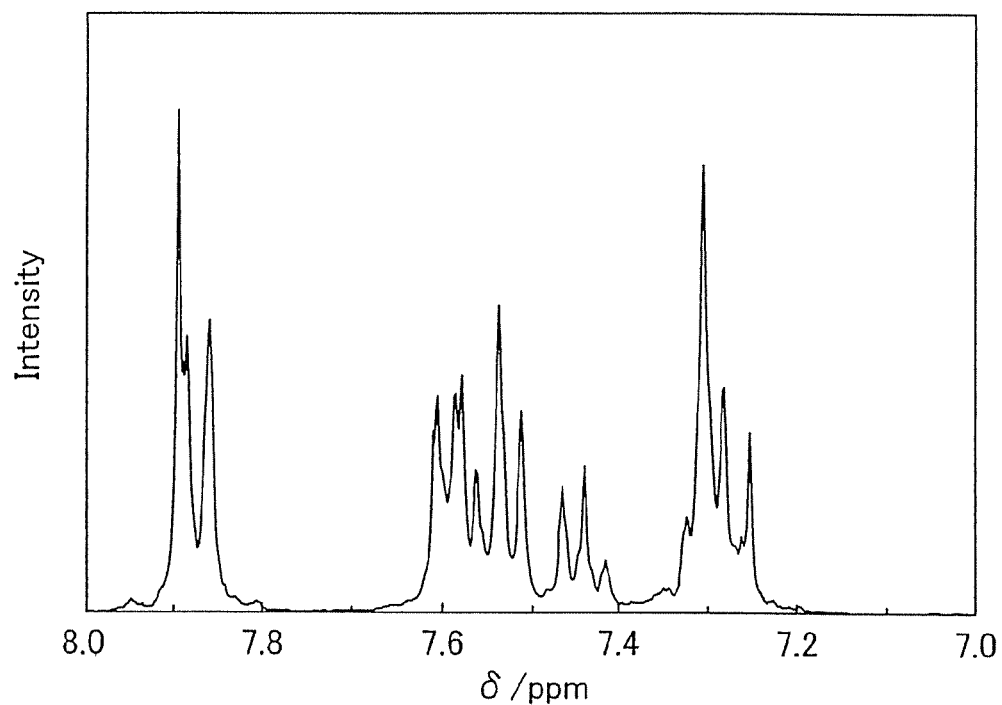

FIGS. 5A and 5B show a $^1$H-NMR chart. Note that FIG. 5B is a chart obtained by enlarging the range of 7.0 ppm to 8.0 ppm in FIG. 5A.

Figure 6A:
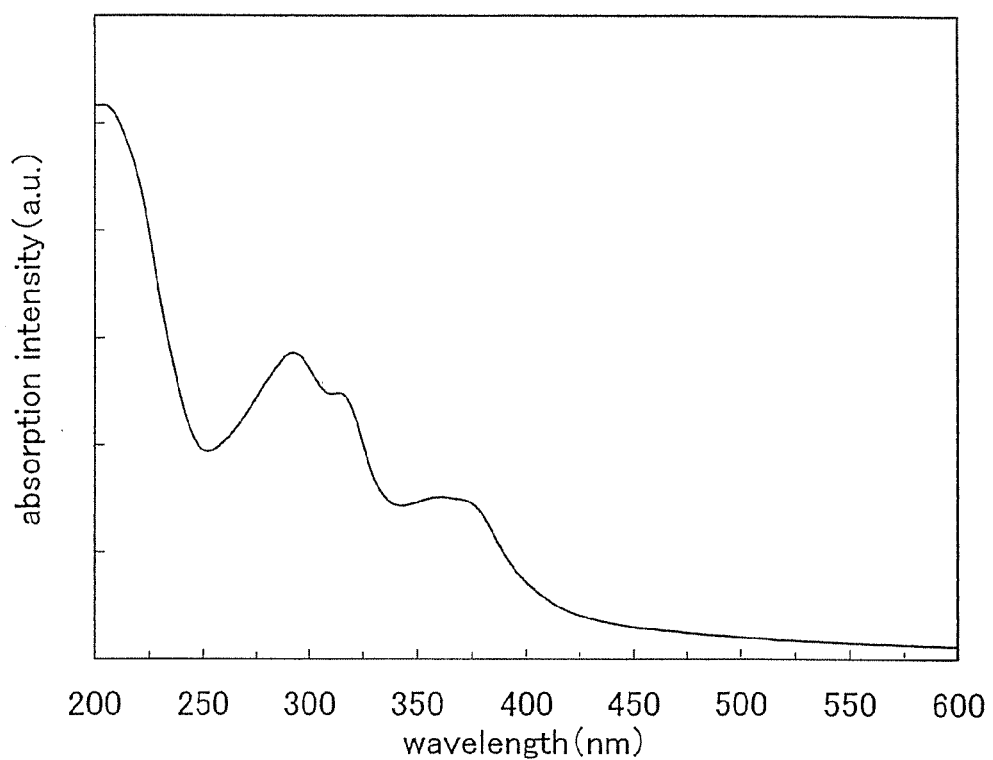
FIGS. 6A and 6B show the absorption spectra of TPQ.
Figure 6B:
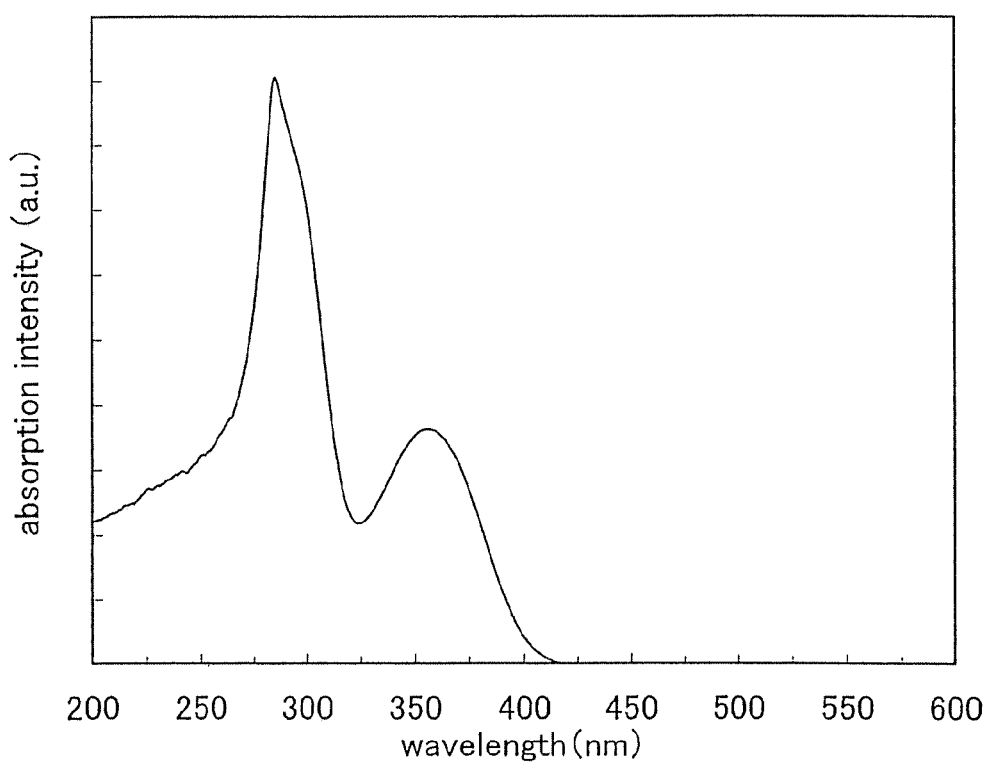

FIGS. 6A and 6B show the absorption spectra of TPQ. The ultraviolet-visible spectrophotometer (V-550, manufactured by JASCO Corporation) was used for the measurement. In FIGS. 6A and 6B, the horizontal axis represents a wavelength (nm) and the vertical axis represents absorption intensity (arbitrary unit: a.u). FIG. 6A shows the absorption spectrum of TPQ in a thin-film state, and FIG. 6B shows the absorption spectrum of TPQ dissolved in a toluene solution. The solution was put in a quartz cell and the thin film was evaporated over a quartz substrate as samples, and the absorption spectra thereof, from each of which the absorption spectrum of quartz was subtracted, are shown. Further, an energy gap of TPQ was obtained according to the absorption spectrum in a thin-film state (FIG. 6A) using Tauc plot, and the energy gap was found to be 3.09 eV.

Figure 7A:
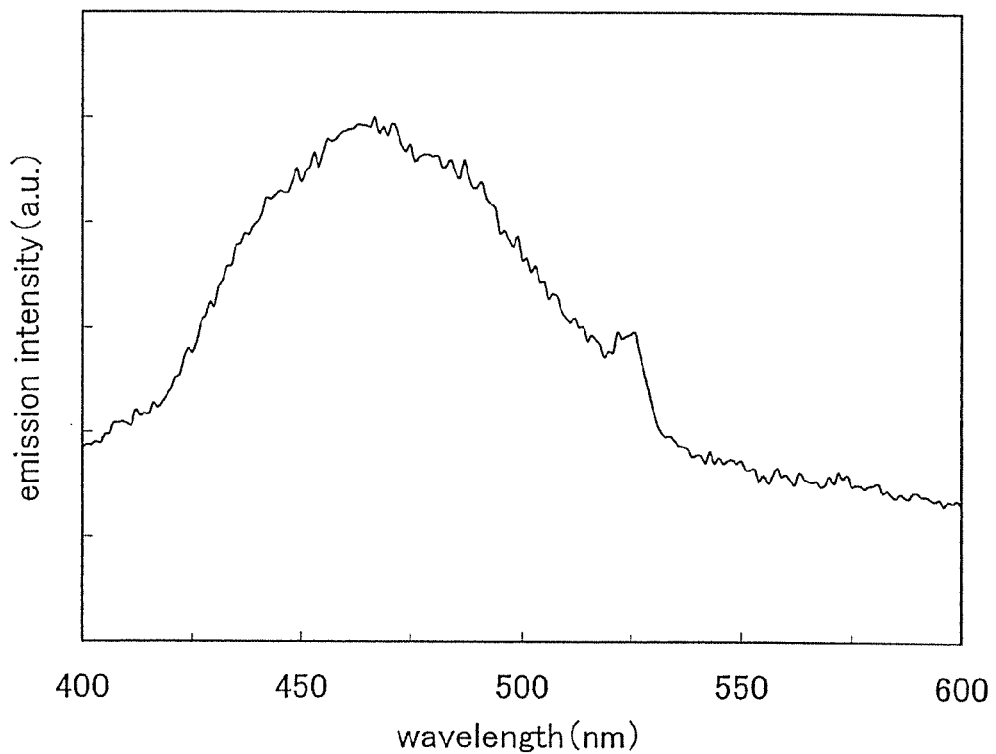
FIGS. 7A and 7B show the light-emission spectra of TPQ.
Figure 7B:
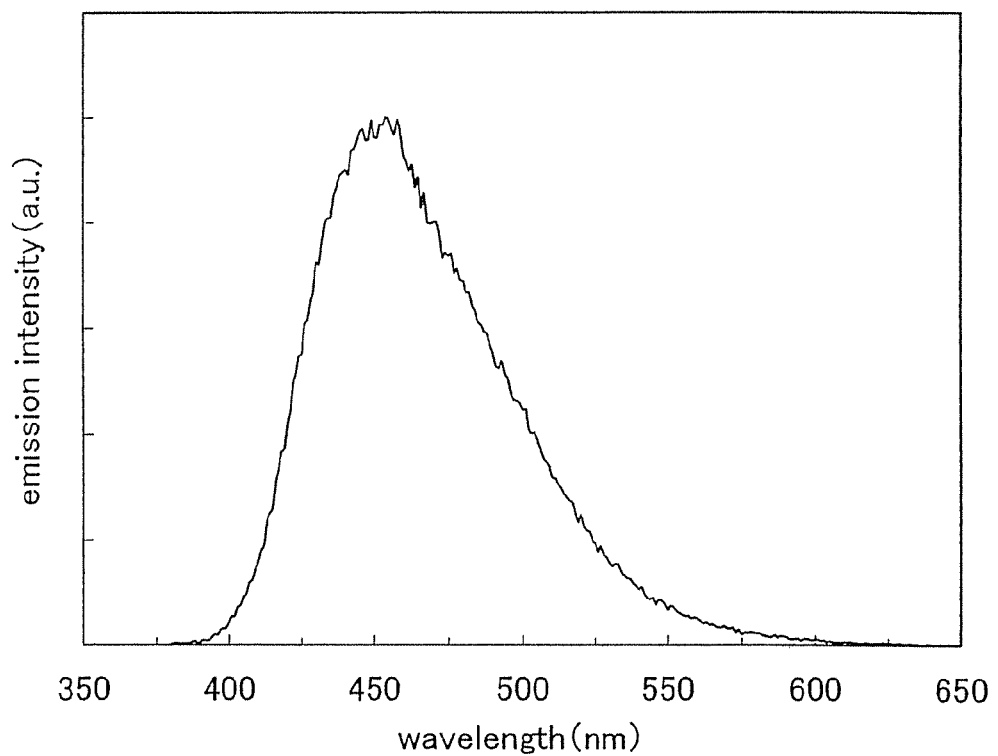

FIGS. 7A and 7B show the light-emission spectra of TPQ. In FIGS. 7A and 7B, the horizontal axis represents a wavelength (nm) and the vertical axis represents emission intensity (arbitrary unit). FIG. 7A shows the light-emission spectrum of TPQ in a thin-film state (an excited wavelength: 337 nm), and FIG. 7B shows the light-emission spectrum of TPQ dissolved in a toluene solution (an excited wavelength: 358 nm). It is found according to FIGS. 7A and 7B that light-emission from TPQ has a peak at 467 nm in a thin-film state and at 454 nm in the toluene solution. Moreover, the light-emission was recognized as blue light.

A film of the obtained TPQ was formed by an evaporation method. An ionization potential of the compound in a thin-film state was measured with a photoelectron spectrometer (AC-2, manufactured by Riken Keiki Co., Ltd.) and was found to be 6.30 eV. According to this result, it was found that the HOMO level was −6.30 eV. In addition, the LUMO level was obtained using an energy gap (3.09 eV), and the LUMO level was found to be −3.21 eV.

Thermogravimetry-Differential Thermal Analysis (TG-DTA) of the obtained TPQ was performed. A thermogravimetric/differential thermal analyzer (TG/DTA-320, manufactured by Seiko Instruments Inc.) was used for the measurement, and it was found that the temperature at which the weight is less than or equal to 95% with respect to the weight at the onset of measurement was 317° C. and TPQ shows favorable heat resistance.

(Embodiment 2)

In this embodiment, a synthesis example of the quinoxaline derivative of the present invention, which is different from that of Embodiment 1, will be described below. Note that the present invention is not limited by this synthesis example.

SYNTHESIS EXAMPLE 2

A synthesis method of 2,3-diphenyl-5,8-di(1-naphthyl)quinoxaline (abbreviation: DNPQ) that is the quinoxaline derivative of the present invention represented by the structural formula (24) will be described. In synthesis of DNPQ, 4,7-dibromobenzo[2,1,3]thiadiazole is necessary, but a synthesis method thereof is shown in the synthesis scheme (b-1) in Embodiment 1 and thus omitted here.

First, a synthesis method of 4,7-di(1-naphthyl)benzo[2,1,3]thiadiazole will be described. 8.8 g (30 mmol) of 4,7-dibromobenzo[2,1,3]thiadiazole, 11 g (66 mmol) of 1-naphthyl boronic acid, 0.067 g (0.30 mmol) of palladium (II) acetate, and 0.63 g (2.1 mmol) of tri(ortho-tolyl)phosphine were put in a 500-mL three-neck flask, and nitrogen was substituted for air in the flask. 100 mL of toluene, 40 mL of ethanol, and 45 mL (90 mmol) of a sodium carbonate aqueous solution (2.0 mol/L) were added to this mixture. This mixture was stirred at 90° C. for 10 hours in a nitrogen gas stream. After the reaction, the precipitate in the reaction mixture was collected by suction filtration. The obtained solid was recrystallized with a mixed solvent of chloroform and hexane, so that 11 g of 4,7-di(1-naphthyl)benzo[2,1,3]thiadiazole that is a white powdered solid was obtained (the yield: 98%).

The following shows a synthesis scheme (c-1) of 4,7-di(1-naphthyl)benzo[2,1,3]thiadiazole.

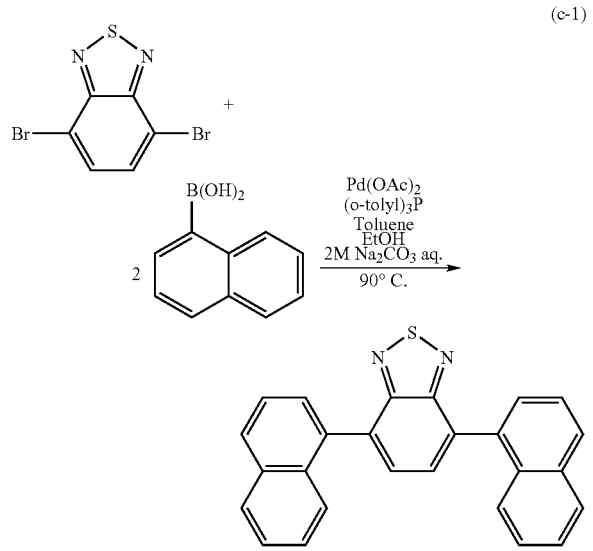

11.3 g (29.1 mmol) of 4,7-di(1-naphthyl)benzo[2,1,3]thiadiazole obtained above, 17.2 g (262 mmol) of zinc, 140 mL of glacial acetic acid, and 60 mL of water were put in a 500-mL three-neck flask. This mixture was stirred at 80° C. for 7 hours. After the reaction, the reaction mixture was added to about 150 mL of a sodium hydroxide aqueous solution (about 2.0 mol/L), and this mixture was stirred at room temperature for 2 hours. The precipitate in the mixture was collected by suction filtration, and the collected solid was washed with water. The solid after the washing was dissolved in ethyl acetate, insoluble matter was collected by suction filtration, and zinc was removed. The obtained filtrate was concentrated, so that 2.60 g of 3,6-di(1-naphthyl)benzene-1,2-diamine that is a white powdered solid was obtained (the yield: 25%).

The following shows a synthesis scheme (c-2) of 3,6-di(1-naphthyl)benzene-1,2-diamine.

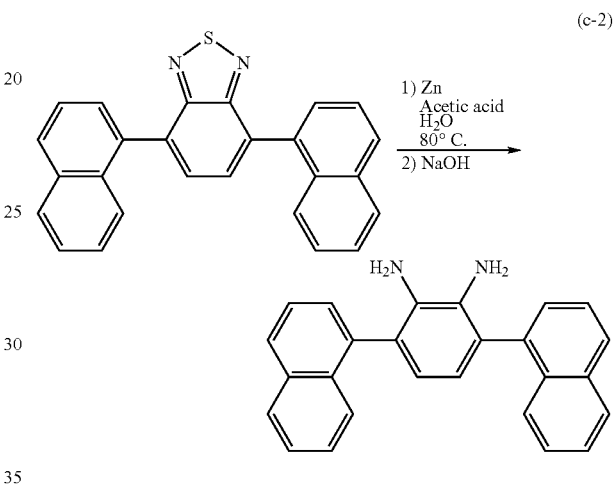

2.6 g (7.2 mmol) of 3,6-di(1-naphthyl)benzene-1,2-diamine obtained above, 1.5 g (7.1 mmol) of benzil, and 40 mL of chloroform were put in a 200-mL three-neck flask. This solution was refluxed at 80° C. for 10 hours in a nitrogen gas stream. After the reaction, the reaction solution was cooled to room temperature and washed with water. Then, the product was extracted from water used for the washing with chloroform, and this extracted solution and an organic layer after the washing with water were mixed and dried with magnesium sulfate. After the drying, suction filtration was performed, and the filtrate was concentrated. The obtained residue was recrystallized with a mixed solvent of chloroform and hexane, so that 2.5 g of a yellow powdered solid was obtained (the yield: 67%). It was confirmed by a nuclear magnetic resonance (NMR) method that the obtained yellow powdered solid was 2,3-diphenyl-5,8-di(1-naphthyl)quinoxaline (abbreviation: DNPQ).

The following shows a synthesis scheme (c-3) of 2,3-diphenyl-5,8-di(1-naphthyl)quinoxaline.

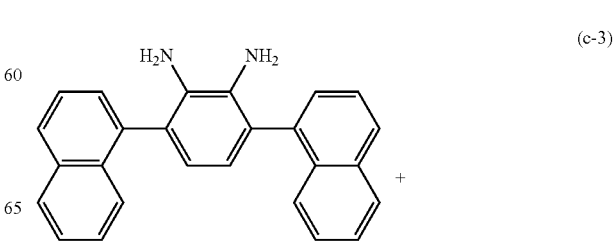

-continued

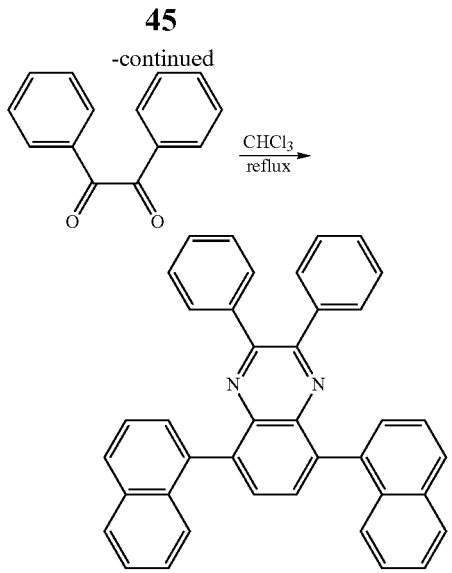

$^1$H-NMR of this compound is shown below.

$^1$H-NMR (CDCl$_3$, 300 MHz): δ=7.03-7.25 (m, 10H), 7.40-7.46 (m, 2H), 7.50-7.56 (m, 2H), 7.60-7.73 (m, 5H), 7.80-7.83 (m, 1H), 7.89-7.99 (m, 6H).

Figure 8A:
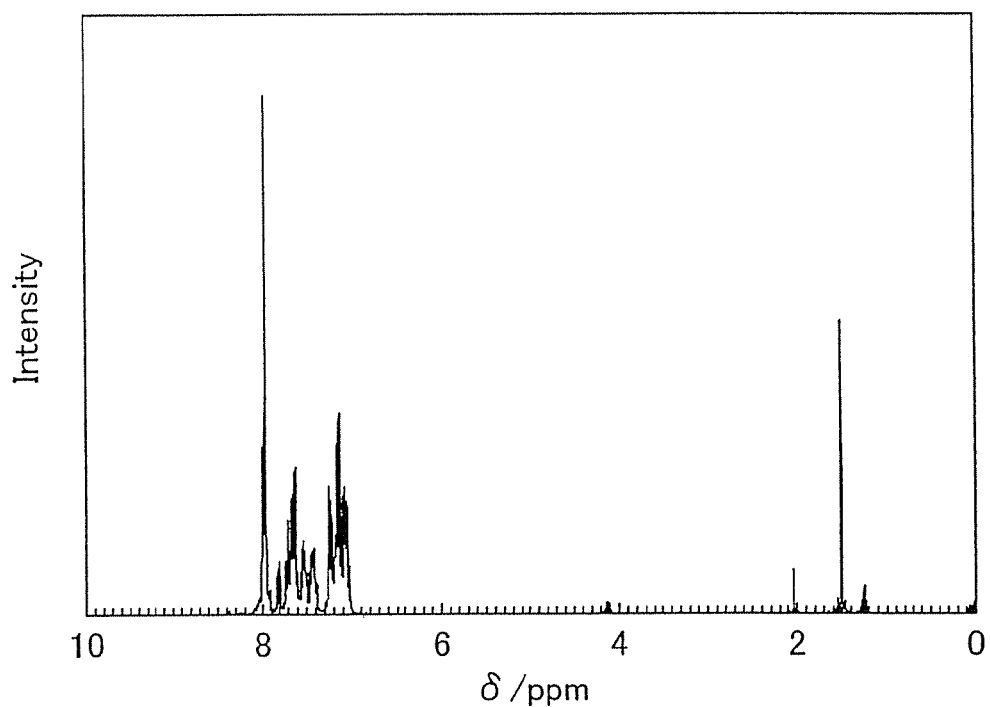
FIGS. 8A and 8B are a $^1$H-NMR chart of a quinoxaline derivative (DNPQ) obtained in Synthesis Example 2.
Figure 8B:
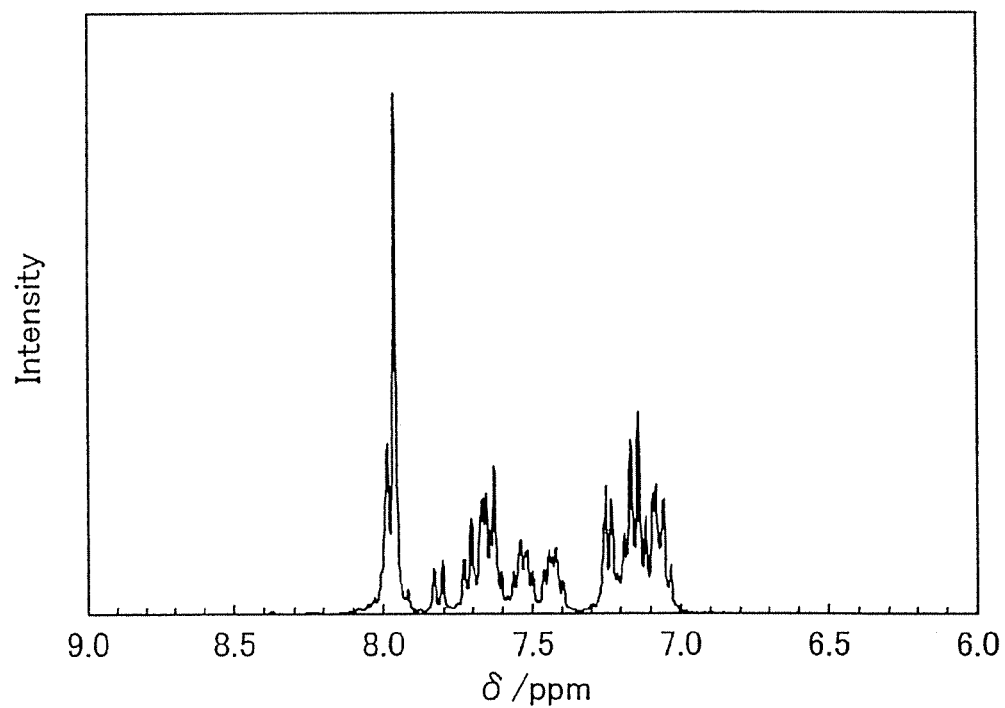

FIGS. 8A and 8B show a $^1$H-NMR chart. Note that FIG. 8B is a chart obtained by enlarging the range of 6.0 ppm to 9.0 ppm in FIG. 8A.

Figure 9A:
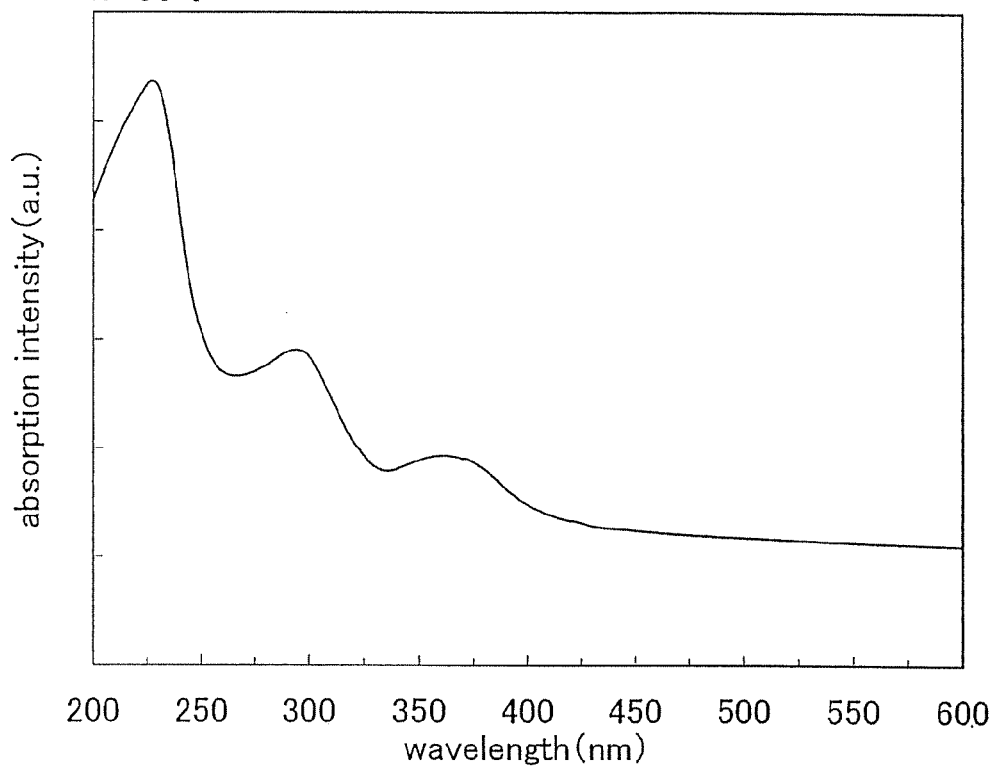
FIGS. 9A and 9B show the absorption spectra of DNPQ.
Figure 9B:
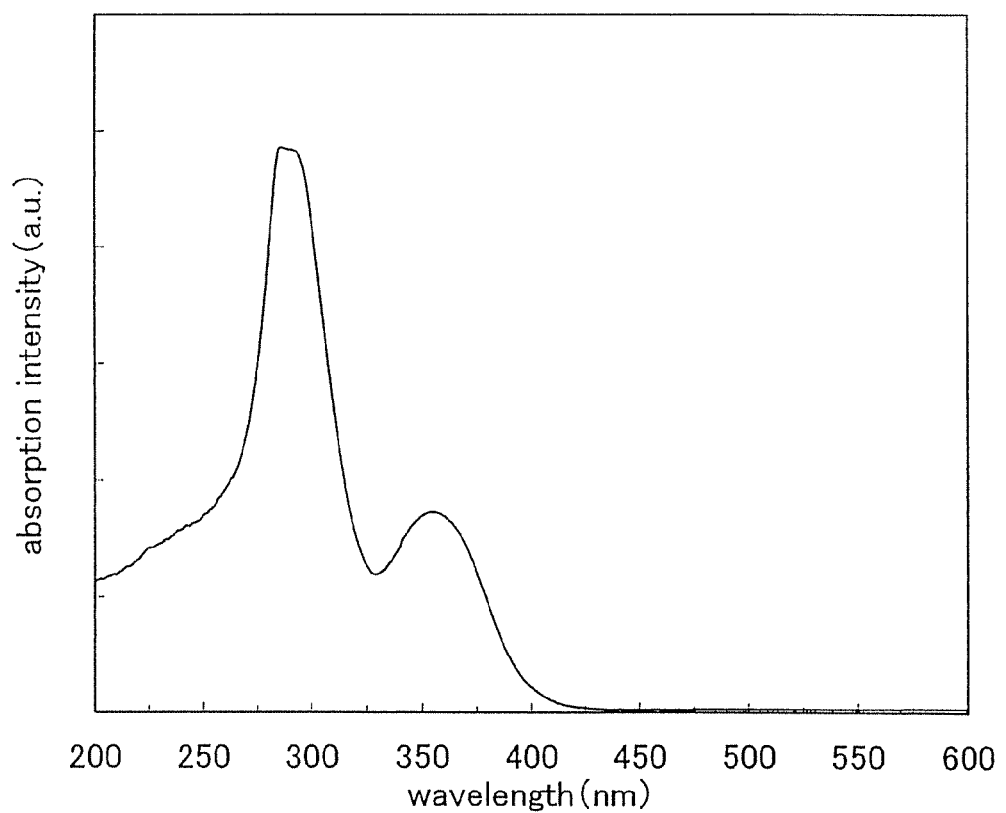

FIGS. 9A and 9B show the absorption spectra of DNPQ. The ultraviolet-visible spectrophotometer (V-550, manufactured by JASCO Corporation) was used for the measurement. In FIGS. 9A and 9B, the horizontal axis represents a wavelength (nm) and the vertical axis represents absorption intensity (arbitrary unit: a.u). FIG. 9A shows the absorption spectrum of DNPQ in a thin-film state, and FIG. 9B shows the absorption spectrum of DNPQ dissolved in a toluene solution. The solution was put in a quartz cell and the thin film was evaporated over a quartz substrate as samples, and the absorption spectra thereof, from each of which the absorption spectrum of quartz was subtracted, are shown. Further, an energy gap of DNPQ was obtained according to the absorption spectrum in a thin-film state (FIG. 9A) using Tauc plot, and the energy gap was found to be 2.92 eV.

Figure 10A:
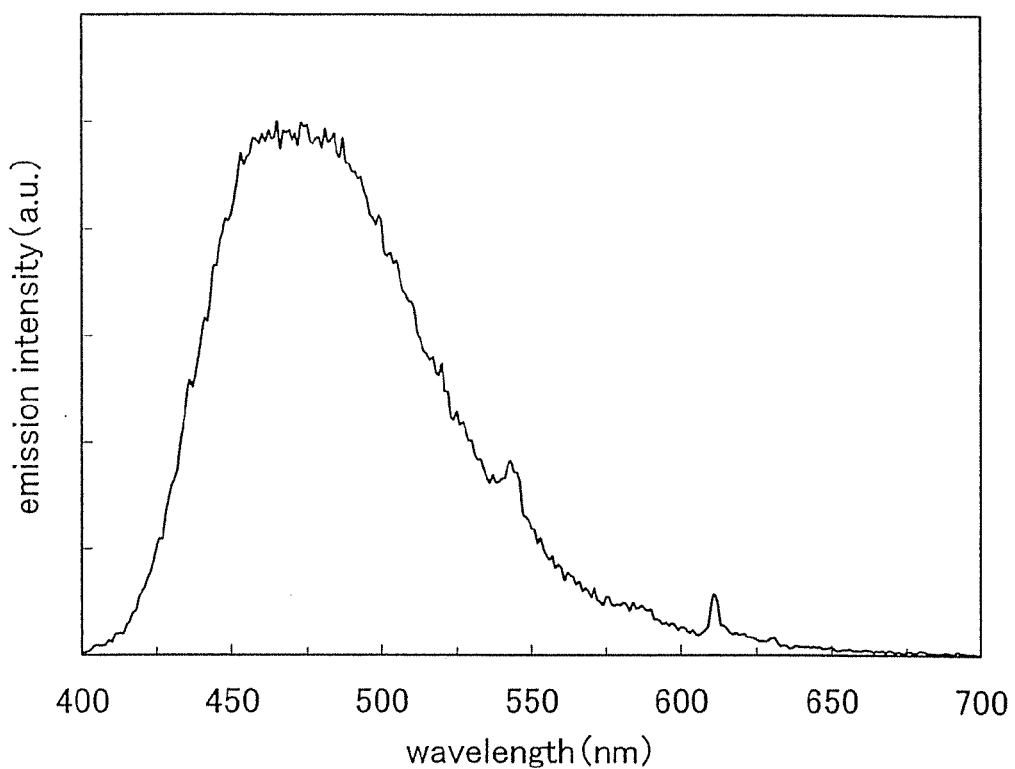
FIGS. 10A and 10B show the light-emission spectra of DNPQ.
Figure 10B:
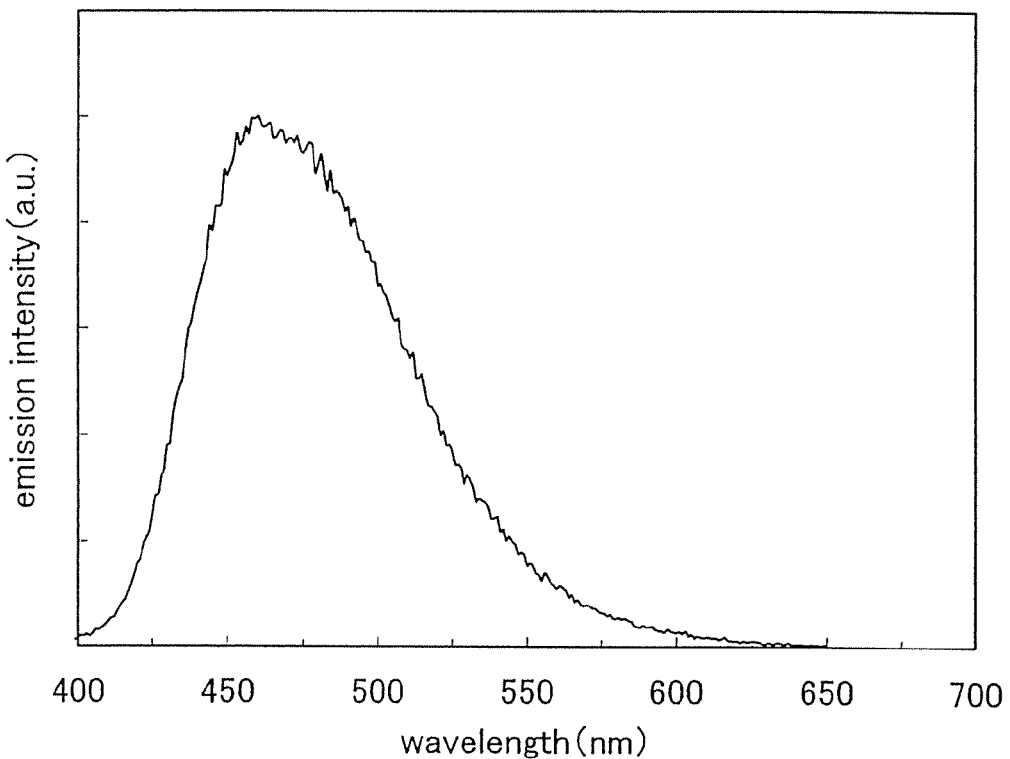

FIGS. 10A and 10B show the light-emission spectra of DNPQ. In FIGS. 10A and 10B, the horizontal axis represents a wavelength (nm) and the vertical axis represents emission intensity (arbitrary unit). FIG. 10A shows the light-emission spectrum of DNPQ in a thin-film state (an excited wavelength: 371 nm), and FIG. 10B shows the light-emission spectrum of DNPQ dissolved in a toluene solution (an excited wavelength: 359 nm). It is found according to FIGS. 10A and 10B that light-emission from DNPQ has a peak around 465 nm in the thin-film state and at 460 nm in the toluene solution. Moreover, the light-emission was recognized as light-blue light.

A film of the obtained DNPQ was formed by an evaporation method. An ionization potential of the compound in a thin-film state was measured with a photoelectron spectrometer (AC-2, manufactured by Riken Keiki Co., Ltd.) and was found to be 5.24 eV. According to this result, it was found that the HOMO level was −5.24 eV. In addition, the LUMO level was obtained using an energy gap (2.92 eV), and the LUMO level was found to be −2.32 eV. Further, Thermogravimetry-Differential Thermal Analysis (TG-DTA) of the obtained DNPQ was performed. A thermogravimetric/differential thermal analyzer (TG/DTA-320, manufactured by Seiko Instruments Inc.) was used for the measurement, and it was found that the temperature at which the weight is less than or equal to 95% with respect to the weight at the onset of measurement was 363° C. and DNPQ shows favorable heat resistance.

(Embodiment 3)

In this embodiment, a synthesis example of the quinoxaline derivative of the present invention, which is different from those of Embodiments 1 and 2, will be described below. Note that the present invention is not limited by this synthesis example.

SYNTHESIS EXAMPLE 3

A synthesis method of 2,3-diphenyl-5,8-bis(2-biphenylyl)quinoxaline (abbreviation: BPPQ) that is the quinoxaline derivative of the present invention represented by the structural formula (27) will be described. In synthesis of BPPQ, 4,7-dibromobenzo[2,1,3]thiadiazole is necessary, but a synthesis method thereof is shown in the synthesis scheme (b-1) in Embodiment 1 and thus omitted here.

First, a synthesis method of 4,7-di(2-biphenylyl)benzo[2,1,3]thiadiazole will be described. 4.4 g (15 mmol) of 4,7-dibromobenzo[2,1,3]thiadiazole, 6.7 g (34 mmol) of 2-biphenylboronic acid, and 0.35 g (0.3 mmol) of tetrakis(triphenylphosphine)palladium (0) were put in a 300-mL three-neck flask, and nitrogen was substituted for air in the flask.

50 mL of toluene, 20 mL of ethanol, and 22 mL (44 mmol) of a sodium carbonate aqueous solution (2.0 mol/L) were added to this mixture. This mixture was refluxed at 90° C. for 8 hours in a nitrogen gas stream. After the reaction, the precipitate in the reaction mixture was collected by suction filtration. The obtained solid was recrystallized with a mixed solvent of chloroform and hexane, so that 4.5 g of 4,7-di(2-biphenylyl)benzo[2,1,3]thiadiazole that is a white powdered solid was obtained (the yield: 69%).

The following shows a synthesis scheme (d-1) of 4,7-di(2-biphenylyl)benzo[2,1,3]thiadiazole.

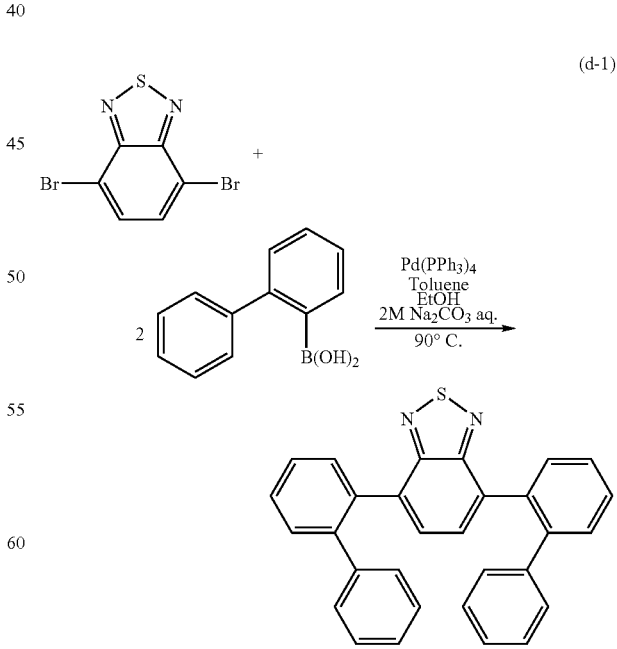

(d-1)

2.2 g (5.0 mmol) of 4,7-di(2-biphenylyl)benzo[2,1,3]thiadiazole obtained above, 3.3 g (50 mmol) of zinc, 10 mL of glacial acetic acid, and 5 mL of water were put in a 100-mL three-neck flask. This mixture was stirred at 80° C. for 6 hours. After the reaction, the reaction mixture was added to about 20 mL of a sodium hydroxide aqueous solution (about 2.0 mol/L), and this mixture was stirred at room temperature for 2 hours. The precipitate in the mixture was collected by suction filtration, and the collected solid was washed with water. The solid after the washing was dissolved in ethyl acetate, insoluble matter was collected by suction filtration, and zinc was removed. The obtained filtrate was concentrated, so that 2.1 g of 3,6-di(2-biphenylyl)benzene-1,2-diamine was obtained (the yield: 99% or more).

The following shows a synthesis scheme (d-2) of 3,6-di(2-biphenylyl)benzene-1,2-diamine.

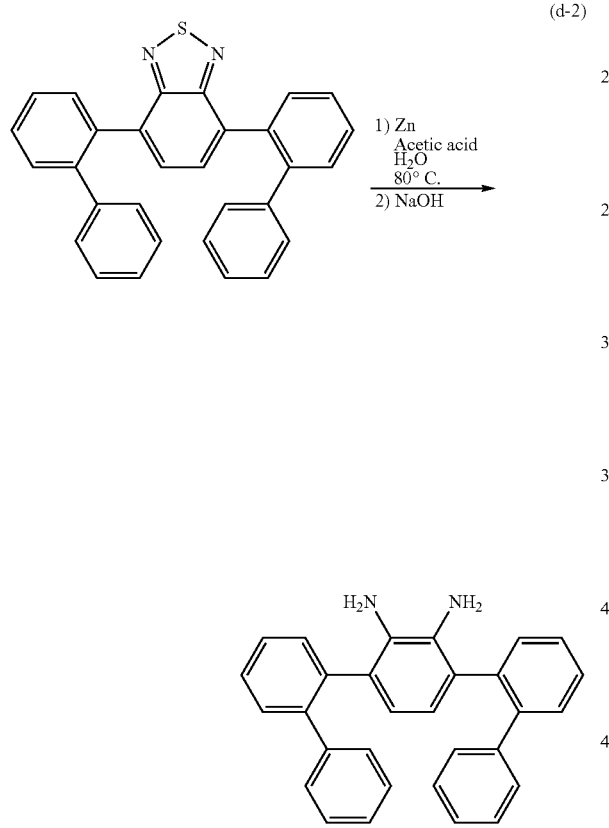

2.1 g (5.0 mmol) of 3,6-di(2-biphenylyl)benzene-1,2-diamine obtained above, 0.94 g (4.5 mmol) of benzil, and 40 mL of chloroform were put in a 200-mL three-neck flask. This solution was refluxed at 80° C. for 10 hours in a nitrogen gas stream. After the reaction, the reaction solution was cooled to room temperature and washed with water. Then, the product was extracted from water used for the washing with chloroform, and this extracted solution and an organic layer after the washing with water were mixed and dried with magnesium sulfate. After the drying, suction filtration was performed, and the filtrate was concentrated. The obtained residue was recrystallized with a mixed solvent of chloroform and hexane, so that 1.6 g of a yellow powdered solid was obtained (the yield: 60%). It was confirmed by a nuclear magnetic resonance (NMR) method that the obtained yellow powdered solid was 2,3-diphenyl-5,8-bis(2-biphenylyl)quinoxaline (abbreviation: BPPQ).

The following shows a synthesis scheme (d-3) of 2,3-diphenyl-5,8-bis(2-biphenylyl)quinoxaline.

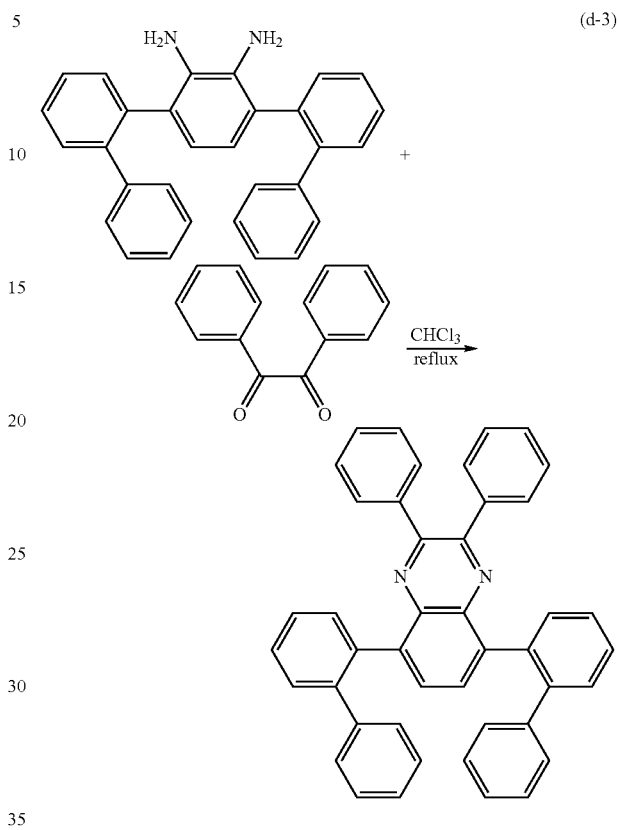

$^1$H-NMR of this compound is shown below.

$^1$H-NMR (CDCl$_3$, 300 MHz): δ=6.99-7.07 (m, 10H), 7.18-7.28 (m, 6H), 7.31-7.33 (m, 4H), 7.42 (s, 2H), 7.44-7.53 (m, 6H), 7.58-7.61 (m, 2H).

Figure 11A:
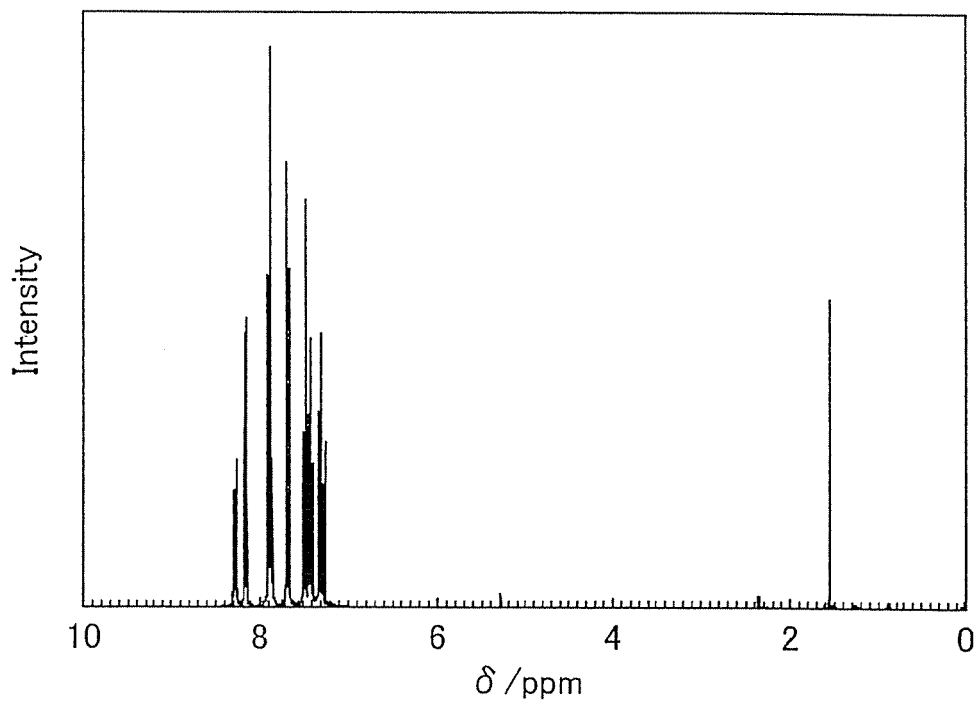
FIGS. 11A and 11B are a $^1$H-NMR chart of a quinoxaline derivative (BPPQ) obtained in Synthesis Example 3.
Figure 11B:
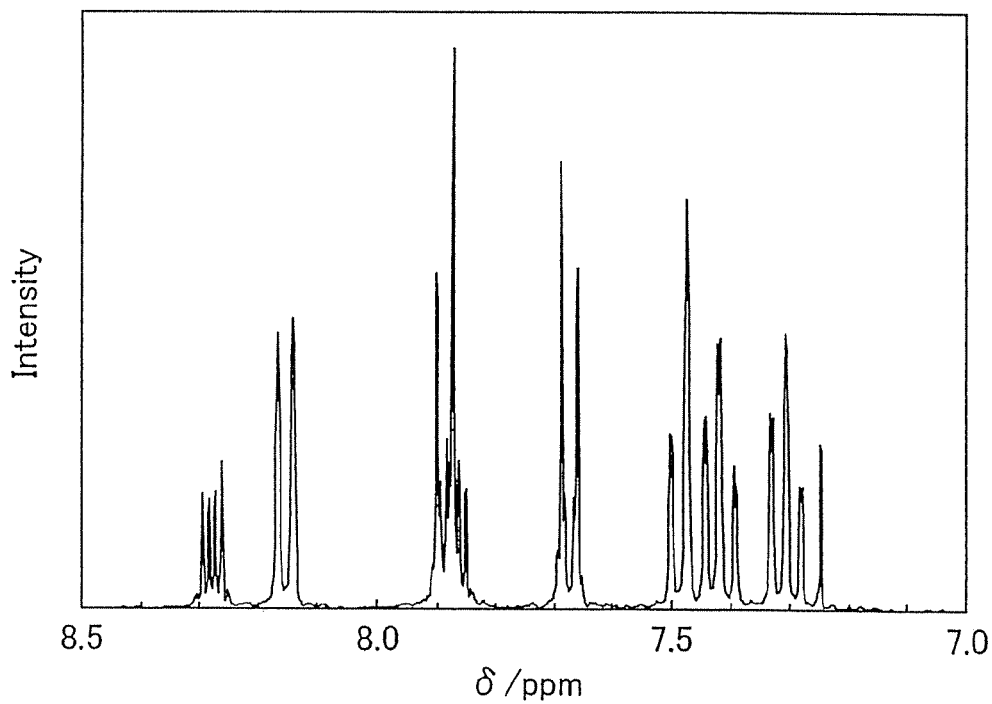

FIGS. 11A and 11B show a $^1$H-NMR chart. Note that FIG. 11B is a chart obtained by enlarging the range of 7.0 ppm to 8.5 ppm in FIG. 11A.

Figure 12A:
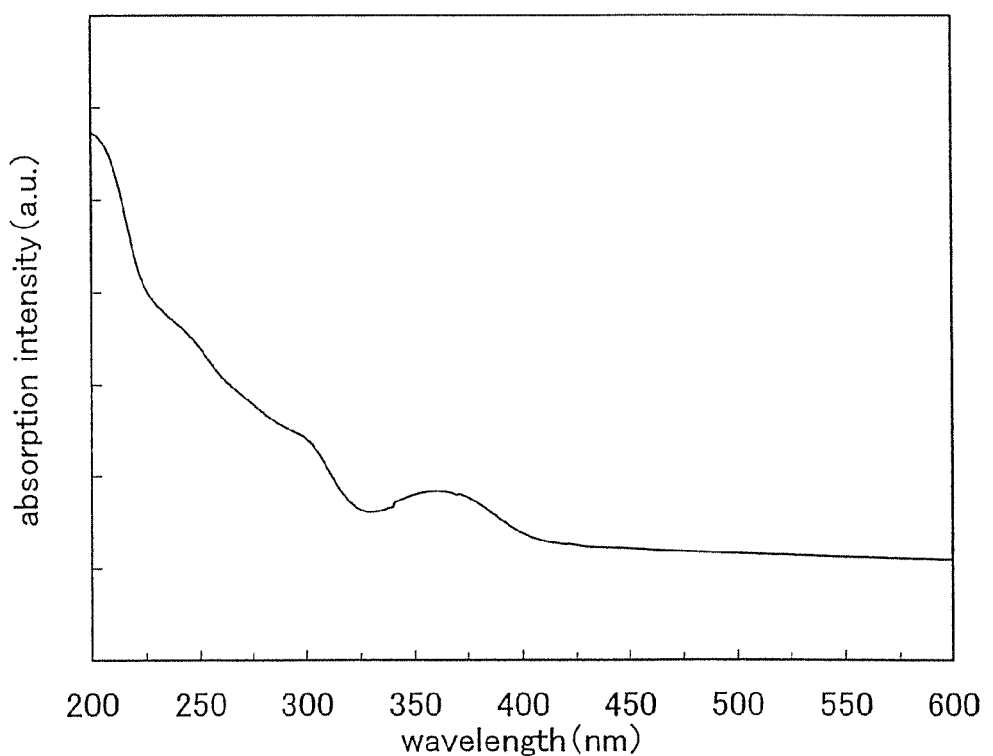
FIGS. 12A and 12B show the absorption spectra of BPPQ.
Figure 12B:
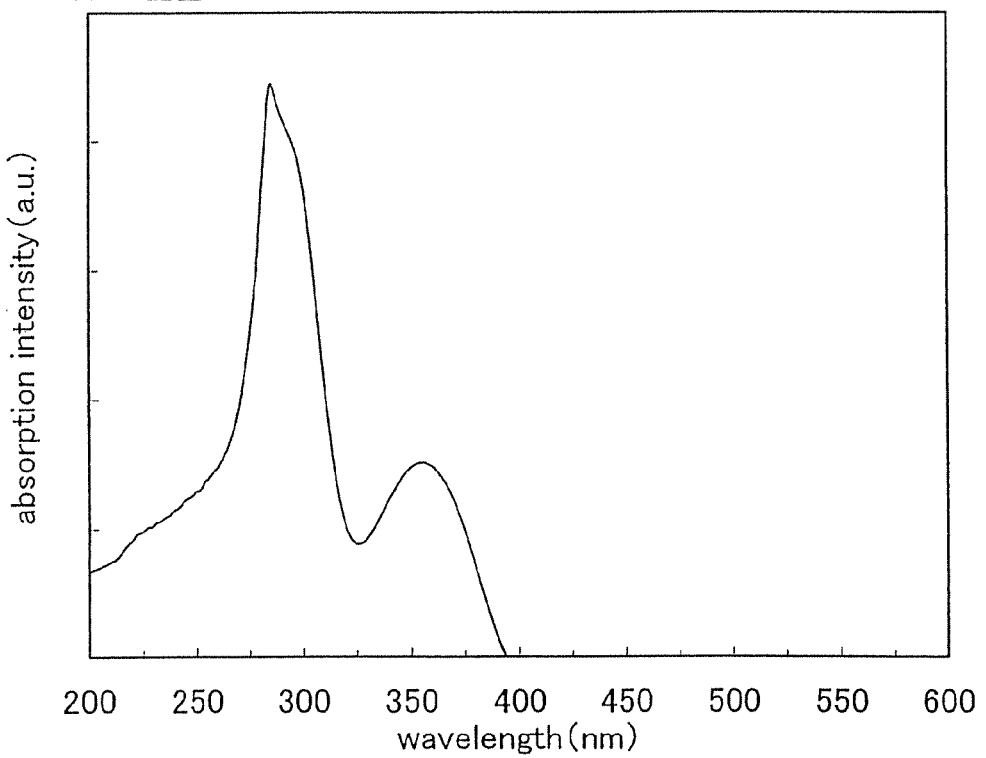

FIGS. 12A and 12B show the absorption spectra of BPPQ. The ultraviolet-visible spectrophotometer (V-550, manufactured by JASCO Corporation) was used for the measurement. In FIGS. 12A and 12B, the horizontal axis represents a wavelength (nm) and the vertical axis represents absorption intensity (arbitrary unit: a.u). FIG. 12A shows the absorption spectrum of BPPQ in a thin-film state, and FIG. 12B shows the absorption spectrum of BPPQ dissolved in a toluene solution. The solution was put in a quartz cell and the thin film was evaporated over a quartz substrate as samples, and the absorption spectra thereof, from each of which the absorption spectrum of quartz was subtracted, are shown. Further, an energy gap of BPPQ was obtained according to the absorption spectrum in a thin-film state (FIG. 12A) using Tauc plot, and the energy gap was found to be 2.99 eV.

Figure 13A:
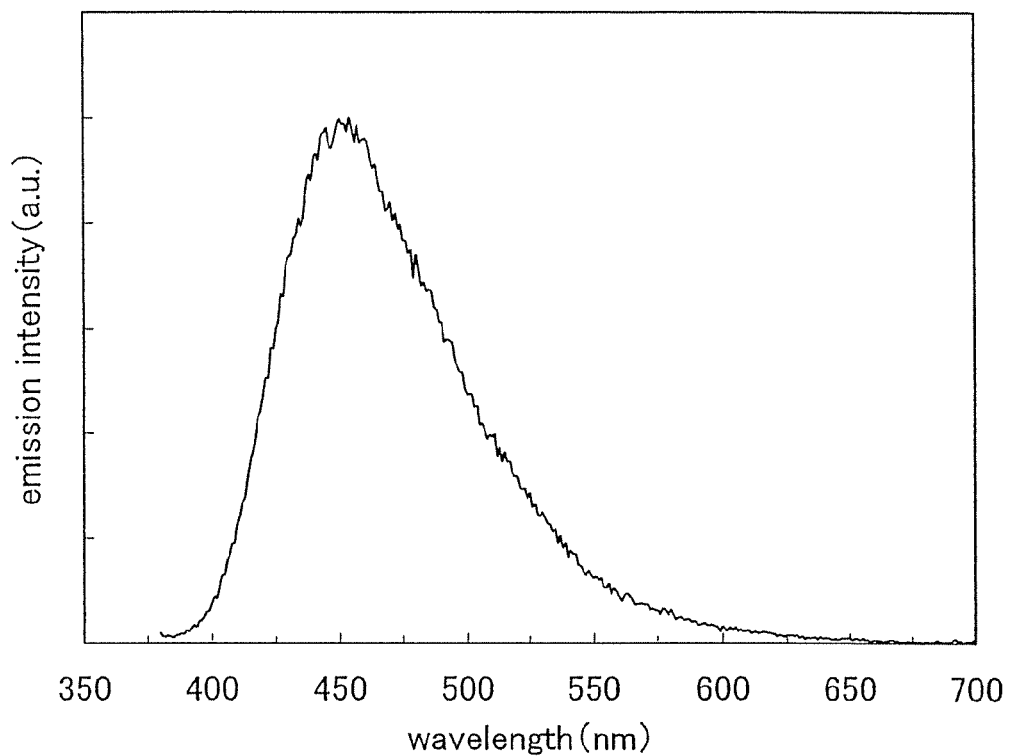
FIGS. 13A and 13B show the light-emission spectra of BPPQ.
Figure 13B:
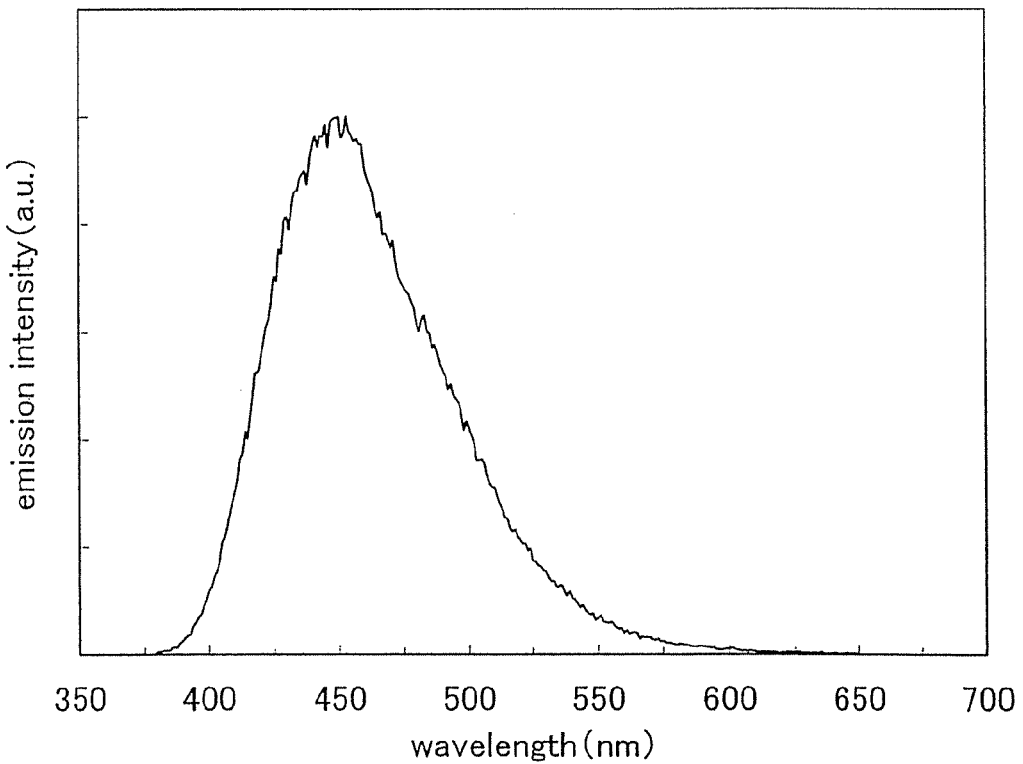

FIGS. 13A and 13B show the light-emission spectra of BPPQ. In FIGS. 13A and 13B, the horizontal axis represents a wavelength (nm) and the vertical axis represents emission intensity (arbitrary unit). FIG. 13A shows the light-emission spectrum of BPPQ in a thin-film state (an excited wavelength: 371 nm), and FIG. 13B shows the light-emission spectrum of BPPQ dissolved in a toluene solution (an excited wavelength: 358 nm). It is found according to FIGS. 13A and 13B that light-emission from BPPQ has a peak at 454 nm in the thin-film state and at 453 nm in the toluene solution. Moreover, the light-emission was recognized as blue light.

A film of the obtained BPPQ was formed by an evaporation method. An ionization potential of the compound in a thin-film state was measured with a photoelectron spectrometer (AC-2, manufactured by Riken Keiki Co., Ltd.) and was found to be 5.39 eV. According to this result, it was found that the HOMO level was −5.39 eV. In addition, the LUMO level was obtained using an energy gap (2.99 eV), and the LUMO level was found to be −2.40 eV.

Further, Thermogravimetry-Differential Thermal Analysis (TG-DTA) of the obtained BPPQ was performed. A thermogravimetric/differential thermal analyzer (TG/DTA-320, manufactured by Seiko Instruments Inc.) was used for the measurement, and it was found that the temperature at which the weight is less than or equal to 95% with respect to the weight at the onset of measurement was 331° C. and BPPQ shows favorable heat resistance.

(Embodiment 4)

Figure 14:
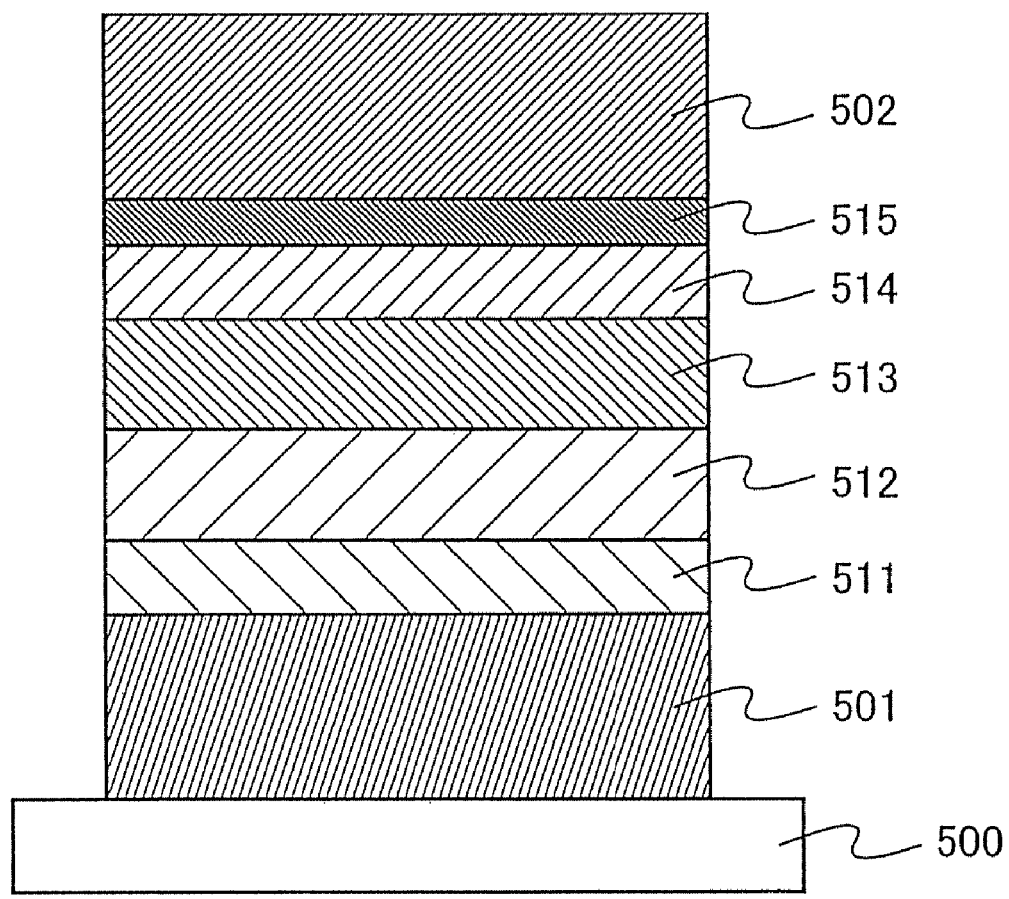
FIG. 14 is an explanatory view of an element structure of a light-emitting element manufactured in Embodiments.

This embodiment will describe, with reference to FIG. 14, a method for manufacturing a light-emitting element in which 2,3,5,8-tetraphenylquinoxaline (abbreviation: TPQ) synthesized in Synthesis Example 1 is used for an electron-transporting layer and operation characteristics of the light-emitting element.

First, indium tin oxide containing silicon oxide (ITSO) was deposited over a glass substrate 500 by a sputtering method, whereby a first electrode 501 was formed. The size of the electrode was set to be 2 mm×2 mm. Next, the substrate 500 provided with the first electrode 501 was fixed to a substrate holder in a vacuum evaporation apparatus so that the side provided with the first electrode 501 faced downward. Then, DNTPD and molybdenum trioxide were deposited by a co-evaporation method on the first electrode 501 to have a thickness of 50 nm, whereby a hole-injecting layer 511 was formed. Note that the co-evaporation was performed so that a mass ratio of DNTPD to molybdenum trioxide was 4:2 (=DNTPD: molybdenum trioxide).

Then, NPB was deposited by an evaporation method on the hole-injecting layer 511 to have a thickness of 10 nm, whereby a hole-transporting layer 512 was formed. Then, CzPA and YGAPA were deposited by a co-evaporation method on the hole-transporting layer 512 to have a thickness of 30 nm, whereby a light-emitting layer 513 was formed. Note that the co-evaporation was performed so that a mass ratio of CzPA to YGAPA was 1:0.04 (=CzPA: YGAPA). Therefore, YGAPA was in a state of being dispersed in a layer formed of CzPA.

TPQ was deposited on the light-emitting layer 513 to have a thickness of 10 nm and then BPhen was deposited to have a thickness of 20 nm, whereby an electron-transporting layer 514 in which TPQ and BPhen were stacked was formed. Each layer was formed by an evaporation method. LiF was deposited on the electron-transporting layer 514 by an evaporation method to have a thickness of 2 nm, whereby an electron-injecting layer 515 was formed. Then, aluminum was deposited by an evaporation method on the electron-injecting layer 515, whereby a second electrode 502 was formed.

As described above, the hole-injecting layer 511, the hole-transporting layer 512, the light-emitting layer 513, the electron-transporting layer 514, and the electron-injecting layer 515 were stacked between the first electrode 501 and the second electrode 502 to form a light-emitting element. Note that the obtained light-emitting element was sealed using a sealing material in a nitrogen atmosphere without being exposed to air. The structural formulas of DNTPD, NPB, CzPA, YGAPA, and BPhen used for these layers will be shown below.

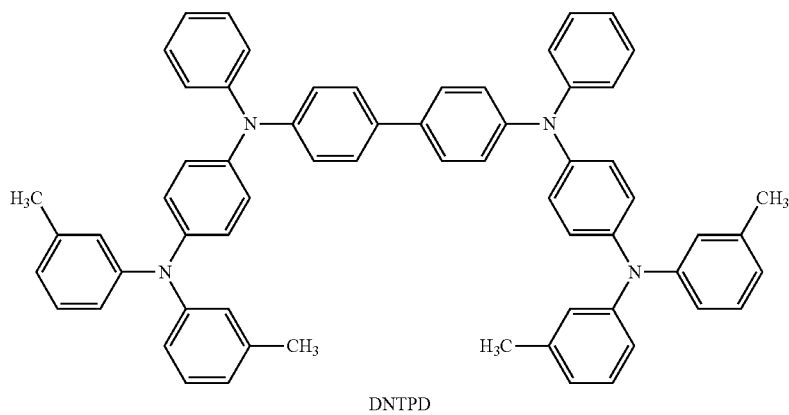

DNTPD

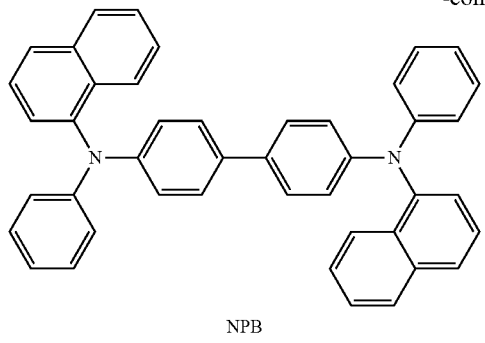

NPB

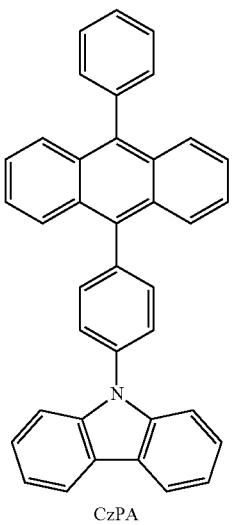

CzPA

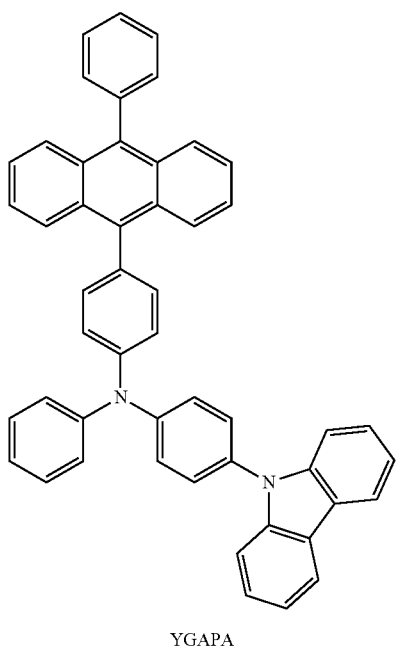

YGAPA

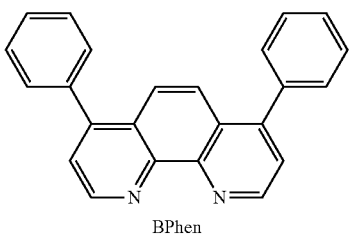

BPhen

COMPARATIVE EXAMPLE 1

As a comparative example of the light-emitting element of this embodiment, a light-emitting element including Alq$_3$ instead of TPQ that is the quinoxaline derivative of the present invention was manufactured. In this comparative example, the electron-transporting layer 514 has a stacked layer structure in which BPhen having a thickness of 20 nm was stacked over Alq$_3$ having a thickness of 10 nm. Other parts were manufactured using the similar substance and method to those of Embodiment 4.

Specifically, DNTPD and molybdenum trioxide were deposited by a co-evaporation method to have a thickness of 50 nm on the first electrode 501 formed of ITSO, whereby a hole-injecting layer 511 was formed. Note that the co-evaporation was performed so that a mass ratio of DNTPD to molybdenum trioxide was 4:2 (=DNTPD: molybdenum trioxide). NPB was deposited to have a thickness of 10 nm thereon as a hole-transporting layer 512. CzPA and YGAPA were deposited by a co-evaporation method on the hole-transporting layer 512 to have a thickness of 30 nm, whereby a light-emitting layer 513 was formed. Note that the co-evaporation was performed so that a mass ratio of CzPA to YGAPA was 1:0.04 (=CzPA: YGAPA).

Alq$_3$ was deposited to have a thickness of 10 nm on the light-emitting layer 513 and then BPhen was deposited to have a thickness of 20 nm, whereby an electron-transporting layer 514 was formed. LiF was deposited to have a thickness of 2 nm on the electron-transporting layer 514, whereby an electron-injecting layer 515 was formed. Further, aluminum was deposited thereon by an evaporation method, whereby a second electrode 502 was formed. A light-emitting element obtained as described above was sealed using a sealing material in a nitrogen atmosphere without being exposed to air.

The following shows the structural formula of Alq$_3$.

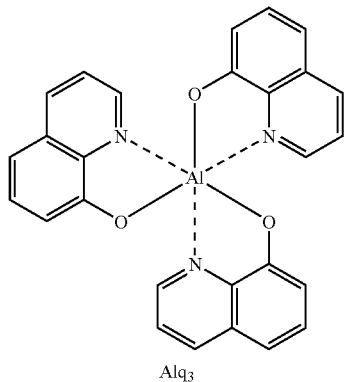

Alq$_3$

Figure 15A:
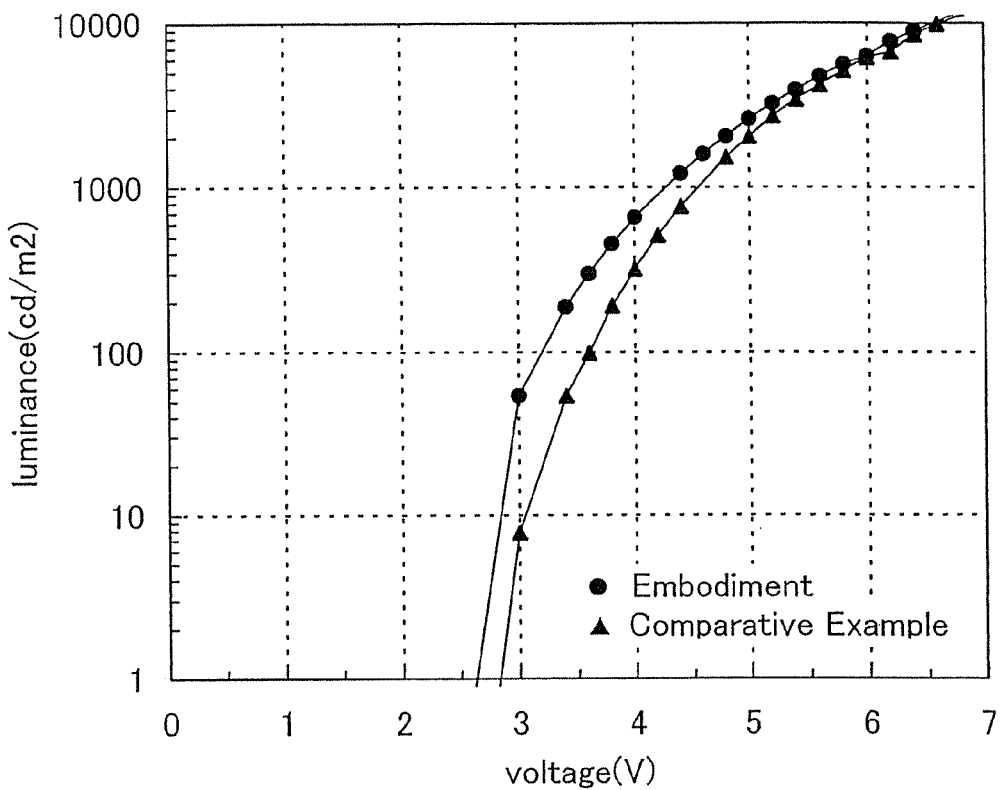
FIGS. 15A and 15B show operation characteristics of a light-emitting element manufactured in Embodiment 4.
Figure 15B:
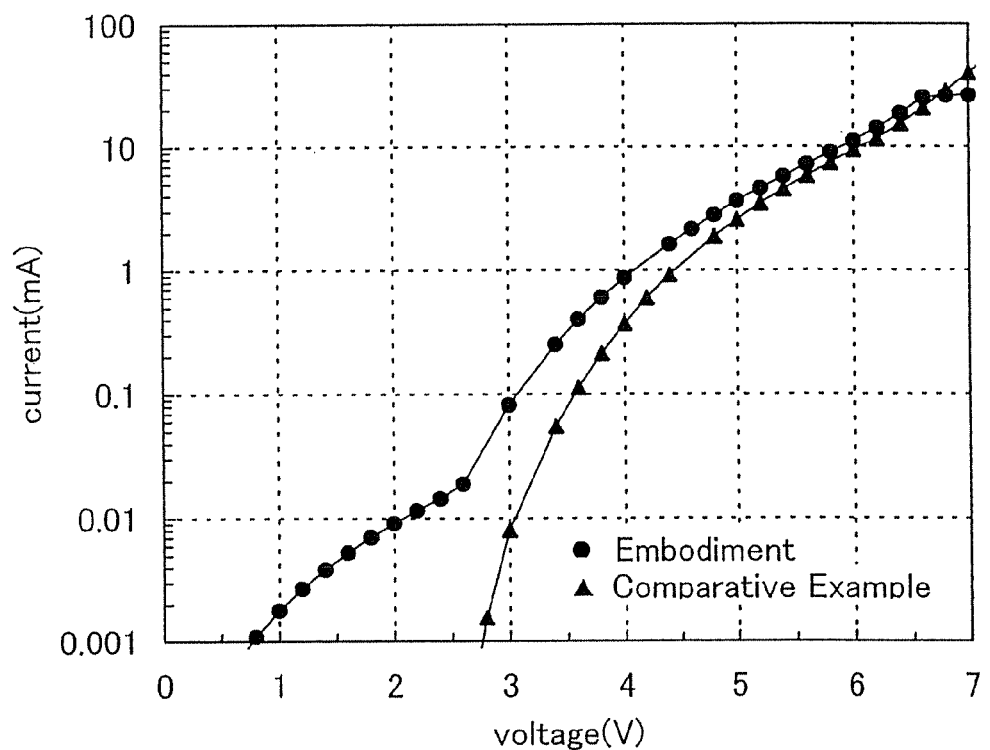

A voltage was applied to the light-emitting elements of this embodiment and Comparative Example 1 so that potential of the first electrode 501 was higher than that of the second electrode 502, and then, operation characteristics of the light-emitting elements were examined. Note that measurement was performed under a condition kept at room temperature (25° C.). A result thereof is shown in FIGS. 15A and 15B. FIG. 15A shows a measurement result of voltage-luminance characteristics. FIG. 15B shows a measurement result of voltage-current characteristics. The results of the measurements of this embodiment and Comparative Example 1 are collectively shown in the same chart. Note that the horizontal axis represents voltage (V) and the vertical axis represents luminance (cd/m$^2$) in FIG. 15A, and the horizontal axis represents voltage (V) and the vertical axis represents current (mA) in FIG. 15B.

According to these results, the light-emitting element manufactured in this embodiment had higher luminance at lower voltage, compared to the light-emitting element of Comparative Example 1. Accordingly, it was found that the light-emitting element of this embodiment had lower drive voltage. In addition, it was also found that the light-emitting element of this embodiment had voltage-current characteristics superior to those of the light-emitting element of Comparative Example 1, and the quinoxaline derivative of the present invention had an electron-transporting property superior to that of Alq$_3$. As described above, by using the quinoxaline derivative of the present invention as an electron-transporting material, a light-emitting element with low drive voltage could be obtained.

Note that at 1000 cd/m$^2$, the CIE chromaticity coordinates of light-emission obtained from the light-emitting element manufactured in this embodiment were (x, y)=(0.15, 0.15), and the CIE chromaticity coordinates of light-emission obtained from the light-emitting element manufactured in Comparative Example 1 were (x, y)=(0.16, 0.15). In any case, light-emission from YGAPA that is a light-emitting substance was obtained.

(Embodiment 5)

This embodiment will describe, with reference to FIG. 14, a method for manufacturing a light-emitting element in which 2,3-diphenyl-5,8-di(1-naphthyl)quinoxaline (abbreviation: DNPQ) synthesized in Synthesis Example 2 is used for an electron-transporting layer and operation characteristics of the light-emitting element.

First, indium tin oxide containing silicon oxide (ITSO) was deposited over a glass substrate 500 by a sputtering method, whereby a first electrode 501 was formed. The size of the electrode was set to be 2 mm×2 mm. Next, the substrate 500 provided with the first electrode 501 was fixed to a substrate holder in a vacuum evaporation apparatus so that the side provided with the first electrode 501 faced downward. Then, DNTPD and molybdenum trioxide were deposited by a co-evaporation method on the first electrode 501 to have a thickness of 50 nm, whereby a hole-injecting layer 511 was formed. Note that the co-evaporation was performed so that a mass ratio of DNTPD to molybdenum trioxide was 4:2 (=DNTPD: molybdenum trioxide).

Then, NPB was deposited by an evaporation method on the hole-injecting layer 511 to have a thickness of 10 nm, whereby a hole-transporting layer 512 was formed. Then, CzPA and YGAPA were deposited by a co-evaporation method on the hole-transporting layer 512 to have a thickness of 30 nm, whereby a light-emitting layer 513 was formed. Note that the co-evaporation was performed so that a mass ratio of CzPA to YGAPA was 1:0.04 (=CzPA: YGAPA). Therefore, YGAPA was in a state of being dispersed in a layer formed of CzPA.

DNPQ was deposited on the light-emitting layer 513 to have a thickness of 10 nm and then BPhen was deposited to have a thickness of 20 nm, whereby an electron-transporting layer 514 in which DNPQ and BPhen were stacked was formed. Each layer was formed by an evaporation method. LiF was deposited on the electron-transporting layer 514 by an evaporation method to have a thickness of 2 nm, whereby an electron-injecting layer 515 was formed. Then, aluminum was deposited by an evaporation method on the electron-injecting layer 515, whereby a second electrode 502 was formed.

As described above, the hole-injecting layer 511, the hole-transporting layer 512, the light-emitting layer 513, the electron-transporting layer 514, and the electron-injecting layer 515 were stacked between the first electrode 501 and the second electrode 502 to form a light-emitting element. Note that the obtained light-emitting element was sealed using a sealing material in a nitrogen atmosphere without being exposed to air. A voltage was applied to the light-emitting element of this embodiment so that potential of the first electrode 501 was higher than that of the second electrode 502, and then, operation characteristics of the light-emitting element were examined. Note that the measurement was performed under a condition kept at room temperature (25° C.).

Figure 16A:
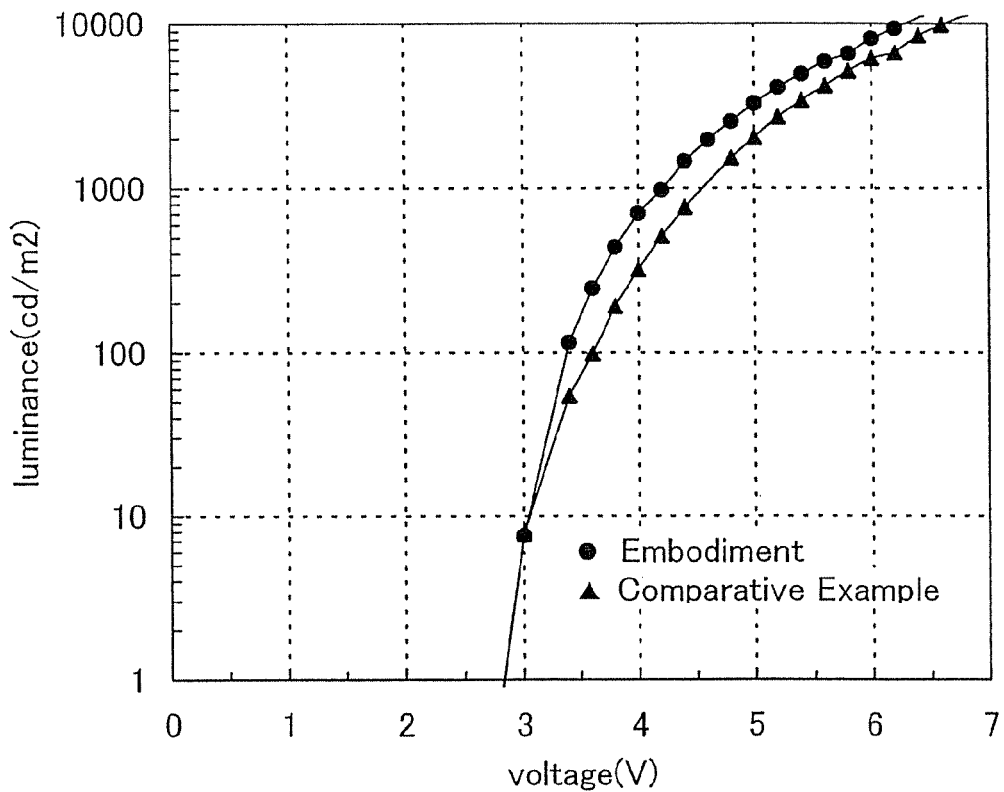
FIGS. 16A and 16B show operation characteristics of a light-emitting element manufactured in Embodiment 5.
Figure 16B:
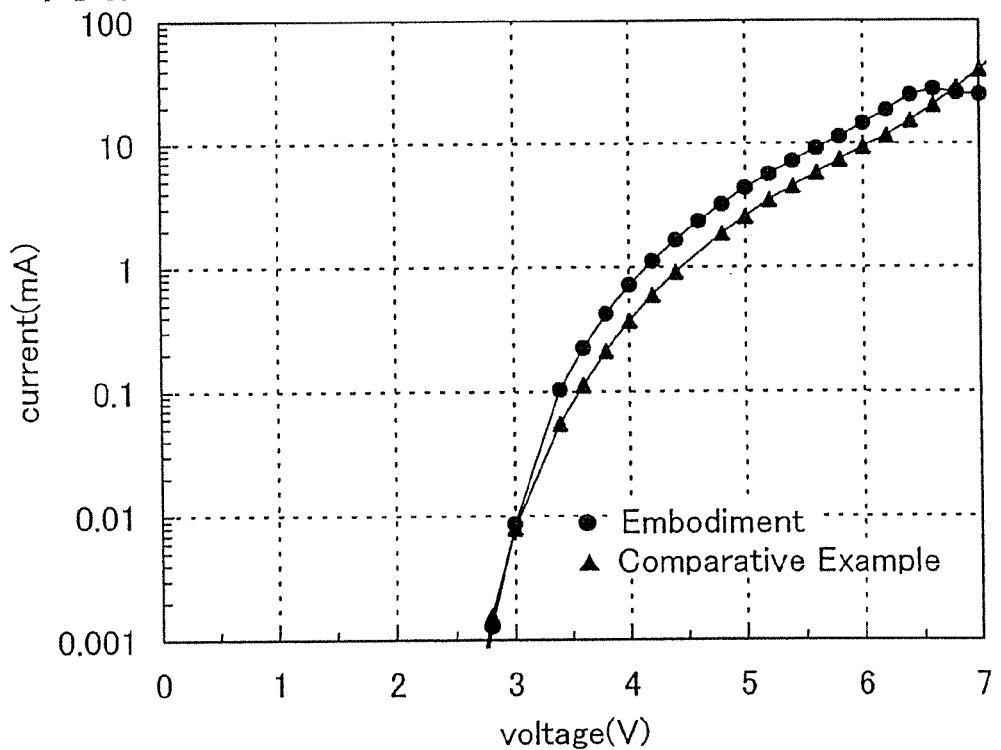

A result thereof is shown in FIGS. 16A and 16B. Note that also in this embodiment, comparison with the light-emitting element of Comparative Example 1 described in Embodiment 4, which includes Alq$_3$ instead of DNPQ that is the quinoxaline derivative of the present invention, was performed. FIG. 16A shows voltage-luminance characteristics. FIG. 16B shows voltage-current characteristics. Also in this embodiment, the results of the light-emitting elements of this embodiment and Comparative Example 1 are collectively shown in the same chart. Note that the horizontal axis represents voltage (V) and the vertical axis represents luminance (cd/m$^2$) in FIG. 16A, and the horizontal axis represents voltage (V) and the vertical axis represents current (mA) in FIG. 16B.

According to these results, the light-emitting element manufactured in this embodiment had higher luminance at lower voltage, compared to the light-emitting element of Comparative Example 1. Accordingly, it was found that the light-emitting element of this embodiment has lower drive voltage. In addition, it was also found that the light-emitting element of this embodiment had voltage-current characteristics superior to those of the light-emitting element of Comparative Example 1, and the quinoxaline derivative of the present invention had an electron-transporting property superior to that of Alq$_3$. As described above, by using the quinoxaline derivative of the present invention as an electron-transporting material, a light-emitting element with low drive voltage could be obtained. Note that the CIE chromaticity coordinates of light-emission obtained from the light-emitting element manufactured in this embodiment were (x, y)= (0.16, 0.16) at 1000 cd/m$^2$.

(Embodiment 6)

This embodiment will describe, with reference to FIG. 14, a method for manufacturing a light-emitting element in which 2,3-diphenyl-5,8-bis(2-biphenylyl)quinoxaline (abbreviation: BPPQ) synthesized in Synthesis Example 3 is used for an electron-transporting layer and operation characteristics of the light-emitting element.

First, indium tin oxide containing silicon oxide (ITSO) was deposited over a glass substrate 500 by a sputtering method, whereby a first electrode 501 was formed. The size of the electrode was set to be 2 mm×2 mm. Next, the glass substrate 500 provided with the first electrode 501 was fixed to a substrate holder in a vacuum evaporation apparatus so that the side provided with the first electrode 501 faced downward. Then, DNTPD and molybdenum trioxide were deposited by a co-evaporation method on the first electrode 501 to have a thickness of 50 nm, whereby a hole-injecting layer 511 was formed. Note that the co-evaporation was performed so that a mass ratio of DNTPD to molybdenum trioxide was 4:2 (=DNTPD: molybdenum trioxide).

Then, NPB was deposited by an evaporation method on the hole-injecting layer 511 to have a thickness of 10 nm, whereby a hole-transporting layer 512 was formed. Then, CzPA and YGAPA were deposited by a co-evaporation method on the hole-transporting layer 512 to have a thickness of 30 nm, whereby a light-emitting layer 513 was formed. Note that the co-evaporation was performed so that a mass ratio of CzPA to YGAPA was 1:0.04 (=CzPA: YGAPA). Therefore, YGAPA was in a state of being dispersed in a layer formed of CzPA.

BPPQ was deposited on the light-emitting layer 513 to have a thickness of 10 nm and then BPhen was deposited to have a thickness of 20 nm, whereby an electron-transporting layer 514 in which BPPQ and BPhen were stacked was formed. Each layer was formed by an evaporation method. LiF was deposited on the electron-transporting layer 514 by an evaporation method to have a thickness of 2 nm, whereby an electron-injecting layer 515 was formed. Then, aluminum was deposited by an evaporation method on the electron-injecting layer 515, whereby a second electrode 502 was formed.

As described above, the hole-injecting layer 511, the hole-transporting layer 512, the light-emitting layer 513, the electron-transporting layer 514, and the electron-injecting layer 515 were stacked between the first electrode 501 and the second electrode 502 to form a light-emitting element. Note that the obtained light-emitting element was sealed using a sealing material in a nitrogen atmosphere without being exposed to air. A voltage was applied to the light-emitting element of this embodiment so that potential of the first electrode 501 was higher than that of the second electrode 502, and then, operation characteristics of the light-emitting element were examined. Note that measurement was performed under a condition kept at room temperature (25° C.).

Figure 17A:
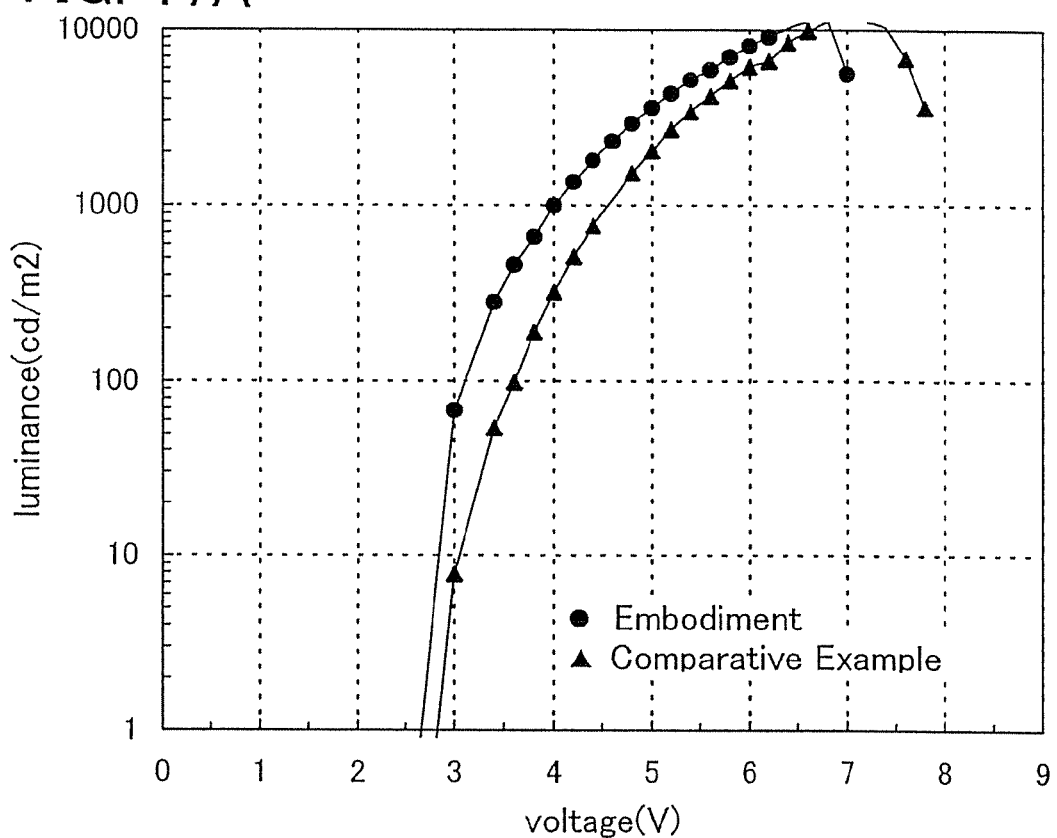
FIGS. 17A and 17B show operation characteristics of a light-emitting element manufactured in Embodiment 6.
Figure 17B:
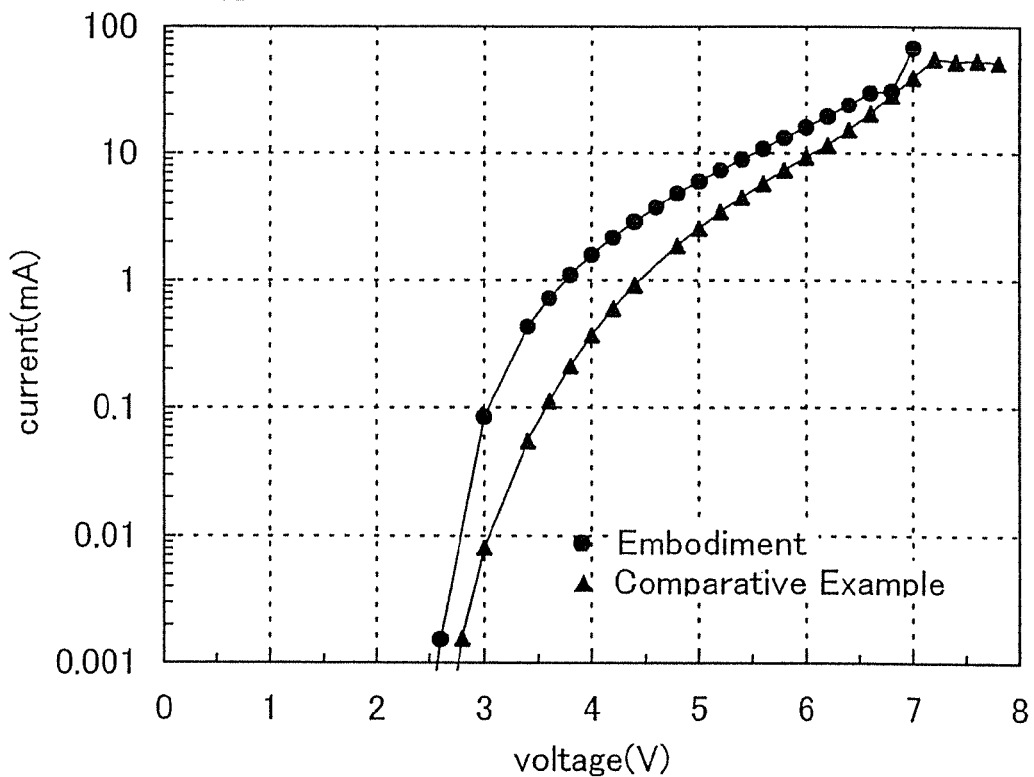

A result thereof is shown in FIGS. 17A and 17B. Note that also in this embodiment, comparison with the light-emitting element of Comparative Example 1 described in Embodiment 4, which includes Alq$_3$ instead of BPPQ that is the quinoxaline derivative of the present invention, was performed. FIG. 17A shows voltage-luminance characteristics. FIG. 17B shows voltage-current characteristics. Also in this embodiment, the results of the light-emitting elements of this embodiment and Comparative Example 1 are collectively shown in the same chart. Note that the horizontal axis represents voltage (V) and the vertical axis represents luminance (cd/m$^2$) in FIG. 17A, and the horizontal axis represents voltage (V) and the vertical axis represents current (mA) in FIG. 17B.

According to these results, the light-emitting element manufactured in this embodiment had higher luminance at lower voltage, compared to the light-emitting element of Comparative Example 1. Accordingly, it was found that the light-emitting element of this embodiment had lower drive voltage. In addition, it was also found that the light-emitting element of this embodiment had voltage-current characteristics superior to those of Comparative Example 1, and the quinoxaline derivative of the present invention had an electron-transporting property superior to that of Alq$_3$. As described above, by using the quinoxaline derivative of the present invention as an electron-transporting material, a light-emitting element with low drive voltage could be obtained. Note that the CIE chromaticity coordinates of light-emission obtained from the light-emitting element manufactured in this embodiment were (x, y)=(0.15, 0.16) at 1000 cd/m$^2$.

This application is based on Japanese Patent Application serial No. 2006-268356 filed in Japan Patent Office on Sep. 29, 2006, the entire contents of which are hereby incorporated by reference.

What is claimed is:

1. A quinoxaline derivative represented by a general formula (G1),

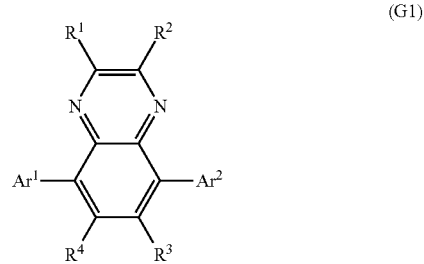

(G1)

wherein each of R$^1$ and R$^2$ represents hydrogen, wherein each of R$^3$ and R$^4$ represents hydrogen or an unsubstituted phenyl group, wherein R$^3$ and R$^4$ have the same structure, and wherein each of Ar$^1$ and Ar$^2$ has any one of structures represented by following structural formulas (2'-5) to (2'-7)

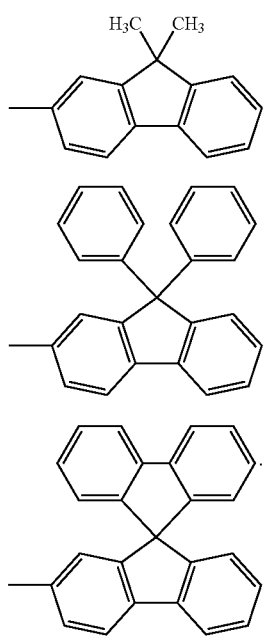

(2'-5)

(2'-6)

(2'-7)

2. A light-emitting element comprising the quinoxaline derivative according to claim 1 between a pair of electrodes.

3. A light-emitting device comprising a plurality of light-emitting elements which comprise the quinoxaline derivative according to claim 1 between a pair of electrodes.

4. An electronic appliance including a light-emitting device comprising a plurality of light-emitting elements which comprise the quinoxaline derivative according to claim 1 between a pair of electrodes.

5. The quinoxaline derivative according to claim 1, wherein the $Ar^1$ and the $Ar^2$ in the general formula (G1) have the same structure.

* * * * *

UNITED STATES PATENT AND TRADEMARK OFFICE
CERTIFICATE OF CORRECTION

| | | |
|---|---|---|
| PATENT NO. | : 8,283,052 B2 | Page 1 of 1 |
| APPLICATION NO. | : 11/860190 | |
| DATED | : October 9, 2012 | |
| INVENTOR(S) | : Egawa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1183 days.

Signed and Sealed this
Twenty-third Day of September, 2014

Michelle K. Lee
*Deputy Director of the United States Patent and Trademark Office*